US011866416B2

(12) United States Patent
Velu et al.

(10) Patent No.: US 11,866,416 B2
(45) Date of Patent: Jan. 9, 2024

(54) ***STREPTOCOCCUS MUTANS* GLUCOSYL TRANSFERASE INHIBITORS FOR DENTAL CARIES THERAPY**

(71) Applicant: UAB Research Foundation, Birmingham, AL (US)

(72) Inventors: Sadanandan E. Velu, Birmingham, AL (US); Hui Wu, Hoover, AL (US); Qiong Zhang, Sichuan (CN); Bhavitavya Nijampatnam, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 17/044,483

(22) PCT Filed: Apr. 3, 2019

(86) PCT No.: PCT/US2019/025593
§ 371 (c)(1),
(2) Date: Oct. 1, 2020

(87) PCT Pub. No.: WO2019/195430
PCT Pub. Date: Oct. 10, 2019

(65) Prior Publication Data

US 2021/0115007 A1 Apr. 22, 2021

Related U.S. Application Data

(60) Provisional application No. 62/779,796, filed on Dec. 14, 2018, provisional application No. 62/651,898, filed on Apr. 3, 2018.

(51) Int. Cl.

| | |
|---|---|
| ***C07D 333/62*** | (2006.01) |
| ***A61P 43/00*** | (2006.01) |
| ***A61K 6/00*** | (2020.01) |

(52) U.S. Cl.
CPC .............. *C07D 333/62* (2013.01); *A61K 6/00* (2013.01); *A61P 43/00* (2018.01)

(58) Field of Classification Search
CPC ...... C07D 333/62; C07D 215/48; A61K 6/00; A61K 6/20; A61K 6/69; A61P 43/00; A61P 31/04; A61P 1/02; G01N 2333/91091; G01N 2500/04; G01N 33/573; C07C 49/84; C07C 49/835; Y02P 20/55
See application file for complete search history.

(56) References Cited

PUBLICATIONS

Small-Molecule Modulation of Read-Through (SMMRT): Modification of 2-Phenoxyacetanilides to Improve Solution Solubility. Richard G. Wilde et al., An IP.com Prior Art Database Technical Disclosure, Authors et. al.: Disclosed Anonymously, IP.com No. IPCOM000019283D, IP.com (Year: 2003).*

(Continued)

*Primary Examiner* — Kortney L. Klinkel
*Assistant Examiner* — Padmaja S Rao
(74) *Attorney, Agent, or Firm* — Myers Bigel, P.A.

(57) ABSTRACT

The present invention is related to the inhibition of the formation of Streptococci biofilms through the inhibition of glucosyl transferase (Gtf). Compounds, compositions and methods for inhibiting *Streptococcus* biofilm formation, as well as for preventing, inhibiting and/or treating the formation of dental caries, and methods of identifying compounds that prevent, inhibit and/or treat the formation of dental caries are provided.

20 Claims, 22 Drawing Sheets

Specification includes a Sequence Listing.

(56) References Cited

PUBLICATIONS

FDA approved solvents (Guidance for Industry, Q3C—Tables and List, U.S. Department of Health and Human Services, Food and Drug Administration, Center for Drug Evaluation and Research (CDER), Center for Biologics Evaluation and Research (CBER), Nov. 2003, ICH, Revision 1) (Year: 2003).*

Nijampatnam et al., Hydroxychalcone inhibitors of *Streptococcus mutans* glucosyl transferases and biofilms as potential anticaries agents, Bioorganic & Medicinal Chemistry Letters, vol. 26, 3508-3513, Jun. 14, 2016 (Year: 2016).*

Zhang et al., Structure-Based Discovery of Small Molecule Inhibitors of Cariogenic Virulence, Scientific Reports, vol. 7, No. 5974, 1-10, Jul. 20, 2017 (Year: 2017).*

Huang et al., Synthesis and Preliminary Antitumor Activities of Aurone Derivatives, Chinese Journal of Organic Chemistry, vol. 33, 2565-2571, 2013 (Year: 2013).*

* cited by examiner

FIG. 1
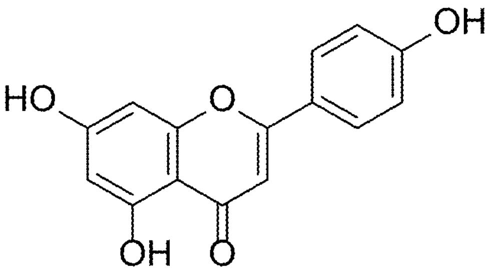
Apigenin
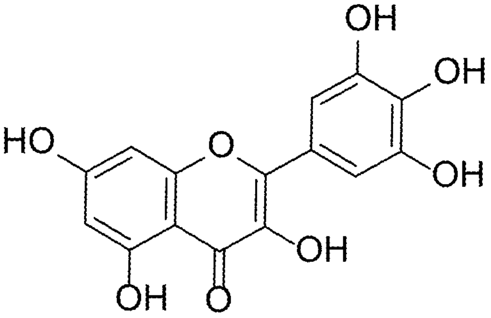
Myricetin
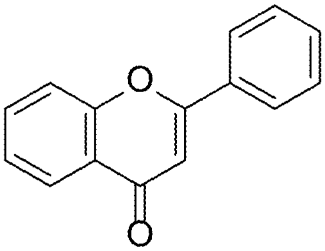
Flavone
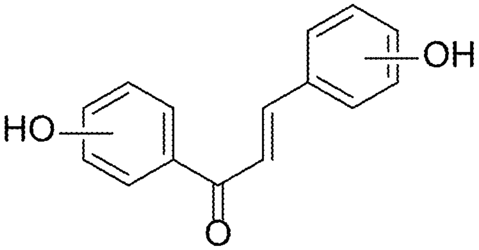
Hydroxychalcone

G3 #G16 #G39 #G12 #G27 #G43 #G45

FIG. 7D
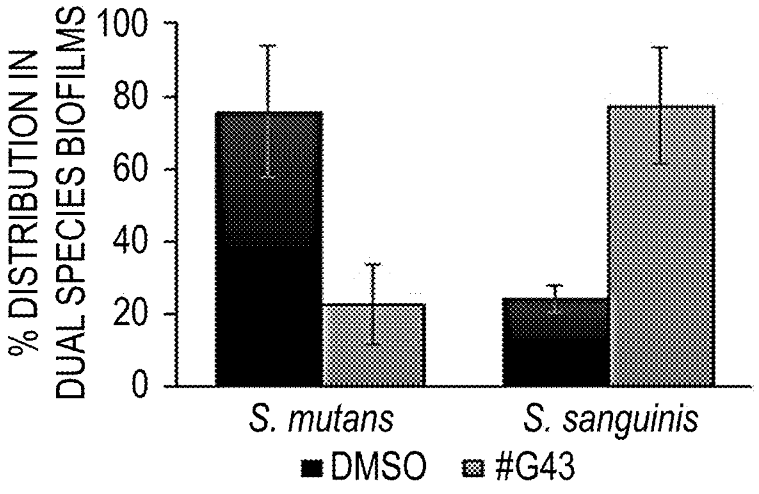
FIG. 7E
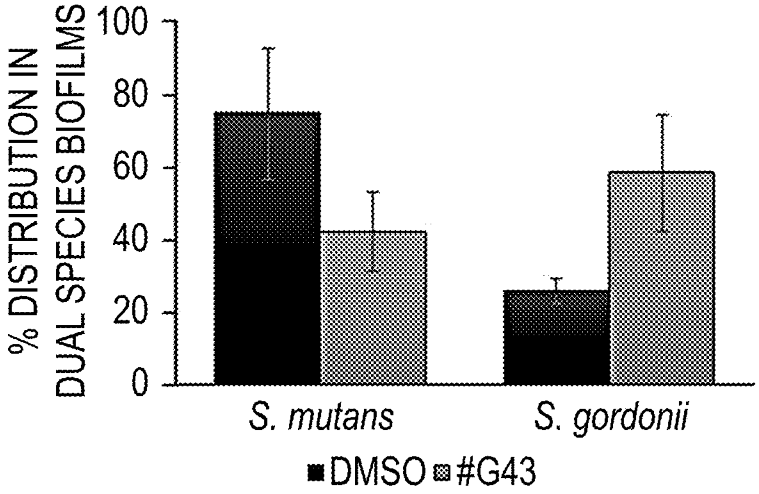
FIG. 7F
| | % DISTRIBUTION IN DUAL SPECIES BIOFILMS* | |
|---|---|---|
| | *S. mutans* | *S. sanguinis* |
| **DMSO** | 75.7±18 | 24.3±10 |
| **#G43** | 22.8±4 | 77.2±16 |
| | % DISTRIBUTION IN DUAL SPECIES BIOFILMS* | |
|---|---|---|
| | *S. mutans* | *S. gordonii* |
| **DMSO** | 74.3±14 | 25.7±15 |
| **#G43** | 42.0±11 | 58.0±13 |
*AS DETERMINED BY CFU COUNTING ON BAP.

| | | CFU/mL (x$10^5$) | | BUCCAL | | | | SULCAL | | | | PROXIMAL | | | |
|---|---|---|---|---|---|---|---|---|---|---|---|---|---|---|---|
| | WEIGHT | (MS) | (BAP) | E | Ds | Dm | Dx | E | Ds | Dm | Dx | E | Ds | Dm | Dx |
| **CONTROL** | 143±13 | 7.1±0.8 | 7.2±0.8 | 16.2±0.2 | 14.0±0.8 | 10±0.8 | 6.6±0.4 | 24.2±0.6 | 20.8±0.7 | 11.8±1 | 6.2±0.7 | 8±0 | 4.8±0.5 | 0.2±0.2 | 0 |
| **#G43** | 144±10 | 4.4±0.5 | 4.6±0.6 | 5.6±0.2 | 2.8±0.4 | 1.4±0.5 | 0.4±0.2 | 14±0.6 | 9.6±0.5 | 3.2±0.5 | 1.6±0.4 | 1.6±0.7 | 0±0 | 0±0 | 0 |

**TABLE 1. EFFECTS OF THE LEAD COMPOUND ON BACTERIAL COLONIZATION AND MEAN CARIES SCORES *IN VIVO***
TWO GROUPS OF 6 RATS INFECTED WITH *S. MUTANS* UA159, AND TREATED WITH OR WITHOUT #G43.
CARIES SCORES
BUCCAL: ENAMEL (E); P<0.001: DENTINAL SLIGHT (DS); P<0.001: DENTINAL MODERATE (DM); P<0.001: DENTINAL EXTENSIVE (DX); P<0.001.
SULCAL: (E); P<0.001: (DS); P<0.001: (DM); P<0.001: (DX); P<0.001.
PROXIMAL: (E); P<0.001: (DS); P<0.001: (DM); NO SIGNIFICANCE: (DX); NO SIGNIFICANCE.
BACTERIAL COLONIZATION
CFU/mL; NO SIGNFICANCE.
WEIGHTS
NO SIGNFICANCE.

FIG. 10A
G43 $^1$H NMR (300 MHz, DMSO-$d_6$)
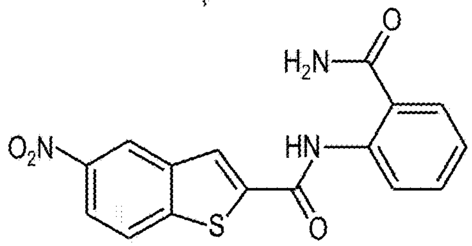
G43
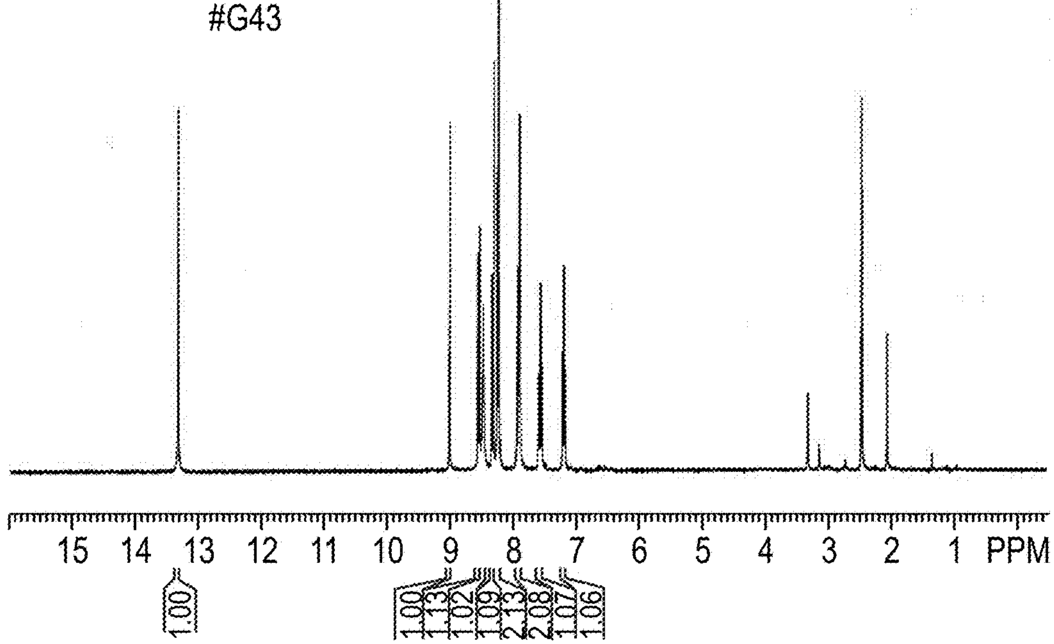
| | |
|---|---|
| CURRENT DATA PARAMETERS | |
| NAME | SN-1-204 |
| EXPNO | 2 |
| PROCNO | 1 |
| F2 – ACQUISITION PARAMETERS | |
| DATE | 20140123 |
| TIME | 9.55 |
| INSTRUM | SPECT |
| PROBHD | 5 mm DUL 13C-1 |
| PULPROG | ZG30 |
| TD | 65536 |
| SOLVENT | DMSO |
| NS | 16 |
| DS | 2 |
| SWH | 6188.119 Hz |
| FIDRES | 0.094423 Hz |
| AQ | 5.2953587 sec |
| RG | 512 |
| DW | 80.800 usec |
| DE | 6.00 usec |
| TE | 300.0 K |
| D1 | 1.00000000 sec |
| TD0 | 1 |
| ——— CHANNEL F1 ——— | |
| NUC1 | 1H |
| P1 | 15.00 usec |
| PL1 | -2.50 dB |
| SFO1 | 299.8818519 MHz |
| F2 – PROCESSING PARAMETERS | |
| SI | 32768 |
| SF | 299.8799979 MHz |
| WDW | NO |
| SSB | 0 |
| LB | 0.00 Hz |
| GB | 0 |
| PC | 1.00 |

FIG. 11A
G43-D ¹H NMR (300 MHz, DMSO-d$_6$)
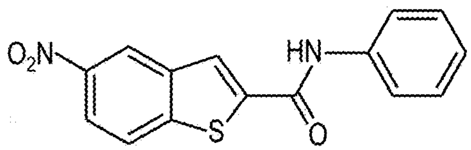
G43-D
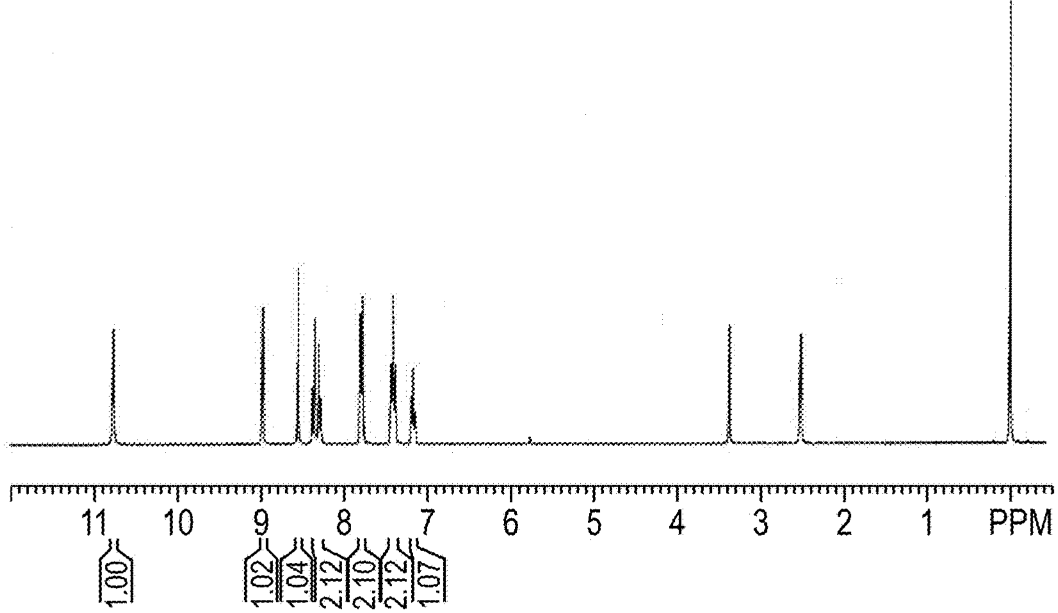
CURRENT DATA PARAMETERS
NAME HW-1-184
EXPNO 1
PROCNO 1
F2 – ACQUISITION PARAMETERS
DATE 20141112
TIME 19.06
INSTRUM SPECT
PROBHD 5 mm DUL 13C-1
PULPROG ZG30
TD 65536
SOLVENT DMSO
NS 16
DS 2
SWH 6188.119 Hz
FIDRES 0.094423 Hz
AQ 5.2953587 sec
RG 362
DW 80.800 usec
DE 6.00 usec
TE 300.0 K
D1 1.00000000 sec
TD0 1
---------- CHANNEL F1 ----------
NUC1 1H
P1 15.00 usec
PL1 -2.50 dB
SFO1 299.8818519 MHz
F2 – PROCESSING PARAMETERS
SI 32768
SF 299.8810990 MHz
WDW NO
SSB 0
LB 0.00 Hz
GB 0
PC 1.00

FIG. 11B

#G43-D $^{13}C$ NMR (300 MHz, DMSO-$d_6$)

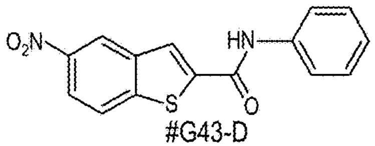

#G43-D

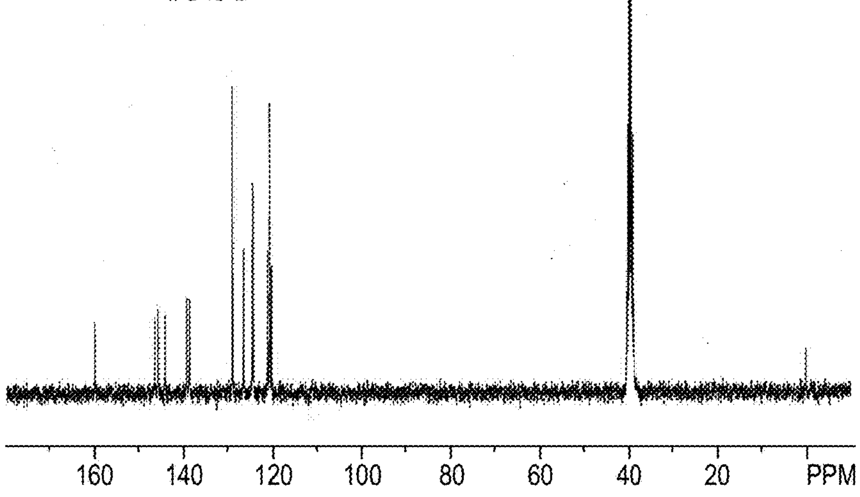

CURRENT DATA PARAMETERS
NAME HW-1-184
EXPNO 5
PROCNO 1

F2 – ACQUISITION PARAMETERS
DATE 20141118
TIME 11.38
INSTRUM SPECT
PROBHD 5 mm DUL 13C-1
PULPROG ZGPG30
TD 65536
SOLVENT DMSO
NS 303
DS 4
SWH 17985.611 Hz
FIDRES 0.274439 Hz
AQ 1.8219508 sec
RG 32768
DW 27.800 usec
DE 6.00 usec
TE 300.0 K
D1 2.00000000 sec
D11 0.03000000 sec
DELTA 1.89999998 sec
TD0 1

———— CHANNEL F1 ————
NUC1 13C
P1 8.00 usec
PL1 -1.80 dB
SFO1 75.4124265 MHz

———— CHANNEL F2 ————
SPDPRG2 WALTZ16
NUC2 1H
PCPD2 75.00 usec
PL2 -2.50 dB
PL12 11.48 dB
PL13 12.00 dB
SFO2 299.8811995 MHz F2 – PROCESSING PARAMETERS
SI 32768
SF 75.4048860 MHz
WDW EM
SSB 0
LB 1.00 Hz
GB 0
PC 1.40

*STREPTOCOCCUS MUTANS* GLUCOSYL TRANSFERASE INHIBITORS FOR DENTAL CARIES THERAPY

STATEMENT OF PRIORITY

This application is a 35 U.S.C. § 371 national phase application of PCT Application PCT/US2019/025593 filed Apr. 3, 2019, which claims the benefit, under 35 U.S.C. § 119(e), of U.S. Provisional Application No. 62/779,796 filed on Dec. 14, 2018, and U.S. Provisional Application No. 62/651,898 filed on Apr. 3, 2018, the entire contents of each of which are incorporated by reference herein in its entirety.

STATEMENT OF GOVERNMENT SUPPORT

This invention was made with government support under Grant Nos. F31 DE025783, R03 DE025058, and R01 DE022350 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5656-67_ST25.txt, 2,836 bytes in size, generated on Oct. 1, 2020 and filed via EFS-Web, is provided in lieu of a paper copy. This Sequence Listing is incorporated by reference into the specification for its disclosures.

FIELD OF THE INVENTION

The present invention relates to compositions that inhibit the formation of biofilms that lead to tooth decay. Mutans streptococci, represented by *Streptococcus mutans*, have been indicated as the major etiological agent in the initiation and development of dental caries. The formation of tenacious biofilms is the hallmark of *S. mutans* induced pathogenesis of dental caries. One of the key virulence factors of *S. mutans* is its ability to initiate biofilm formation through glucosyl transferase (GTF)-mediated sucrose-dependent mechanisms. The compounds and compositions of the present invention, methods of using the same and methods of identifying compositions that inhibit *S. mutans* GTF are related to the prevention and inhibition of the formation of dental caries.

BACKGROUND OF THE INVENTION

Dental caries is a multifactorial disease of bacterial origin that is characterized by the localized destruction of dental hard tissues. This ubiquitous disease results from the interactions between bacteria, diet, and host conditions (Marsh, (2003) *Microbiology* 149, 279; Bowen (2002) *Critical Reviews in Oral Biology & Medicine* 13, 126). *Streptococcus mutans* is a key contributor to the pathogenesis, although other microorganisms are also involved (Xiao and Koo (2010) *Journal of Applied Microbiology* 108, 2103). The development of dental caries is initiated by production of sticky glucosyl polymers (glucans), a major component of the biofilm matrix-exopolysaccharides (EPS) of *S. mutans*, which orchestrate the formation of cariogenic biofilm plaque (Koo et al. (2010) *Journal of Bacteriology* 192, 3024; Schilling and Bowen (1998) *Journal of Dental Research* 67, 2). The biofilm assembly renders bacteria more pathogenic. Thus, the synthesis of glucans is considered to be one of the essential virulence traits of *S. mutans* (Vacca-Smith and Bowen (1998) *Arch. Oral Biol.* 43, 103; Shirizowa et al. (1986) *Infection and Immunity* 53, 587). In *S. mutans*, three Gtfs express different enzyme activities. GtfB synthesizes insoluble glucans exclusively, GtfC synthesizes both insoluble and soluble glucans, while GtfD only produces water-soluble glucans (Hanada and Kuramitsu (1988) *Infection and Immunity* 56, 1999; Hanada and Kuramitsu (1989) *Infection and Immunity* 57, 2079; Walker et al. (1981) *Journal of General Microbiology* 127, 201). GtfB and GtfC have a high degree of amino acid sequence identity (~76%). Glucans produced by GtfB and GtfC appear to be essential for the assembly of the *S. mutans* biofilm extracellular matrix (Schilling and Bowen (1998) *Journal of Dental Research* 67, 2). Soluble glucans produced by GtfD not only serve as a primer for GtfB, but also function as a nutrient source for *S. mutans* and other bacteria (Venkataraman et al. (1995) *Journal of Dental Research* 74, 1695; Lingstrom et al. (2000) *Critical Reviews of Oral Biology and Medicine* 11, 366), which provides simple sugar substrates for bacteria to produce lactic acid that leads to demineralization of the tooth surface and ensues cariogenesis.

Current strategies to prevent dental caries are aimed to eliminate bacteria non-discriminatively through chemical and physical means, in addition to manipulating the remineralization process through the use of fluoride (Zhu et al. (2015) *Journal of Dental Research* 94, 659). An approach targeting a unique pathogen such as *S. mutans* has been established successfully, but it also affects overall microbiota (Duarte et al. (2006) *FEMS Microbiology Letters* 257, 50). It is desirable to develop virulence-selective therapeutics given the critical role biofilms play in dental caries development. Targeting the Gtfs from *S. mutans* is an attractive strategy as it offers selectivity that may preserve the natural microbial flora of the mouth (Stauder et al. (2010) *Current Microbiology* 61, 417). Small molecule inhibitors of *S. mutans* growth and biofilms have been reported (Koo et al. (2002) *Antimicrobial Agents and Chemotherapy* 46, 1302; Feldman et al. (2009) *Alternative Therapies in Health &Medicine* 15, 32; Gregoire et al. (2007) *Journal of Applied Microbiology* 103, 1960; Pan et al. (2015) *Journal of Applied Microbiology* 119, 1403; Nijampatnam et al. (2014) *Microorganisms* 2, 128; Coenye et al. (2007) *Antimicrobial Agents and Chemotherapy* 51, 1541; Koo et al. (2003) *The Journal of Antimicrobial Chemotherapy* 52, 782). Numerous inhibitors have been evaluated as anti-biofilm compounds as they modulate expression of Gtfs (Murata et al. (2008) *FEMS Microbiology Letters* 282, 174; Liu et al. (2011) *Antimicrobial Agents and Chemotherapy* 55, 2679; Ren et al. (2015) *Antimicrobial Agents and Chemotherapy* 60, 126; Hamada and Slade (1980) *Microbiological Reviews* 44, 331; Kralj et al. (2004) *Microbiology* 150, 3681), and/or other virulence factors. However the selectivity of those bioactive small molecules is not known, and remains to be elucidated.

As members of glycoside hydrolase (GH) family 70, Gtfs contain a central conserved catalytic region (Ito et al. (2011) *J Mol. Biol.* 408, 177; Loo et al. (2000) *J. Bacteriol.* 182, 1374). The structures of the GtfC catalytic domain, and its complexes with acarbose and maltose have recently been determined (Zhang et al. (2015) *International Journal of Antimicrobial Agents* 46, 174). Structural details provide us with key insights for the design and development of novel Gtf inhibitors.

In addition, since diet is one of the key factors that define oral health, research has mainly been focused on widely consumed food products. Numerous studies have been conducted comparing the efficacies of flavonols and low-molecular-weight polyphenols found in cranberries (Duarte et al. (2006) *FEMS Microbiology Letters* 257, 50) Flavones and flavonols were inhibitors of Gtfs; of these, a compound called apigenin (4',5,7-trihydroxyflavone, Scheme 1) was the most effective inhibitor of Gtfs (Koo et al. (2003) *The Journal of Antimicrobial Chemotherapy* 52, 782). Flavonols and their glycosides such as myricetin and myricetin 3-rhamnoside exhibited significant but moderate effects (Scheme 1)(Koo et al. (2002) *Antimicrobial Agents and Chemotherapy* 46, 1302; Gregoire et al. (2007) *Journal of Applied Microbiology* 103, 1960). In addition, scaffolds found in tea (*Camellia sinensis*) that inhibit *S. mutans* biofilms attract attention due to their unique polyphenol compositions and their prevalence in the human diet (Ferrazzano et al. (2009) *Fitoterapia* 80, 255). Early studies were carried out on extracts containing multiple constituents however recent reports focus on effects of single defined component in vitro and in vivo (Koo et al. (2010) *Caries Research* 44, 116). Furthermore, these natural product compounds inhibited *S. mutans* biofilms at high micromolar and even millimolar concentrations.

Undoubtedly, flavonols are a promising class of scaffolds for the development of anticaries therapeutics. We have held a long standing interest in developing inhibitors of *S. mutans* Gtfs as an avenue to selectively inhibit the formation of cariogenic biofilms. By targeting *S. mutans*' virulence instead of its viability, the agents developed will be non-bactericidal, preserving the natural bacterial flora of the mouth, and will also be less likely to induce resistance to therapy. Encouraged by reported findings on flavonols, we were interested to examine the effect of hydroxychalcones (FIG. 1), precursors of flavonoids and isoflavonoids, for their effect on *S. mutans*' biofilm and Gtf inhibition. Chalcones were originally isolated from natural sources and are abundant in edible plants. Structurally, they can be defined as open-chain flavonoids in which two aromatic rings are joined by a three carbon α,β-unsaturated carbonyl system (Naidoo et al. (2012) *Journal of Ethnopharmacology* 144, 171). Being a minority subgroup of the flavonoid family, like other members, chalcones have been reported responsible for a variety of biological activities, including antiviral, anticancer, antimicrobial, anti-inflammatory, antioxidative, antimalarial, anti-leishmania, antinociceptive, and antiproliferative activities (Matos et al. (2015) *Expert Opinion on Therapeutic Patents* 25, 351; Das and Manna (2016) *Journal of Toxicology* 2016, 7651047). Hence, chalcones are considered to be a class of compounds with important therapeutic potential. However, to our knowledge, there are no reported experimental data regarding the antibiofilm activity of chalcones against *S. mutans.*

In view of this, objects of the present invention include compositions, method of using these compositions, and identifying compounds for use in the treatment and prevention of dental caries.

SUMMARY OF THE INVENTION

The present invention relates to the inhibition of glucosyltransferases (Gtfs) and the inhibition of the formation of *Streptococcus*-mediated biofilm formation, which provides the basis for the compounds, compositions and methods of the present invention.

Thus, in an aspect of the invention, provided are compounds and compositions for the prevention and/or inhibition of the formation of dental caries in a subject.

In another aspect of the invention, the compounds and compositions of the present invention include glucosyltransferase (Gtf) inhibitors. In some aspects, the Gtf inhibitor of the composition may include a benzothiophene, a quinoline or a hydroxychalcone, or a derivative of any one thereof.

In yet another aspect of the invention, provided are formulations that include compounds or compositions for the prevention, treatment and/or inhibition of the formation of dental caries in a subject.

In yet another aspect of the invention, provided is a method for preventing, inhibiting and/or treating the formation of dental caries in a subject, the method including the administration of the compounds, compositions or formulations of the present invention.

In yet another aspect of the invention, provided is a method of identifying compounds for preventing, inhibiting and/or treating the formation of dental caries in a subject.

The foregoing and other objects and aspects of the present invention are explained in further detail as set forth below.

BRIEF DESCRIPTION OF THE DRAWINGS

FIG. 1 shows known inhibitors of *S. mutans* biofilm and *S. mutans* Gtfs and general structures of flavone and hydroxychalcone.

FIG. 3A shows effects of lead compounds #G16 and #G43 at 25 μM on the activity of Gtfs from wild type *S. mutans*. FIG. 3B shows effects of lead compounds #G16 and #G43 at 25 μM on the activity of GtfB from *S. mutans* GtfCD mutants. FIG. 3C shows effects of lead compounds #G16 and #G43 at 25 μM on the activity of Gtfs from wild type *S. mutans*. FIG. 3C shows effects of lead compounds #G16 and #G43 at 25 μM on the activity of GtfC from *S. mutans* GtfBD mutants.

FIG. 6A shows effects on *S. mutans. S. mutans* was treated with DMSO and a serial dilution of #G43. The cell viability was determined by the numbers of CFU in a logarithmic scale. FIG. 6B shows effects on commensal species. *S. gordonii, S. sanguinis*, and *S. mutans* were treated with 200 μM of the compound or DMSO, and bacterial growth was measured at $OD_{470}$, and normalized to the DMSO control (100%). FIG. 6C shows effects on *Aggregatibacter actinomycetemcomitans* and *Actinomyces naeslundii. A. actinomycetemcomitans* and *A. naeslundii* were treated with the lead compound at 200 μM or 25 μM or DMSO control, bacterial growth was measured at $OD_{470}$, and normalized to the DMSO control (100%). Values represent the means±standard deviations from three independent experiments. NS indicates that the cell viability between DMSO control and compound-treated groups was not significantly different. The P value>0.05 is considered to be not significant.

FIGS. 7A-7F show effects of compound #G43 on commensal single and dual species biofilms. FIG. 7A shows *S. mutans, S. gordonii*, and *S. sanguinis* treated with DMSO or 25 μM of compound #G43, and the biomasses of each treated biofilm quantitated by crystal violet staining and measured at $OD_{562}$. FIG. 7B shows the cell viability of dual species biofilms, determined by the numbers of CFU in a logarithmic scale using *S. mutans* and *S. sanguinis*. FIG. 7C shows the cell viability of dual species biofilms, determined by the numbers of CFU in a logarithmic scale using *S. mutans* and *S. gordonii*. FIG. 7D shows species distribution in dual species biofilms with *S. mutans* and *S. sanguinius*. FIG. 7E shows species distribution in dual species biofilms with *S. mutans* and *S. gordonii*. Bars in FIGS. 7D and 7E represent the mean and standard deviations of three independent experiments. FIG. 7F shows the species distribution in dual species biofilms with *S. mutans* and *S. sanguinius* and, *S. mutans* and *S. gordonii* in tabular form. Bars represent the mean and standard deviations of three independent experiments. *P<0.05.

FIG. 8A shows chemical structures of lead and its inactive analog. Docking poses of (FIG. 8B) Compound #G43 and (FIG. 8C) Compound #G43-D in skeleton are shown. Three key residue interactions are depicted by displaying residue chains. FIG. 8D shows the effects of active and inactive compound on the activity of Gtfs by zymographic assays. Glucan zymographic assays (bottom panel) were performed using SDS-PAGE analysis of Gtfs from culture supernatants of *S. mutans* UA159 incubated with vehicle control DMSO, the synthesized active #G43, and its derivative at 50 μM. SDS-PAGE analysis of Gtfs (top panel) was used as a loading control. FIG. 8E shows fluorescent microscopy images of *S. mutans* UA159 biofilms treated with DMSO control, the synthesized #G43, and its derivative #G43-D at 100 μM. Viable bacterial cells were stained with 2.5 μM Syto9.

FIG. 9 shows the effects of the lead compound on bacterial colonization and mean caries scores in vivo.

FIGS. 10A-10B show NMR spectra for (FIG. 10A) compound #G43 $^{1}H$ NMR and (FIG. 10B) #G43 $^{13}C$ NMR.

FIGS. 11A-11B show NMR spectra for (FIG. 11A) compound #G43-D $^{1}H$ NMR and (FIG. 11B) #G43-D $^{13}C$ NMR.

FIG. 13D shows fluorescent microscopy images of *S. mutans* colonization in *Drosophila*, with the following conditions: (Panel a) treatment with DMSO, (Panel b) ΔgtfB mutant strain, (Panel c) treatment with 50 μM 9b and (Panel d) treatment with 50 μM 9a.

FIG. 16E shows results of the zymogram assay conducted with serial dilution concentrations of piceatannol. FIG. 16F shows results of the zymogram assay comparing effect of compound treatment on the GTF enzyme production.

FIG. 18A shows mean enamel caries scores (±SEM) of rats infected starting at 19 days of age and placed on Diet 305. FIG. 18B shows CFU/mandible determined by plating on MS plates. Resveratrol to Water, p<0.05; Piceatannol to Water, p<0.01.

DETAILED DESCRIPTION OF THE INVENTION

Figure 2A:
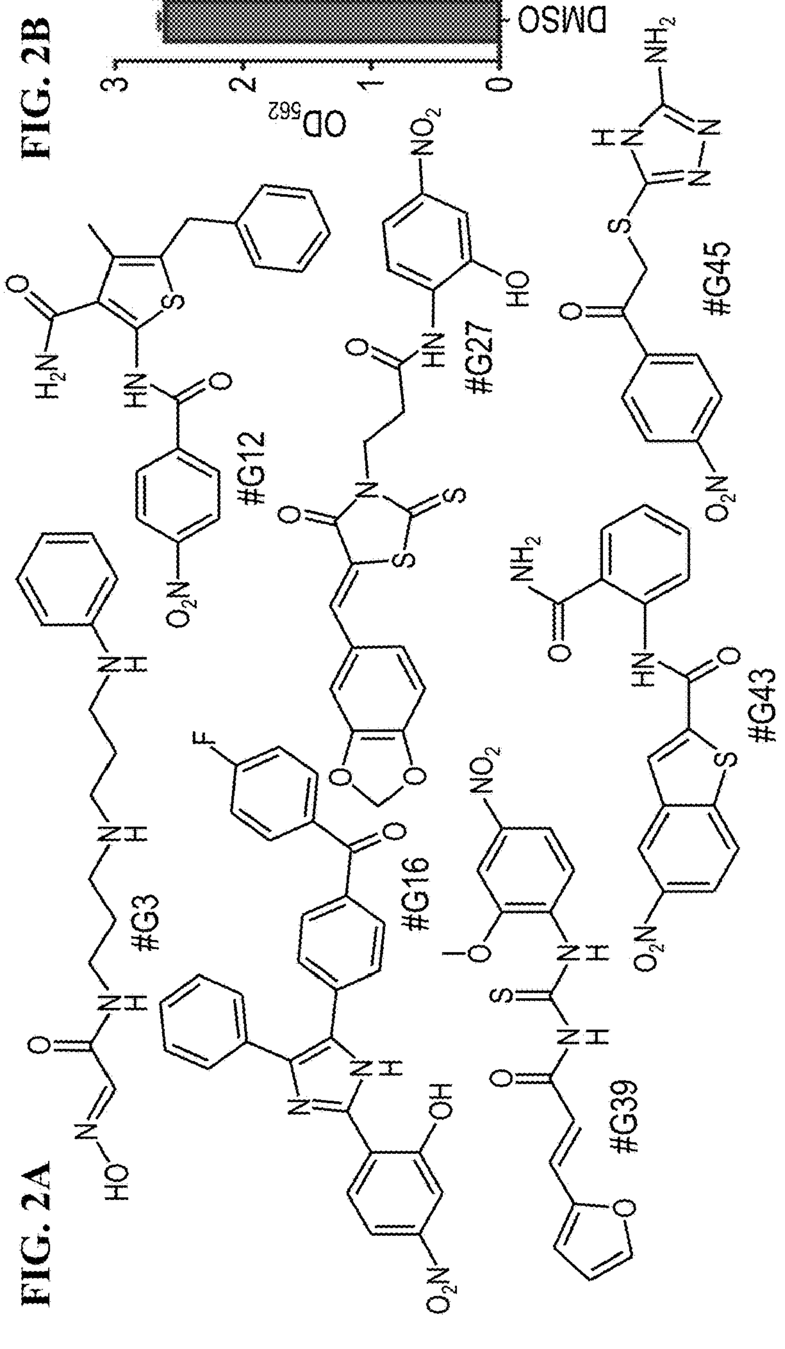
FIG. 2A shows structures of the seven most potent Gtf inhibitors of *S. mutants* biofilms.

In the following detailed description, embodiments of the present invention are described in detail to enable practice of the invention. Although the invention is described with reference to these specific embodiments, it should be appreciated that the invention can be embodied in different forms and should not be construed as limited to the embodiments set forth herein. Rather, these embodiments are provided so that this disclosure will be thorough and complete, and will fully convey the scope of the invention to those skilled in the art. All publications cited herein are incorporated by reference in their entireties for their teachings.

The invention includes numerous alternatives, modifications, and equivalents as will become apparent from consideration of the following detailed description.

Unless otherwise defined, all technical terms used herein have the same meaning as commonly understood by one of ordinary skill in the art to which this disclosure belongs.

"Alkyl" as used herein alone or as part of another group, refers to a straight or branched chain hydrocarbon containing from 1 to 10 carbon atoms (e.g., C1-C10 alkyl, C1-C9 alkyl, C1-C8 alkyl, C1-C7 alkyl, C1-C6 alkyl, C1-C4 alkyl, C1-C3 alkyl, and/or C1-C2 alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. The term "akyl" is intended to include both substituted and unsubstituted alkyl groups unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 2 to 10 carbon atoms (e.g., C2-C10 alkenyl, C2-C9 alkyenyl, C2-C8 alkenyl, C2-C7 alkenyl, C2-C6 alkenyl, C2-C5 alkenyl, C2-C4 alkenyl, and/or C2-C3 alkenyl) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" is intended to include both substituted and unsubstituted alkenyl groups unless otherwise indicated and these groups may be substituted with groups as described in connection with alkyl above.

"Alkynyl" as used herein alone or as part of another group, refers to a straight or branched chain hydrocarbon containing from 2 to 10 carbon atoms (e.g., C2-C10 alkynyl, C2-C9 alkynyl, C2-C8 alkynyl, C2-C7 alkynyl, C2-C6 alkynyl, C2-C5 alkynyl, C2-C4 alkynyl, and/or C2-C3) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" is intended to include both substituted and unsubstituted alkynyl groups and these groups may be substituted with the same groups as set forth in connection with alkyl above.

"Halo" as used herein refers to any suitable halogen, including —F, —Cl, —Br, and —I.

Also as used herein, the terms "treat," "treating" or "treatment" may refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the condition, disorder, disease or illness and/or change in clinical parameters of the condition, disorder, disease or illness, etc., as would be well known in the art.

As used herein, the terms "prevent," "preventing" or "prevention of" (and grammatical variations thereof) may refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. In representative embodiments, the term "prevent," "preventing," or "prevention of" (and grammatical variations thereof) refer to prevention and/or delay of the onset of a disease in the subject, with or without other signs of clinical disease. The prevention can be complete, e.g., the total absence of the disease, disorder and/or clinical symptom(s). The prevention can also be partial, such that the occurrence of the condition, disease, disorder and/or clinical symptom(s) in the subject and/or the severity of onset are less than what would occur in the absence of the present invention.

An "effective amount" or "therapeutically effective amount" may refer to an amount of a compound, composition or formulation of this invention that is sufficient to produce a desired effect, which can be a therapeutic and/or beneficial effect. The effective amount will vary with the age, general condition of the subject, the severity of the condition being treated, the particular agent administered, during the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

The term "pharmaceutically acceptable" indicates approval by a regulatory agency of the Federal or a state government or listed in the U.S. Pharmacopeia or other generally recognized pharmacopeia such as the European Pharmacopeia, for use in animals, and more particularly in humans. One method for solubilizing poorly water soluble or water insoluble drugs is to form a salt of the drug or to prepare a prodrug that is more soluble itself or that can be used to form a water soluble salt of the prodrug. Methods for forming salts and pharmaceutically acceptable salt forms are known in the art and include, without limitation, salts of acidic or basic groups that may be present in the drug or prodrug of interest. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1, 1'-methylene-bis-(2-hydroxy-3-naphthoate)) salts. Compounds that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

The present invention is based on the inhibition of Gtf and the inhibition of biofilm formation, more particularly *Streptococcus*-mediated biofilm formation, for the prevention, treatment and/or inhibition of the formation of dental caries, or the prevention, treatment and/or inhibition of the formation of denture plaques, in a subject in need thereof.

In an embodiment of the invention, provided are compounds that are inhibitors of Gtf and that inhibit *Streptococcus*-mediated biofilm formation for the prevention, treatment and/or inhibition of the formation of dental caries, or the prevention, treatment and/or inhibition of the formation of denture plaques, in a subject in need thereof. In some embodiments, the *Streptococcus* biofilms are *Streptococcus mutans* biofilms.

In an embodiment of the invention, a compound inhibiting Gtf and/or biofilm formation is a compound of formula (I):

(I)

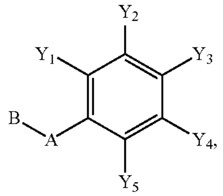

wherein:

A is —NH—, —O—, —$CH_2$—, —S(O)—, —$S(O)_2$—, —NHC(═NH)NH—, —NHC(═O)NH—, or a bond;

B is a structure selected from the group consisting of:

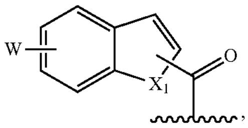,

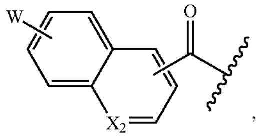,

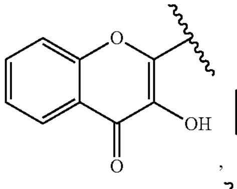,

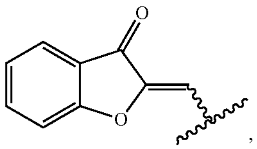,

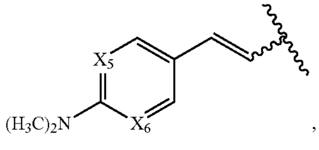,

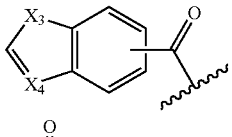,

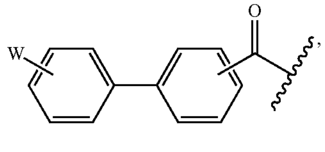,

-continued

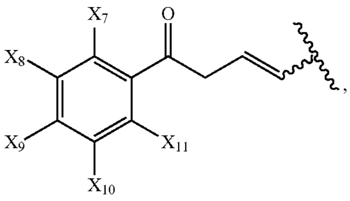,

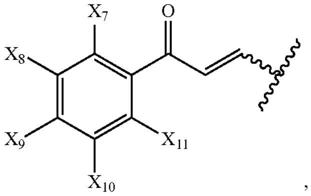,

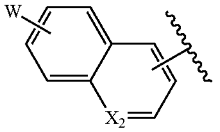

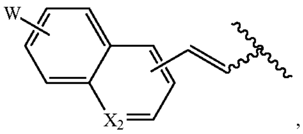, and

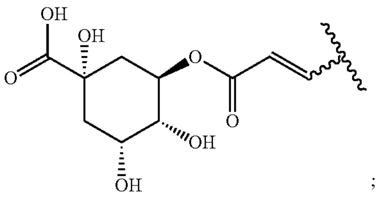;

W is selected from the group consisting of —H, —$N_3$, -Halo (e.g., Cl, Br, F, I), —$NH_2$, —$NO_2$, —CN, —OH, —SH, —C(═O)OH, —C(═O)H, —$CH_2$(Halo), —CH$(Halo)_2$, —$C(Halo)_3$, —O($C_1$-$C_6$ alkyl) (e.g., —$OCH_3$), —NH($C_1$-$C_6$ alkyl), —C(═O)$NH_2$, —S($C_1$-$C_6$ alkyl), —OC(═O)($C_1$-$C_6$ alkyl), —NHC(═O)($C_1$-$C_6$ alkyl), —C(═O)O($C_1$-$C_6$ alkyl) (e.g., C(═O)$OCH_3$), —C(═O)($C_1$-$C_6$ alkyl), —C(═O)NH($C_1$-$C_6$ alkyl), —$C_2$-$C_{10}$ alkenyl, —$C_2$-$C_{10}$ alkynyl, —$C_1$-$C_{10}$ alkyl (e.g., —$C_1$-$C_4$ alkyl), and

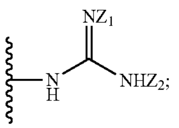;

$X_1$, $X_3$, and $X_4$ are independently selected from the group consisting of —N—, —S— and —O—;

$X_2$, $X_5$ and $X_6$ are independently selected from —N— or —C—;

$Y_1$, $Y_2$, $Y_3$, $Y_4$, and $Y_5$ are independently selected from the group consisting of —H, —$N_3$, -Halo (e.g., Cl, Br, F, I), —$NO_2$, —CN, —OH, —SH, —C(═O)OH, —C(═O)H, —C(═O)$NH_2$, 4, 5-$OCH_2O$—, —$CH_2$(Halo), —CH$(Halo)_2$, —$C(Halo)_3$, —O($C_1$-$C_6$ alkyl) (e.g., —$OCH_3$), —NH($C_1$-$C_6$ alkyl), —S($C_1$-$C_6$ alkyl), —OC(═O)($C_1$-$C_6$ alkyl), —NHC(═O)($C_1$-$C_6$ alkyl), —C(═O)O($C_1$-$C_6$ alkyl) (e.g., —C(O)$OCH_3$), —C(═O)($C_1$-$C_6$ alkyl), —C(═O)O($C_1$-$C_6$ alkyl), —C(═O)NH($C_1$-$C_6$ alkyl), —$CH_2$—$NHZ_3$, —$NHZ_4$, —$C_2$-$C_{10}$ alkenyl, —$C_2$-$C_{10}$ alkynyl, —$C_{10}$ alkyl (e.g., $C_{1-4}$ alkyl), and

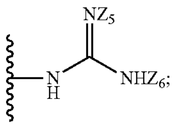

$X_7$, $X_8$, $X_9$, $X_{10}$, and $X_1$ are independently selected from the group consisting of —H, —$N_3$, -Halo (e.g., Cl, Br, F, I), —$NO_2$, —CN, —OH, —SH, —C(═O)OH, —C(═O)H, —C(═O)$NH_2$, —$CH_2$(Halo), —CH$(Halo)_2$, —C$(Halo)_3$, —O($C_1$-$C_6$ alkyl) (e.g., —$OCH_3$), —NH($C_1$-$C_6$ alkyl), —$CH_2$—$NHZ_7$, —$NHZ_8$, —S($C_1$-$C_6$ alkyl), —OC(═O)($C_1$-$C_6$ alkyl), —NHC(═O)($C_1$-$C_6$ alkyl), —C(═O)O($C_1$-$C_6$ alkyl), —C(═O)($C_1$-$C_6$ alkyl), —C(═O)NH($C_1$-$C_6$ alkyl), —$C_2$-$C_{10}$ alkenyl, —$C_2$-$C_{10}$ alkynyl, —$C_1$-$C_{10}$ alkyl (e.g., $C_{1-4}$ alkyl),

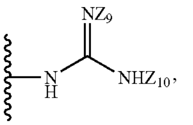

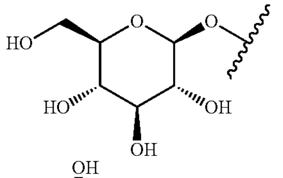

and

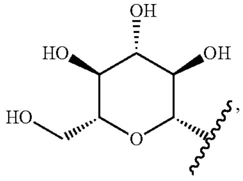

wherein $Z_1$, $Z_2$, $Z_3$, $Z_4$, $Z_5$, $Z_6$, $Z_7$, $Z_8$, $Z_9$, and $Z_{10}$ are independently selected from —H or a nitrogen protecting group;

or a salt thereof.

In some embodiments of the invention, the a nitrogen protecting group is selected from, but not limited to, a carbobenzyloxy (Cbz) group, a p-methoxybenzyl carbonyl (Moz or MeOZ) group, a tert-butyloxycarbonyl (BOC) group, a 9-fluorenylmethyloxycarbonyl (FMOC) group, an acetyl (Ac) group, a benzoyl (Bz) group, a benzyl (Bn) group, a carbamate group, a p-methoxybenzyl (PMB) group, a 3,4-dimethoxybenzyl (DMPM) group, a p-methoxyphenyl (PMP) group, a tosyl (Ts) group, a troc (trichloroethyl chloroformate) group, and a sulfonamide (e.g., Nosyl or Nps) group;

In some embodiments of the invention, the compound of formula (I) is a compound, wherein $Z_1$, $Z_2$, $Z_3$, $Z_4$, $Z_5$, $Z_6$, $Z_7$, $Z_8$, $Z_9$, and $Z_{10}$ are independently selected from the group consisting of —H, -Boc and -Ts.

In some embodiments of the invention, the compound of formula (I) is a compound, wherein W is selected from the group consisting of —H, —$N_3$, -Halo, —$NH_2$, —$NO_2$, —$OCH_3$ and

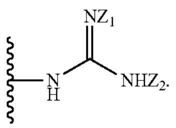

In some embodiments of the invention, the compound of formula (I) is a compound, wherein $Y_1$, $Y_2$, $Y_3$, $Y_4$, and $Y_5$ are independently selected from the group consisting of —H, —$OCH_3$, —OH, —$N_3$, —$NO_2$, -Halo, —$C_{1-4}$ alkyl, —$CH_2$—$NHZ_3$, —$NHZ_4$, —C(═O)$NH_2$, —C(═O)OH, —C(═O)$OCH_3$,

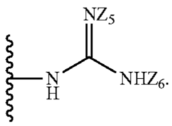

In some embodiments of the invention, the compound of formula (I) is a compound, wherein $X_7$, $X_8$, $X_9$, $X_{10}$, and $X_{11}$ are independently selected from the group consisting of —H, —$OCH_3$, —OH, —$N_3$, —$NO_2$, -Halo, $C_{1-4}$ alkyl, —$CH_2$—$NHZ_7$, —$NHZ_8$, —C(═O)$NH_2$, —C(═O)OH, —C(═O)$OCH_3$,

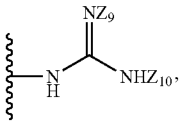

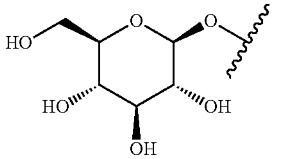

and

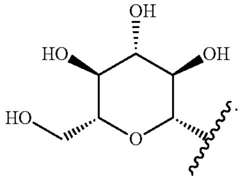

In some embodiments of the invention, the compound of formula (I) is a compound is selected from the group consisting of:

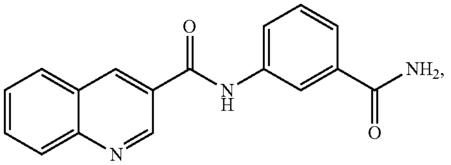

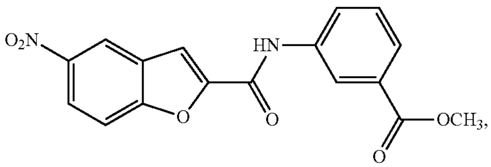

and

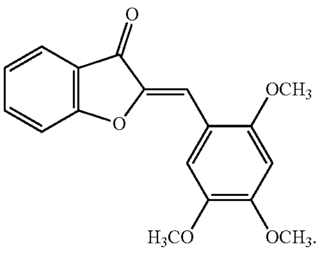

In some embodiments of the invention, the compound of formula (I) is compound:

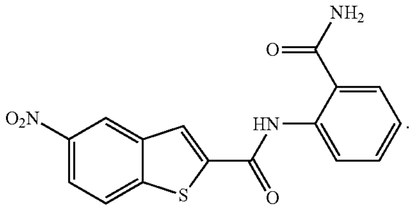 [SMILES: NC(=O)c1ccccc1NC(=O)c1cc2cc([N+](=O)[O-])ccc2s1]

In some embodiments of the invention, the compound of formula (I) is a compound, wherein the salt is a fluoride salt or a chloride salt.

In some embodiments of the invention, the compound of formula (I) is a compound, wherein the salt is a pharmaceutically acceptable salt.

In some embodiments of the invention, the compound of formula (I) is a compound selected from the group consisting of

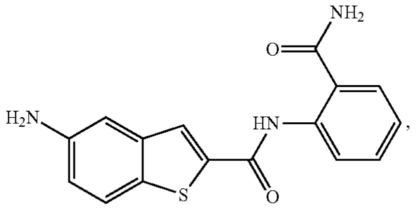

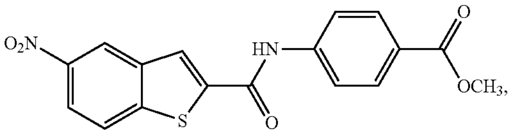

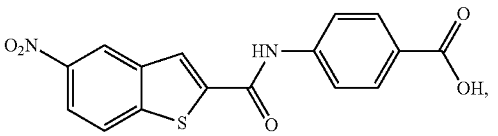

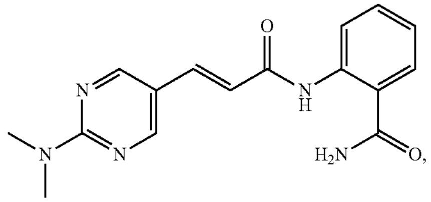

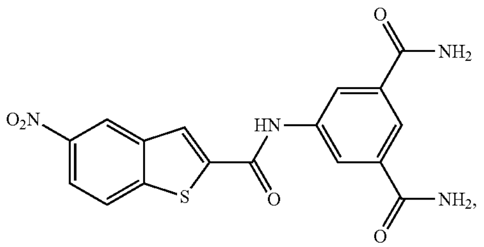

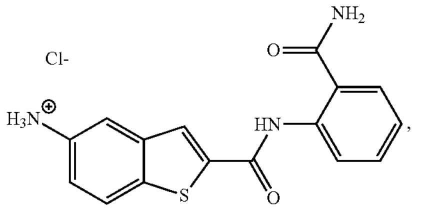

and

-continued

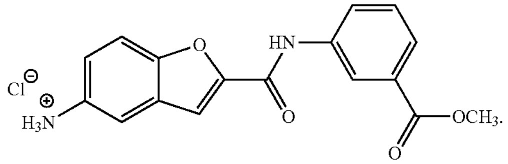

In an embodiment of the invention, a compound inhibiting Gtf and/or biofilm formation is a compound of formula (II):

(II)

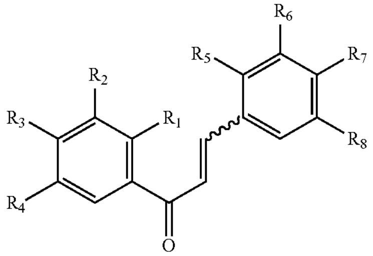

wherein:

$R_1$, $R_2$, $R_3$, and $R_4$ are independently selected from the group consisting of —H, —$N_3$, —Halo (e.g., Cl, Br, F, I), 4, 5-$OCH_2O$—, —$NH_2$, —$NO_2$, —CN, —OH, —SH, —C(═O)OH, —C(═O)H, —C(═O)NH, —$CH_2$(Halo), —CH$(Halo)_2$, —C$(Halo)_3$, —O($C_1$-$C_6$ alkyl) (e.g., —$OCH_3$), —NH($C_1$-$C_6$ alkyl), —$CH_2$—$NHZ_1$, —$NHZ_{12}$, —S($C_1$-$C_6$ alkyl), —OC(═O)($C_1$-$C_6$ alkyl), —NHC(═O)($C_1$-$C_6$ alkyl), —C(═O)O($C_1$-$C_6$ alkyl), —C(═O)($C_1$-$C_6$ alkyl), —C(═O)NH($C_1$-$C_6$ alkyl), —$C_2$-$C_{10}$ alkenyl, —$C_2$-$C_{10}$ alkynyl, —$C_1$-$C_{10}$ alkyl (e.g., $C_1$ alkyl),

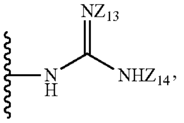

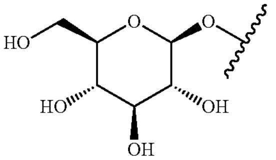

and

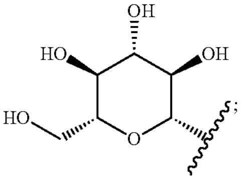

$R_5$, $R_6$, $R_7$, and $R_8$ are independently selected from the group consisting of —H, —$N_3$, -Halo (e.g., Cl, Br, F, I), —$NO_2$, —CN, —OH, —SH, —C(═O)OH, —C(═O)H, —C(═O)$NH_2$, —$CH_2$(Halo), —CH$(Halo)_2$, —C$(Halo)_3$, —O($C_1$-$C_6$ alkyl) (e.g., —$OCH_3$), —NH($C_1$-$C_6$ alkyl), —S($C_1$-$C_6$ alkyl), —OC(═O)($C_1$-$C_6$ alkyl), —NHC(═O)($C_1$-$C_6$ alkyl), —C(═O)O($C_1$-$C_6$ alkyl) (e.g., —C(O)$OCH_3$), —C(═O)($C_1$-$C_6$ alkyl), —C(═O)O($C_1$-$C_6$ alkyl), —C(═O)NH($C_1$-$C_6$ alkyl), —$CH_2$—$NHZ_{15}$, —$NHZ_{16}$—$C_2$-$C_{10}$ alkenyl, —$C_2$-$C_{10}$ alkynyl, —$C_{1-10}$ alkyl (e.g., $C_{1-4}$ alkyl), and

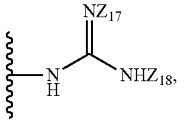

wherein $Z_{11}$, $Z_{12}$, $Z_{13}$, $Z_{14}$, $Z_{15}$, $Z_{16}$, $Z_{17}$ and $Z_{18}$ are independently selected from —H or a nitrogen protecting group;

or a salt thereof.

In some embodiments of the invention, the a nitrogen protecting group is selected from, but not limited to, a carbobenzyloxy (Cbz) group, a p-methoxybenzyl carbonyl (Moz or MeOZ) group, a tert-butyloxycarbonyl (BOC) group, a 9-fluorenylmethyloxycarbonyl (FMOC) group, an acetyl (Ac) group, a benzoyl (Bz) group, a benzyl (Bn) group, a carbamate group, a p-methoxybenzyl (PMB) group, a 3,4-dimethoxybenzyl (DMPM) group, a p-methoxyphenyl (PMP) group, a tosyl (Ts) group, a troc (trichloroethyl chloroformate) group, and a sulfonamide (e.g., Nosyl or Nps) group In some embodiments of the invention, the compound of formula (II) is a compound, wherein $Z_{11}$, $Z_{12}$, $Z_{13}$, $Z_{14}$, $Z_{15}$, $Z_{16}$, $Z_{17}$ and $Z_{18}$ are independently selected from the group consisting of —H, -Boc and -Ts.

In some embodiments of the invention, the compound of formula (II) is a compound wherein $R_1$, $R_2$, $R_3$, and $R_4$ are independently selected from the group consisting of —H, —OH, —OMe, —$NMe_2$, and 4, 5-$OCH_2O$—.

In some embodiments of the invention, the compound of formula (II) is a compound wherein $R_5$, $R_6$, $R_7$, and $R_8$ are independently selected from the group consisting of —H, —OH, —OMe, and -Halo.

In some embodiments of the invention, the compound of formula (II) is a compound wherein at least 2 R groups selected from $R_5$, $R_6$, $R_7$, and $R_8$ are —OH.

In some embodiments of the invention, the compound of formula (II) is a compound wherein $R_7$ is not —H.

In some embodiments of the invention, the compound of formula (II) is a compound wherein, $R_7$ is —OH, and $R_5$ or $R_6$ is —OH.

In some embodiments of the invention, the compound of formula (II) is a compound, wherein $R_1$ is —OH, and $R_2$ and $R_3$ are —OH or —OMe.

In some embodiments of the invention, the compound of formula II is not a compound wherein $R_7$ is —OMe and $R_6$ is —OH, and $R_3$ and $R_4$ are —OMe or —$OCH_2O$—; or $R_3$ is —OH, and $R_2$ and $R_4$ are —$NMe_2$; or $R_1$ and $R_4$ are —OH; or $R_6$ and $R_8$ are —OMe, and $R_3$ is —OH.

In some embodiments of the invention, the compound of formula II is not a compound wherein $R_5$ is —OH, and $R_3$ is —OH— and $R_4$ is OMe; or $R_1$ and $R_3$ are —OH; or $R_7$ and $R_2$ are —OH; or $R_2$ is OH and $R_6$ and $R_8$ are —$C_1$ or —H.

In some embodiments of the invention, the compound of formula II is not a compound wherein $R_1$ is —OH and $R_7$ is —OH and $R_6$ is —OMe or —H; or $R_6$ or $R_3$ is OH; or $R_5$, $R_7$, and $R_8$ are —OH.

In some embodiments of the invention, the compound of formula (II) is

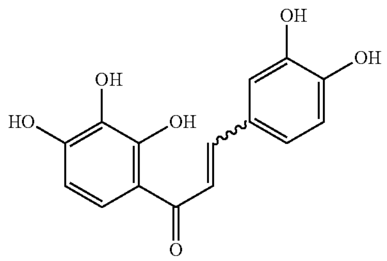

or

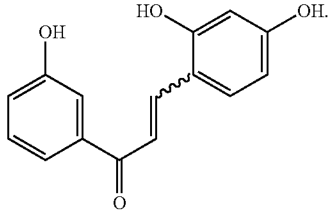

In some embodiments of the invention, the compound of formula (II) is

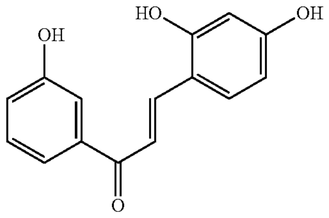

or

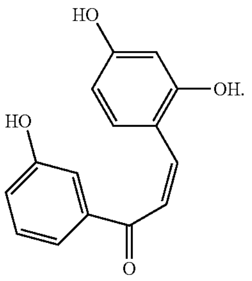

In an embodiment of the invention, a compound inhibiting Gtf and/or biofilm formation is a compound of formula IA or IB:

IA

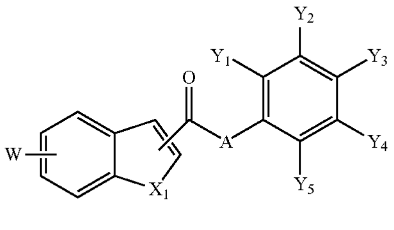

or

-continued

IB

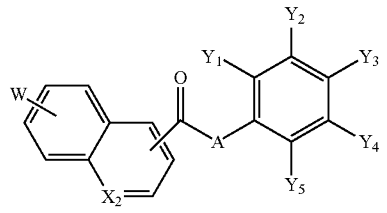

or a salt thereof.

In some embodiments of the invention, the compound of formula IA or IB is selected from the group consisting of:

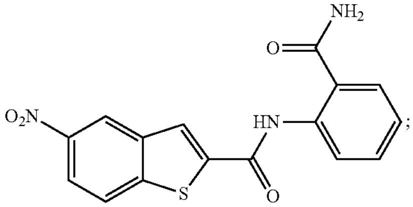
;
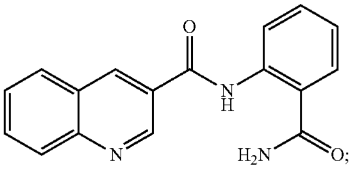
;
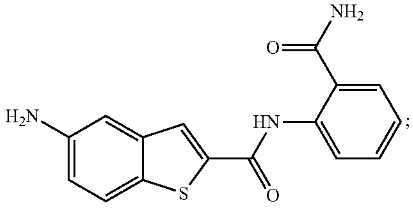
;
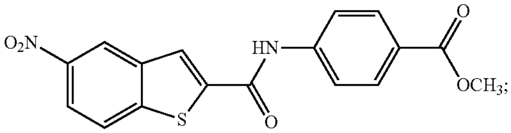
;
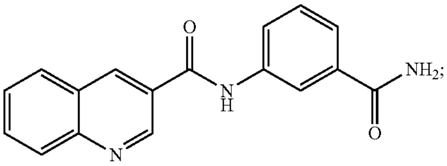
; and
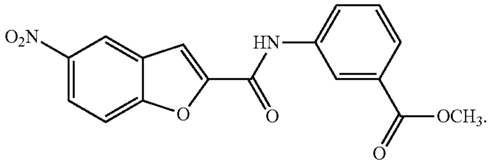
.

In some embodiments of the invention, a compound inhibiting Gtf and/or biofilm formation is a compound selected from the group consisting of:

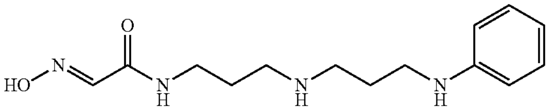
;

-continued

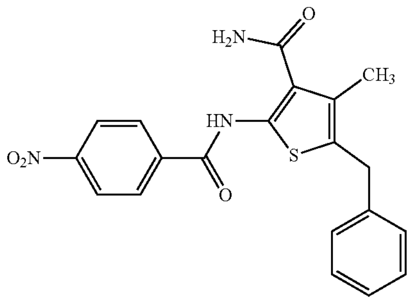
;
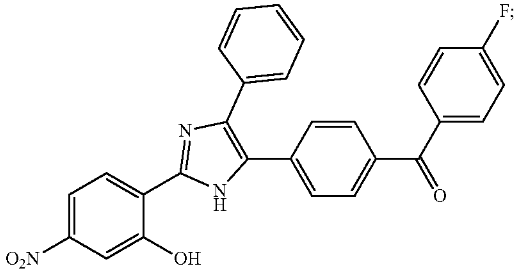
;
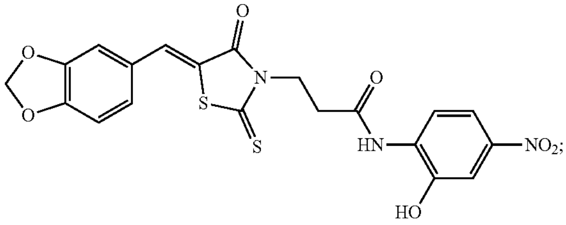
;
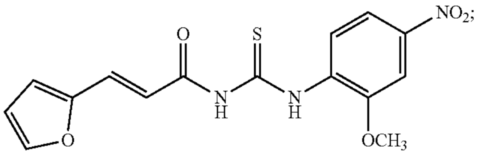
; and
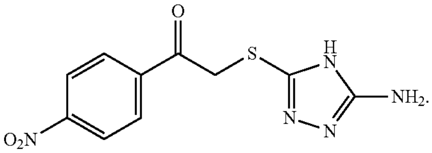
.

In some embodiments of the invention, the compound inhibiting Gtf and/or biofilm formation is selected from the group consisting of:

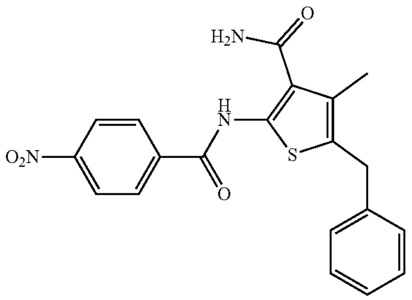
;

-continued

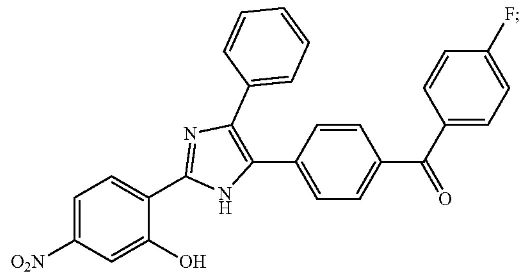

; and

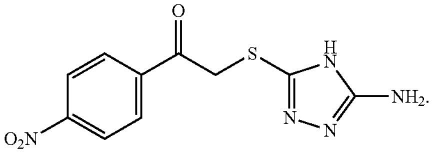

Unless otherwise stated, structures depicted herein are meant to include all geometric (or conformational) forms of the structure; for example, (Z) and (E) double bond isomers, and (Z) and (E) conformational isomers. Therefore, single geometric (or conformational) isomers as well as mixtures of the present compounds are within the scope of the invention.

In other embodiments of the invention, provided are compositions, pharmaceutical compositions, and pharmaceutical formulations comprising a therapeutically effective amount of the compounds of the present invention. In other embodiments, the composition, pharmaceutical composition or pharmaceutical formulation further comprises a pharmaceutically acceptable carrier. The term "pharmaceutically acceptable carrier" as used herein refers to any substance, not itself a therapeutic agent, used as at least in part as a vehicle for delivery of a therapeutic agent to a subject. Non-limiting examples of pharmaceutically acceptable components include, without limitation, any of the standard pharmaceutical carriers such as phosphate buffered saline solutions, water, emulsions such as oil/water emulsions or water/oil emulsions, microemulsions, and various types of wetting agents. Further, in preparing such pharmaceutical compositions comprising the active ingredient or ingredients in admixture with components necessary for the formulation of the compositions, other conventional pharmacologically acceptable additives may be incorporated, for example, excipients, stabilizers, wetting agents, emulsifying agents, lubricants, sweetening agents, coloring agents, flavoring agents, isotonicity agents, buffering agents, antioxidants and the like. Additives may include, for example, starch, mannitol, sorbitol, precipitated calcium carbonate, crystalline cellulose, carboxymethylcellulose, dextrin, gelatin, acacia, EDTA, magnesium stearate, tale, hydroxypropylmethylcellulose, sodium metabisulfite, and the like.

Formulations suitable for administering the compounds and compositions of the present invention may be suitable for oral or buccal (sublingual) administration. The formulation may either be in the form of a solid or a liquid. In some embodiments, forms of formulations suitable for oral administration of the compounds and compositions of the present invention include, but are not limited to, a tooth paste or dentifrice composition, an oral hygiene product, for example, an oral hygiene tablet, an oral care composition, for example, an oral rinse (e.g., a mouth wash), a gel or an additive to a digestible product. Formulations suitable for buccal (sub-lingual) administration include lozenges, tablets, capsules, chewing gum and the like, comprising the active compound, with suitable carriers and additives that would be appreciated by one of skill in the art, for example, binders, diluents, lubricants, disintegrating agents and the like.

Formulations for the prevention of denture plaques may include liquid solutions and/or rinses, either when worn by a subject, or when removed and not being worn by the subject, for example, a solution or rinse for soaking the dentures for a period of time therein.

Liquid formulations include, but are not limited to, solutions, emulsions, dispersions, suspensions and the like with suitable carriers. Additives may include water, alcohols, oils, glycols, preservatives and the like.

In some embodiments, formulations suitable for administering the compounds and compositions of the present invention may also include additives that may provide greater patient compliance, for example, coloring agents, flavoring agents and the like.

In some other embodiments, the formulations for administering the compounds and compositions of the present invention may further comprise an additional agent or agents. Such agents may include, but are not limited to, agents for removing plaque, whitening and/or remineralizing teeth, and the like. In still other embodiments, the formulation may further comprise a delivery system, for example, a film or a strip of material, which can be placed against the surface of the teeth of the subject in order to deliver the formulation, for example, as set forth in U.S. Pat. Nos. 5,989,569 and 6,045,811.

Subjects suitable to be treated with the compounds, compositions and formulations of the present invention include, but are not limited to mammalian subjects. Mammals according to the present invention include, but are not limited to, canines, felines, bovines, caprines, equines, ovines, porcines, rodents (e.g., rats and mice), lagomorphs, primates, humans and the like, and mammals in utero. Any mammalian subject in need of being treated or desiring treatment according to the present invention is suitable. Human subjects of any gender (for example, male, female or transgender) and at any stage of development (i.e., neonate, infant, juvenile, adolescent, adult, or elderly) may be treated according to the present invention.

The method of administration of the compound, pharmaceutical composition or pharmaceutical formulation as described herein is not particularly limited, and any method of administration may be used that would be appreciated by one of skill in the art for the compound, pharmaceutical composition or pharmaceutical formulation as described herein. Non-limiting examples of methods of administration include direct application to the teeth e.g., via brushing, spraying, painting, and/or rinsing (e.g., a mouth wash), and/or application into a container (e.g., a mouth guard and/or other dental mold) which may then be placed in contact with the teeth. The method of administration of the compound, pharmaceutical composition or pharmaceutical formulation may be applied at a medical facility by a clinician (e.g., a dentist, orthodontist, and/or dental hygienist), and/or may be applied at home (e.g., self-applied by a subject). The schedule of administration of the compound, pharmaceutical composition or pharmaceutical formulation as described herein is not particularly limited, and any schedule of administration may be used that would be appreciated by one of skill in the art for the compound, pharmaceutical composition or pharmaceutical formulation as described herein. In some embodiments, a schedule of administration that is suitable by one of skill in the art may be multiple times a day (e.g., 2, 3, 4, or 5 times) or once a day. In some embodiments, a schedule of administration that is suitable by one of skill in the art may be multiple times a week (e.g., 2, 3, 4, 5, 6, 7, 8, 9, 10, 11, 12, 13 or 14 times) or once a week. In some embodiments, a schedule of administration that is suitable by one of skill in the art may be multiple times a month (e.g., 2, 3, 4, 5, 6, 7, 8, 9, 10, 11, 12, 13, 14, 15, 16, 17, 18, 19 or 20 times) or once a month. In some embodiments, a schedule of administration that is suitable by one of skill in the art may be multiple times a year (e.g., 1, 2, 3, 4, 5, or 6 times a year) or once a year (e.g., at routine dentist visits). In some embodiments, a compound, pharmaceutical composition or pharmaceutical formulation as described herein may be applied to all teeth, some teeth, and/or one or more tooth having a cavity and/or filling. In some embodiments, application of a compound, pharmaceutical composition or pharmaceutical formulation as described herein may begin (e.g., may be indicated) before a cavity is found, after a cavity is found, and/or in subjects susceptible to cavities (e.g., children (e.g., under age 18, 17, 16, 15, 14, 13, or 12), subjects with poor oral hygiene, subjects with increased genetic and/or environmental susceptibility to cavities).

In other embodiments of the invention, provided are methods of inhibiting biofilm formation in a subject in need thereof, comprising administering to the subject of an effective amount of the compound, composition or pharmaceutical formulation of the invention, thereby inhibiting biofilm formation. Biofilm formation may be inhibited by at least about 10%, e.g., at least about 20%, 30%, 40%, 50%, 60%, 70%, 80%, 90%, 95%, or 99%, relative to a subject in the absence of the method of the invention.

In other embodiments of the invention, provided are methods of preventing, inhibiting and/or treating the formation of dental caries in a subject in need thereof comprising administering to the subject of an effective amount of the compound, composition, or pharmaceutical formulation of the invention thereby preventing, inhibiting and/or treating the formation of dental caries. Dental caries formation may be inhibited by at least about 10%, e.g., at least about 20%, 30%, 40%, 50%, 60%, 70%, 80%, 90%, 95%, or 99%, relative to a subject in the absence of the method of the invention.

In other embodiments of the invention, provided are methods of preventing, inhibiting and/or treating the formation of denture plaques in a denture of a subject in need thereof comprising contacting the denture with an effective amount of the compound, composition, or pharmaceutical formulation of the invention thereby inhibiting and/or treating the formation of denture plaques. In some embodiments, the denture is contacted while in the subject. Denture plaque formation may be inhibited by at least about 10%, e.g., at least about 20%, 30%, 40%, 50%, 60%, 70%, 80%, 90%, 95%, or 99%, relative to a subject in the absence of the method of the invention.

Methods of identifying a compound that can inhibit *Streptococcus*-mediated biofilm formation may include determining and/or screening the ability of a compound to bind and/or inhibit the activity of Gtfs. Gtfs include GtfA, GtfB, GtfC and GtfD. In some embodiments, the Gtf is GtfC. In some embodiments, the determining and/or screening may include utilization of 3D structures of the Gtf, for example, the GtfC catalytic domain, complexed with a compound and/or inhibitor of Gtf, for example, acarbose. In some embodiments, the screening may be an in silico method, which include steps implemented by a computer and/or computer program products to screen and/or predict binding affinities of a compound to Gtf, including analog and/or digital hardware, and/or computer program instructions. For example, a computer program, such as, but not limited to, FlexX/LeadIT, may be used for the in silico screening of a compound that may bind to the Gtf catalytic domain using the 3D structure of, for example, GtfC complexed with acarbose. These computer program instructions may be provided to a processor of a general purpose computer, special purpose computer, Application Specific Integrated Circuits (ASIC), and/or other programmable data processing apparatus, such that the instructions, which execute via the processor of the computer and/or other programmable data processing apparatus, create means for implementing the functions/acts specified. Other software, such as an operating system, also may be included.

The present invention is more particularly described in the following examples that are intended as illustrative only since numerous modifications and variations therein will be apparent to those skilled in the art.

Example 1

Table 1 lists the $IC_{50}$ for *S. mutans* biofilm inhibition for various compounds selected by in silico screening. Biofilm assays using 96-well flat-bottom polystyrene microtiter plates were performed to evaluate *S. mutans* biofilm formation at various conditions as described (Liu et al. (2011) *Antimicrobial Agents and Chemotherapy* 55, 2679; Zhang et al. (2015) *International Journal of Antimicrobial Agents* 46, 174), the disclosures of which are incorporated herein by reference in their entirety). Each assay was replicated three times. Compounds that inhibited biofilm formation at minimum concentration (MBIC) were determined by serial dilutions.

TABLE 1

Biofilm inhibitory activity of compounds

| Code | Structure | Notebook | Biofilm Inhibition $IC_{50}$ (μM)[a] |
|---|---|---|---|
| 3A | 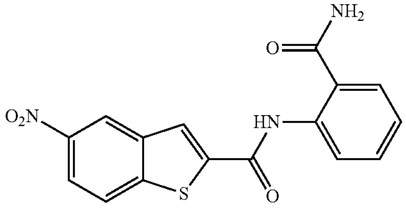 [SMILES: NC(=O)c1ccccc1NC(=O)c1cc2cc([N+](=O)[O-])ccc2s1] | SN-I-204 | 16.7 |

TABLE 1-continued
Biofilm inhibitory activity of compounds
| Code | Structure | Notebook | Biofilm Inhibition $IC_{50}$ (μM)[a] |
| --- | --- | --- | --- |
| 3B | 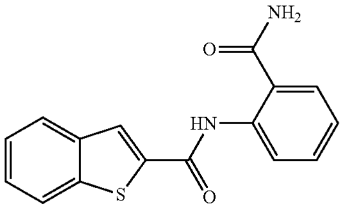 [SMILES: NC(=O)c1ccccc1NC(=O)c1cc2ccccc2s1] | SN-I-201 | 45.6 |
| 3C | 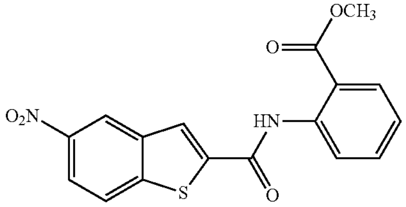 [SMILES: COC(=O)c1ccccc1NC(=O)c1cc2cc([N+](=O)[O-])ccc2s1] | SN-I-211 | >500[b] |
| 3D | 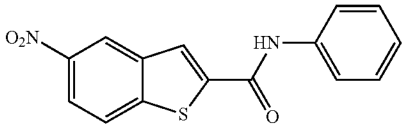 | SN-I-209 | >500[b] |
| 3E | 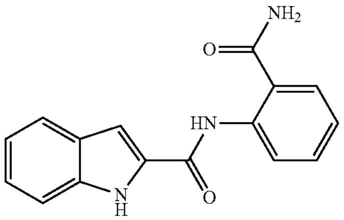 [SMILES: NC(=O)c1ccccc1NC(=O)c1cc2ccccc2[nH]1] | SN-I-202 | >500[b] |
| 3F | 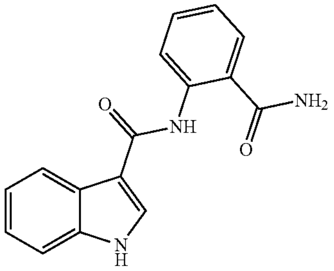 [SMILES: NC(=O)c1ccccc1NC(=O)c1c[nH]c2ccccc12] | SN-I-203 | 145.5 |
| 3G | 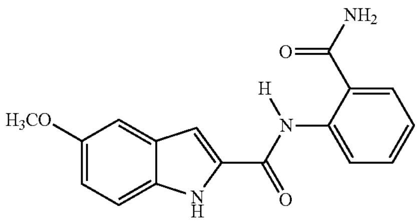 [SMILES: COc1ccc2[nH]c(C(=O)Nc3ccccc3C(N)=O)cc2c1] | SN-I-205 | 68.8 |

TABLE 1-continued
Biofilm inhibitory activity of compounds
| Code | Structure | Notebook | Biofilm Inhibition $IC_{50}$ (μM)[a] |
|---|---|---|---|
| 3H | 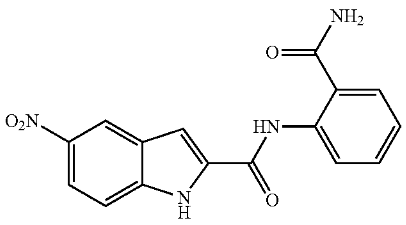 [SMILES: NC(=O)c1ccccc1NC(=O)c1cc2cc([N+](=O)[O-])ccc2[nH]1] | SN-I-208 | >500[b] |
| 3I | 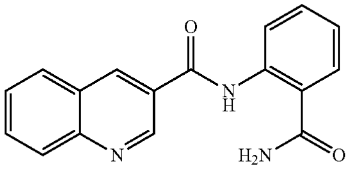 | SN-I-199 | 15.3 |
| 3J | 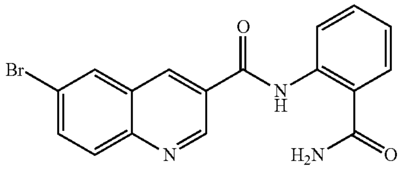 [SMILES: NC(=O)c1ccccc1NC(=O)c1cnc2ccc(Br)cc2c1] | SN-I-200 | 106.3 |
| 3K | 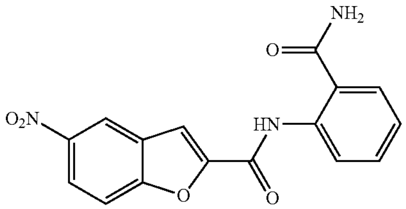 [SMILES: NC(=O)c1ccccc1NC(=O)c1cc2cc([N+](=O)[O-])ccc2o1] | SN-I-207 | 102.7 |
| 3L | 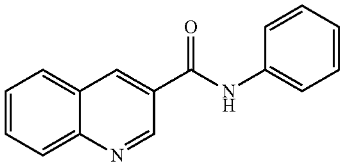 [SMILES: O=C(Nc1ccccc1)c1cnc2ccccc2c1] | SN-I-210 | >500[b] |
| 3M | 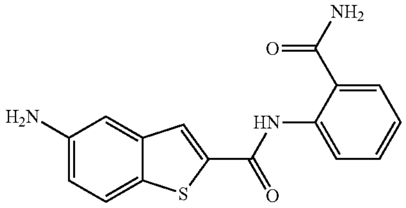 | SN-I-216 | 10.2 |
| 3N | 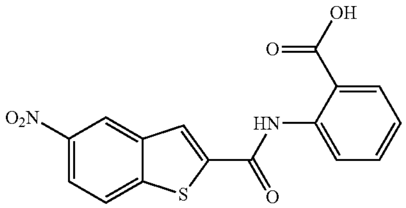 [SMILES: O=C(Nc1ccccc1C(=O)O)c1cc2cc([N+](=O)[O-])ccc2s1] | SN-I-222 | 89.3 |

TABLE 1-continued
| Biofilm inhibitory activity of compounds | | | |
|---|---|---|---|
| Code | Structure | Notebook | Biofilm Inhibition $IC_{50}$ (μM)[a] |
| 3O | 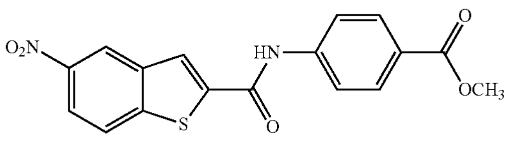 | SN-I-217 | 9.6 |
| 3P | 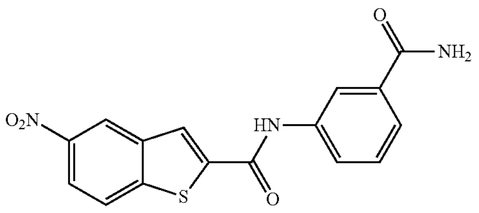 | SN-I-225b | 42.3 |
| 3Q | 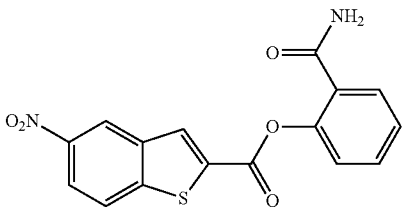 | SN-I-225a | 50.4 |
| 3R | 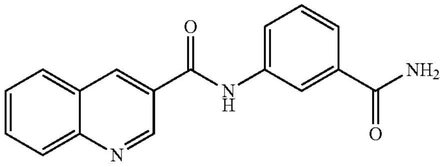 [SMILES: NC(=O)c1cccc(NC(=O)c2cnc3ccccc3c2)c1] | SN-I-225c | 8.6 |
| 3S | 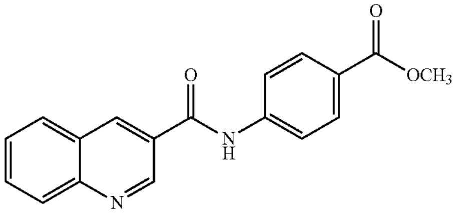 [SMILES: COC(=O)c1ccc(NC(=O)c2cnc3ccccc3c2)cc1] | SN-I-237c | 92.3 |
| 3T | 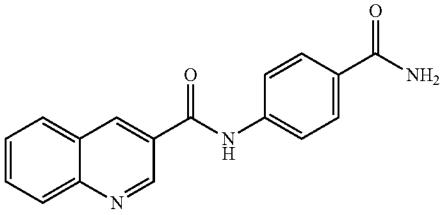 [SMILES: NC(=O)c1ccc(NC(=O)c2cnc3ccccc3c2)cc1] | SN-I-234c | >500[b] |
| 3U | 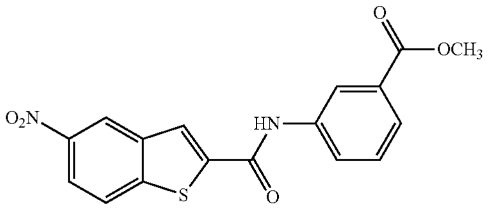 [SMILES: COC(=O)c1cccc(NC(=O)c2cc3cc([N+](=O)[O-])ccc3s2)c1] | SN-I-238a | 54.4 |

TABLE 1-continued
Biofilm inhibitory activity of compounds
| Code | Structure | Notebook | Biofilm Inhibition $IC_{50}$ (μM)[a] |
|---|---|---|---|
| 3V | 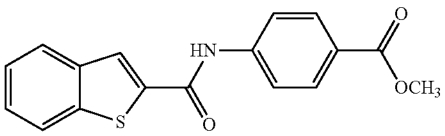 [SMILES: COC(=O)c1ccc(NC(=O)c2cc3ccccc3s2)cc1] | SN-I-237b | 41.2 |
| 3W | 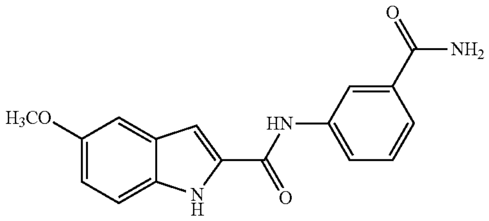 [SMILES: COc1ccc2[nH]c(C(=O)Nc3cccc(C(N)=O)c3)cc2c1] | SN-I-235e | 56.6 |
| 3X | 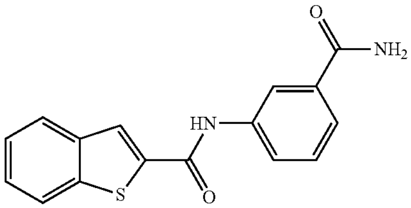 [SMILES: NC(=O)c1cccc(NC(=O)c2cc3ccccc3s2)c1] | SN-I-235b | 115.9 |
| 3Y | 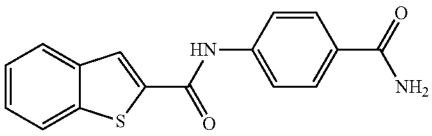 [SMILES: NC(=O)c1ccc(NC(=O)c2cc3ccccc3s2)cc1] | SN-I-234b | 45.6 |
| 3Z | 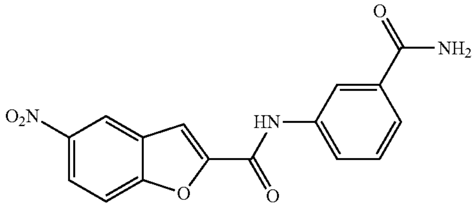 [SMILES: NC(=O)c1cccc(NC(=O)c2cc3cc([N+](=O)[O-])ccc3o2)c1] | SN-I-235d | 38.8 |
| AA | 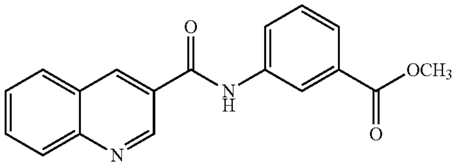 [SMILES: COC(=O)c1cccc(NC(=O)c2cnc3ccccc3c2)c1] | SN-I-238c | 147.3 |
| AB | 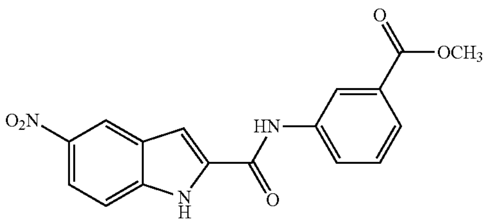 [SMILES: COC(=O)c1cccc(NC(=O)c2cc3cc([N+](=O)[O-])ccc3[nH]2)c1] | SN-I-238f | 31.4 |
| AC | 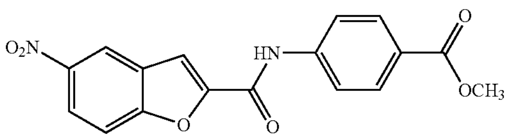 | SN-I-237d | 144.0 |

TABLE 1-continued
| Biofilm inhibitory activity of compounds | | | |
|---|---|---|---|
| Code | Structure | Notebook | Biofilm Inhibition $IC_{50}$ (μM)[a] |
| AD | 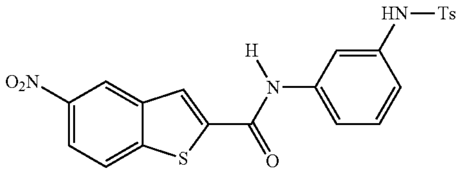 [SMILES: Cc1ccc(S(=O)(=O)Nc2cccc(NC(=O)c3cc4cc([N+](=O)[O-])ccc4s3)c2)cc1] | SN-I-236 | 63.7 |
| AE | 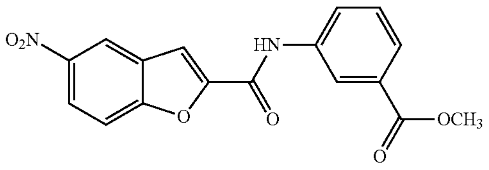 [SMILES: COC(=O)c1cccc(NC(=O)c2cc3cc([N+](=O)[O-])ccc3o2)c1] | SN-I-238d | 2.7 |
| AF | 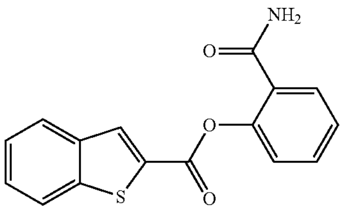 [SMILES: NC(=O)c1ccccc1OC(=O)c1cc2ccccc2s1] | SN-I-259b | >500[b] |
| AG | 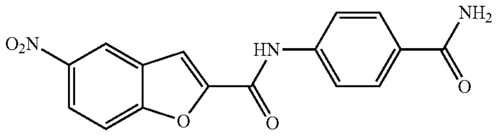 [SMILES: NC(=O)c1ccc(NC(=O)c2cc3cc([N+](=O)[O-])ccc3o2)cc1] | SN-I-234d | 238.7 |
| AH | 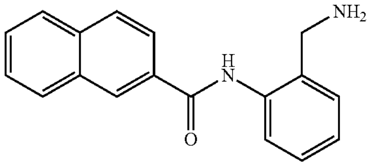 [SMILES: NCc1ccccc1NC(=O)c1ccc2ccccc2c1] | SN-I-248j | 160.1 |
| AI | 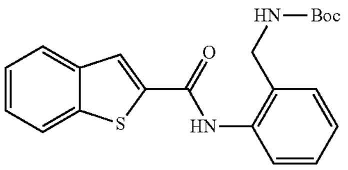 [SMILES: CC(C)(C)OC(=O)NCc1ccccc1NC(=O)c1cc2ccccc2s1] | SN-I-247b | 43.4 |
| AJ | 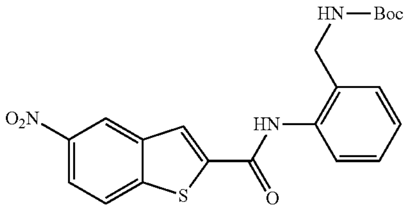 [SMILES: CC(C)(C)OC(=O)NCc1ccccc1NC(=O)c1cc2cc([N+](=O)[O-])ccc2s1] | SN-I-247a | 51.5 |

TABLE 1-continued
| Code | Structure | Notebook | Biofilm Inhibition $IC_{50}$ (μM)[a] |
|---|---|---|---|
| | Biofilm inhibitory activity of compounds | | |
| AK | 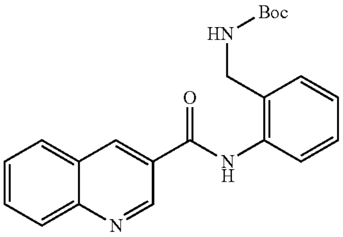 [SMILES: CC(C)(C)OC(=O)NCc1ccccc1NC(=O)c1cnc2ccccc2c1] | SN-I-247c | 52.8 |
| AL | 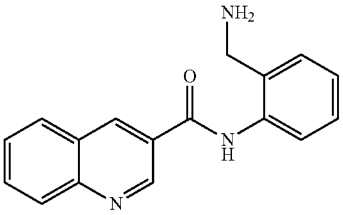 [SMILES: NCc1ccccc1NC(=O)c1cnc2ccccc2c1] | SN-I-248c | 135.6 |
| AM | 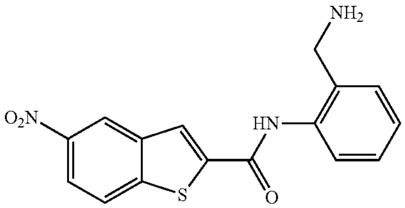 [SMILES: NCc1ccccc1NC(=O)c1cc2cc([N+](=O)[O-])ccc2s1] | SN-I-248a | 106.2 |
| AN | 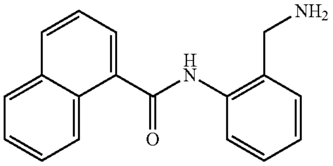 [SMILES: NCc1ccccc1NC(=O)c1cccc2ccccc12] | SN-I-248h | 93.3 |
| AO | 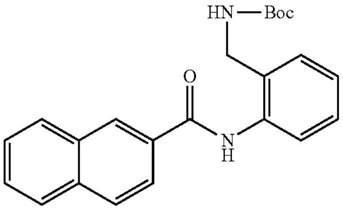 [SMILES: CC(C)(C)OC(=O)NCc1ccccc1NC(=O)c1ccc2ccccc2c1] | SN-I-247j | 56.8 |
| AP | 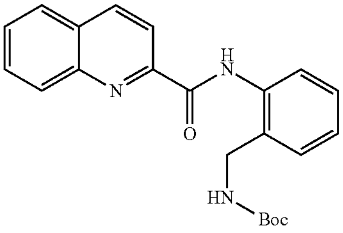 [SMILES: CC(C)(C)OC(=O)NCc1ccccc1NC(=O)c1ccc2ccccc2n1] | SN-I-247l | 67.5 |

TABLE 1-continued
Biofilm inhibitory activity of compounds
| Code | Structure | Notebook | Biofilm Inhibition $IC_{50}$ (μM)[a] |
| --- | --- | --- | --- |
| AQ | 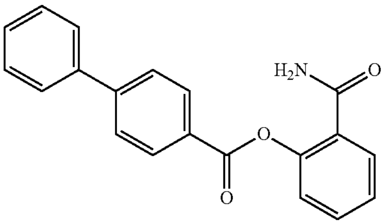 [SMILES: NC(=O)c1ccccc1OC(=O)c1ccc(-c2ccccc2)cc1] | SN-I-243j | 55.6 |
| AR | 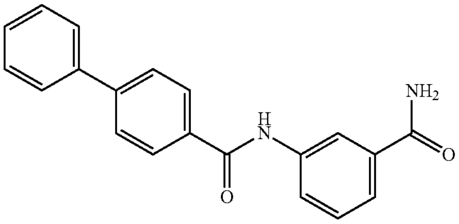 [SMILES: NC(=O)c1cccc(NC(=O)c2ccc(-c3ccccc3)cc2)c1] | SN-I-241j | 79.9 |
| AS | 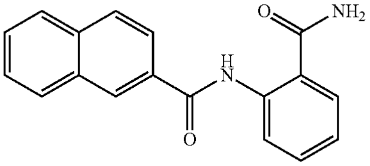 [SMILES: NC(=O)c1ccccc1NC(=O)c1ccc2ccccc2c1] | SN-I-240i | 84.1 |
| AT | 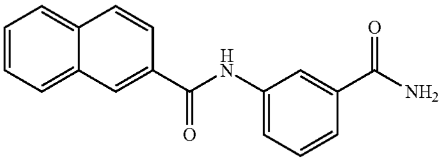 [SMILES: NC(=O)c1cccc(NC(=O)c2ccc3ccccc3c2)c1] | SN-I-241i | 67.7 |
| AU | 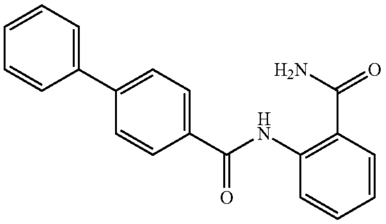 [SMILES: NC(=O)c1ccccc1NC(=O)c1ccc(-c2ccccc2)cc1] | SN-I-240j | >500[b] |
| AV | 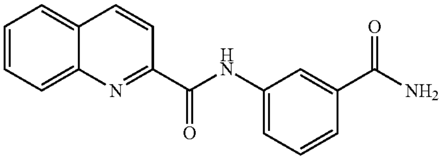 [SMILES: NC(=O)c1cccc(NC(=O)c2ccc3ccccc3n2)c1] | SN-I-241l | 111 |
| AW | 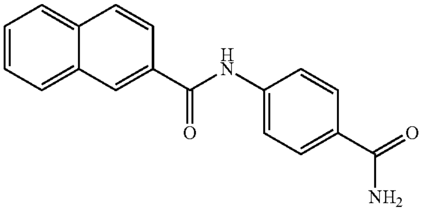 [SMILES: NC(=O)c1ccc(NC(=O)c2ccc3ccccc3c2)cc1] | SN-I-242j | >500[b] |

TABLE 1-continued
Biofilm inhibitory activity of compounds
| Code | Structure | Notebook | Biofilm Inhibition $IC_{50}$ (μM)[a] |
|---|---|---|---|
| AX | 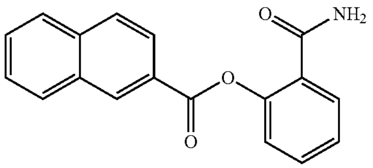 [SMILES: NC(=O)c1ccccc1OC(=O)c1ccc2ccccc2c1] | SN-I-243i | 98.3 |
| AY | 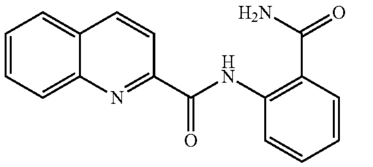 [SMILES: NC(=O)c1ccccc1NC(=O)c1ccc2ccccc2n1] | SN-I-240l | >500[b] |
| AZ | 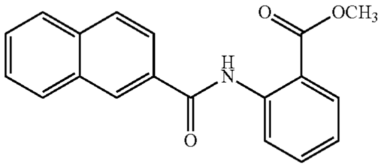 [SMILES: COC(=O)c1ccccc1NC(=O)c1ccc2ccccc2c1] | SN-I-257i | 121.3 |
| BA | 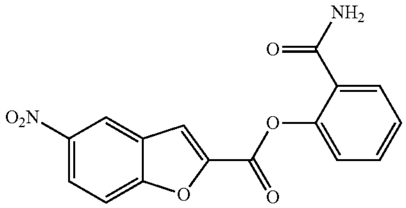 | SN-I-259d | 278.6 |
| BB | 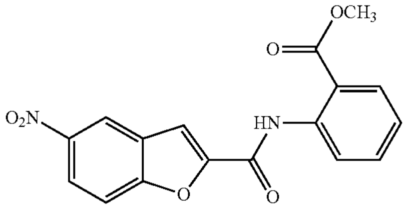 | SN-I-257d | 71.4 |
| BC | 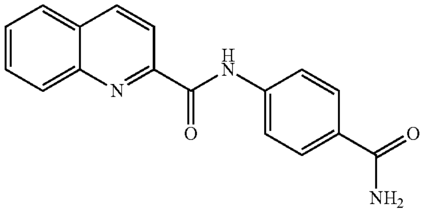 | SN-I-258l | 54.4 |
| BD | 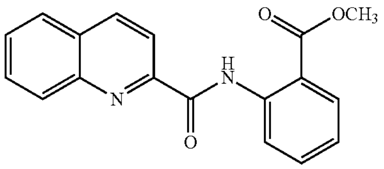 [SMILES: COC(=O)c1ccccc1NC(=O)c1ccc2ccccc2n1] | SN-I-257l | 89.5 |

TABLE 1-continued
| Biofilm inhibitory activity of compounds | | | |
|---|---|---|---|
| Code | Structure | Notebook | Biofilm Inhibition $IC_{50}$ (μM)[a] |
| BE | 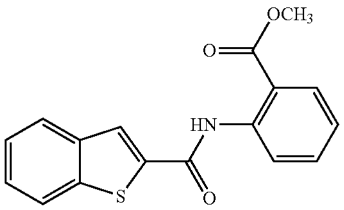 [SMILES: COC(=O)c1ccccc1NC(=O)c1cc2ccccc2s1] | SN-I-257b | 74.9 |
| BF | 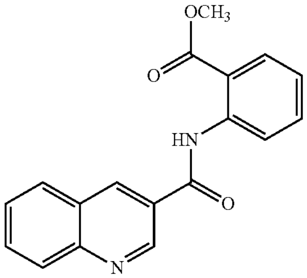 [SMILES: COC(=O)c1ccccc1NC(=O)c1cnc2ccccc2c1] | SN-I-257c | 446.2 |
| BG | 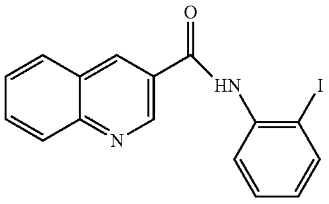 [SMILES: O=C(Nc1ccccc1I)c1cnc2ccccc2c1] | HW-1-151 | >500[b] |
| BH | 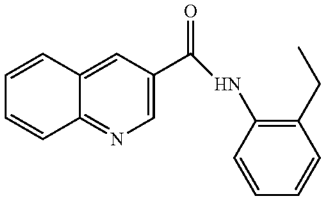 [SMILES: CCc1ccccc1NC(=O)c1cnc2ccccc2c1] | HW-1-159 | 204.2 |
| BI | 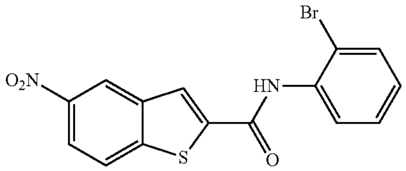 | HW-1-157 | 122.1 |
| BJ | 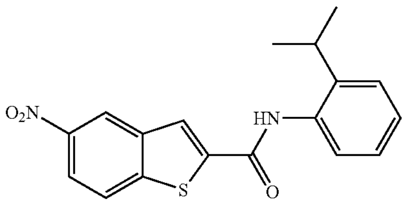 [SMILES: CC(C)c1ccccc1NC(=O)c1cc2cc([N+](=O)[O-])ccc2s1] | HW-1-169 | 262.0 |
| BK | 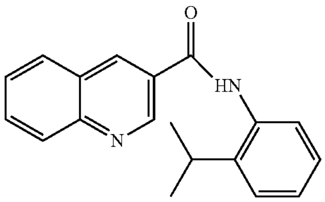 [SMILES: CC(C)c1ccccc1NC(=O)c1cnc2ccccc2c1] | HW-1-162 | >500[b] |

TABLE 1-continued
Biofilm inhibitory activity of compounds
| Code | Structure | Notebook | Biofilm Inhibition $IC_{50}$ (μM)[a] |
|---|---|---|---|
| BL | 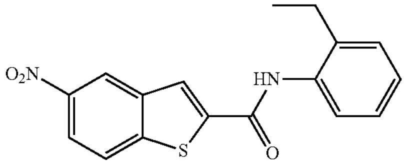 [SMILES: CCc1ccccc1NC(=O)c1cc2cc([N+](=O)[O-])ccc2s1] | HW-1-171 | 157.7 |
| BM | 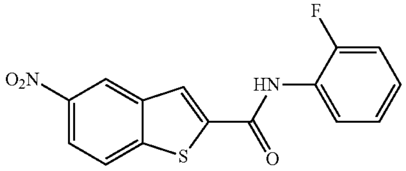 [SMILES: O=C(Nc1ccccc1F)c1cc2cc([N+](=O)[O-])ccc2s1] | HW-1-170 | 162.3 |
| BN | 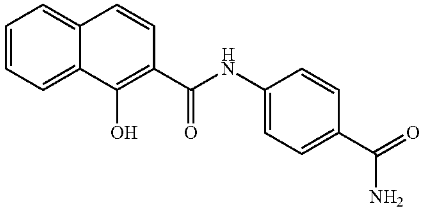 [SMILES: NC(=O)c1ccc(NC(=O)c2ccc3ccccc3c2O)cc1] | SN-I-242g | 56.9 |
| BO | 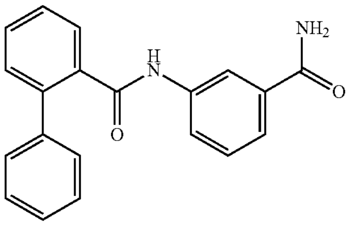 [SMILES: NC(=O)c1cccc(NC(=O)c2ccccc2-c2ccccc2)c1] | SN-I-241k | 49.4 |
| BP | 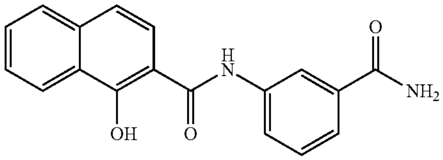 [SMILES: NC(=O)c1cccc(NC(=O)c2ccc3ccccc3c2O)c1] | SN-I-241g | 270.1 |
| BQ | 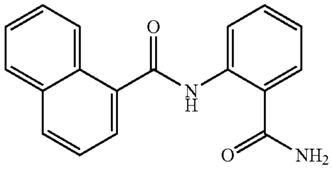 [SMILES: NC(=O)c1ccccc1NC(=O)c1cccc2ccccc12] | SN-I-240h | 445.5 |
| BR | 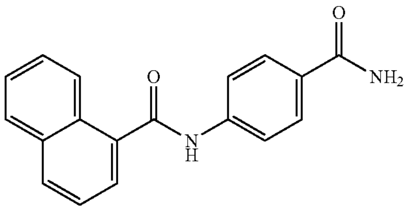 [SMILES: NC(=O)c1ccc(NC(=O)c2cccc3ccccc23)cc1] | SN-I-242h | 167.3 |

TABLE 1-continued

Biofilm inhibitory activity of compounds

| Code | Structure | Notebook | Biofilm Inhibition $IC_{50}$ (μM)[a] |
| --- | --- | --- | --- |
| BS | 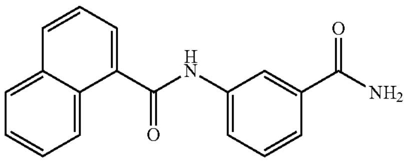 [SMILES: NC(=O)c1cccc(NC(=O)c2cccc3ccccc23)c1] | SN-I-241h | 195.2 |
| BU | 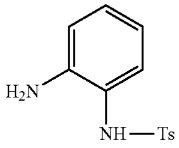 | SN-I-230 | >500[b] |
| BV | 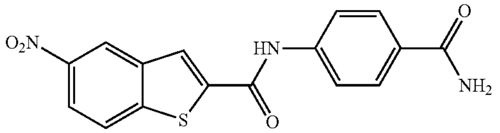 [SMILES: NC(=O)c1ccc(NC(=O)c2cc3cc([N+](=O)[O-])ccc3s2)cc1] | SN-I-258a | 394.9 |
| BW | 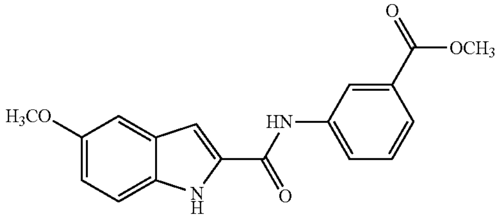 [SMILES: COC(=O)c1cccc(NC(=O)c2cc3cc(OC)ccc3[nH]2)c1] | SN-I-238e | 112.8 |
| BX | 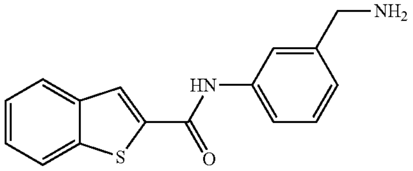 [SMILES: NCc1cccc(NC(=O)c2cc3ccccc3s2)c1] | SN-I-248b | 209.0 |
| BY | 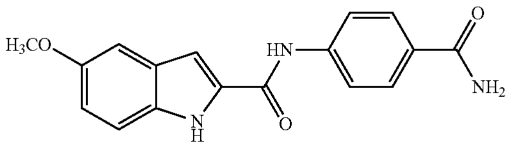 [SMILES: COc1ccc2[nH]c(C(=O)Nc3ccc(C(N)=O)cc3)cc2c1] | SN-I-234e | >500[b] |
| BZ | 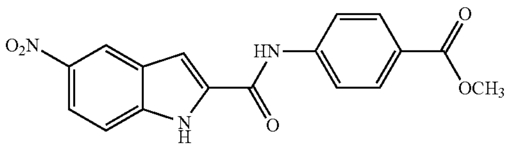 [SMILES: COC(=O)c1ccc(NC(=O)c2cc3cc([N+](=O)[O-])ccc3[nH]2)cc1] | SN-I-237f | 196.1 |
| DMSO | No Compound | DMSO | >500[b] |

[a]Determined by *S. mutans* biofilm inhibition assay.
[b]No inhibition up to 500 μM.

Tables 2, 3 and 4 list the $IC_{50}$ for *S. mutans* biofilm inhibition for additional compounds as well as the $MIC_{50}$ growth inhibition, which was determined according to the experimental procedures provided in Examples 2 and/or 3 and/or 4.

TABLE 2
Biofilm and Growth inhibitory activity of compounds
| Code | Structure | Biofilm Inhibition $IC_{50}$ (μM)[a] | Growth Inhibition $MIC_{50}$ (μM) |
|---|---|---|---|
| SN-I-204 | 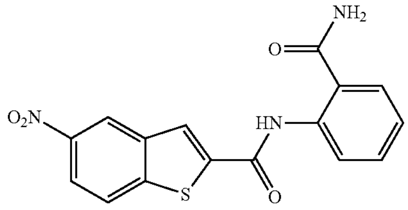 | 16.7 | >300[b] |
| SN-I-201 | 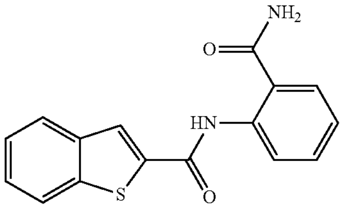 [SMILES: NC(=O)c1ccccc1NC(=O)c1cc2ccccc2s1] | 45.6 | >300[b] |
| SN-I-203 | 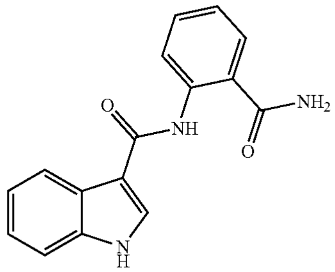 [SMILES: NC(=O)c1ccccc1NC(=O)c1c[nH]c2ccccc12] | 145.5 | >300[b] |
| SN-I-205 | 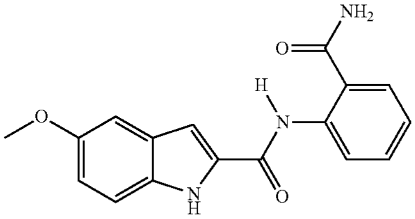 [SMILES: COc1ccc2[nH]c(C(=O)Nc3ccccc3C(N)=O)cc2c1] | 68.8 | >300[b] |
| SN-I-199 | 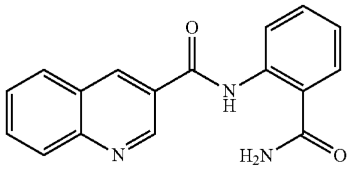 [SMILES: NC(=O)c1ccccc1NC(=O)c1cnc2ccccc2c1] | 15.3 | >300[b] |
| SN-I-200 | 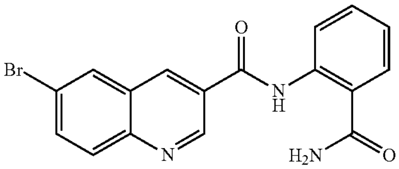 [SMILES: NC(=O)c1ccccc1NC(=O)c1cnc2ccc(Br)cc2c1] | 106.3 | >300[b] |
| SN-I-207 | 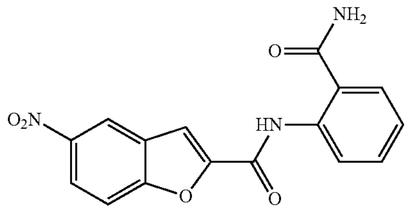 | 102.7 | >300[b] |

TABLE 2-continued
Biofilm and Growth inhibitory activity of compounds
| Code | Structure | Biofilm Inhibition $IC_{50}$ (μM)[a] | Growth Inhibition $MIC_{50}$ (μM) |
| --- | --- | --- | --- |
| SN-I-216 | 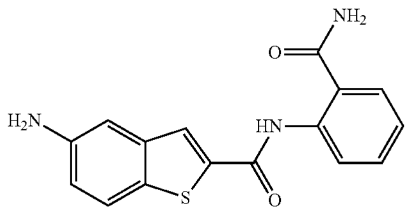 | 10.2 | >300[b] |
| SN-I-222 | 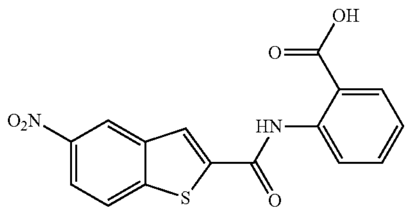 [SMILES: O=C(Nc1ccccc1C(=O)O)c1cc2cc([N+](=O)[O-])ccc2s1] | 89.3 | >300[b] |
| SN-I-217 | 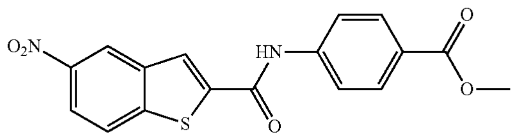 | 9.6 | >300[b] |
| SN-I-225B | 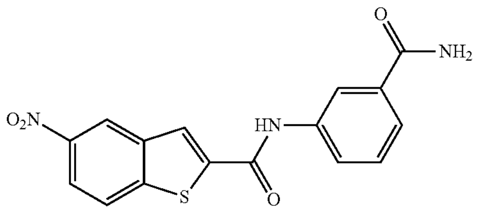 | 42.3 | >300[b] |
| SN-I-225A | 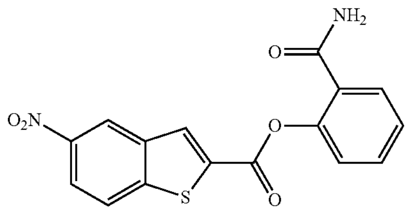 | 50.4 | >300[b] |
| SN-I-225C | 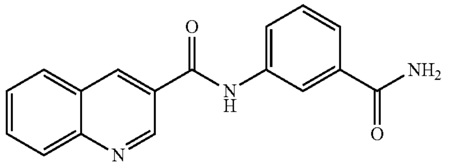 [SMILES: NC(=O)c1cccc(NC(=O)c2cnc3ccccc3c2)c1] | 8.6 | >300[b] |
| SN-I-237C | 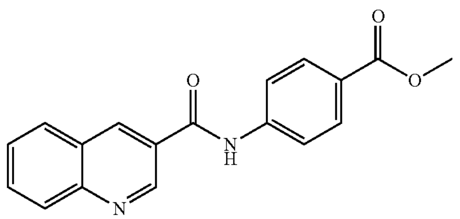 [SMILES: COC(=O)c1ccc(NC(=O)c2cnc3ccccc3c2)cc1] | 92.3 | >300[b] |

TABLE 2-continued
Biofilm and Growth inhibitory activity of compounds
| Code | Structure | Biofilm Inhibition $IC_{50}$ (μM)[a] | Growth Inhibition $MIC_{50}$ (μM) |
|---|---|---|---|
| SN-I-238A | 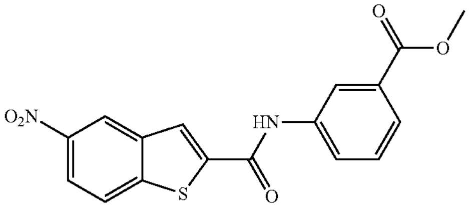 [SMILES: COC(=O)c1cccc(NC(=O)c2cc3cc([N+](=O)[O-])ccc3s2)c1] | 54.4 | >300[b] |
| SN-I-237B | 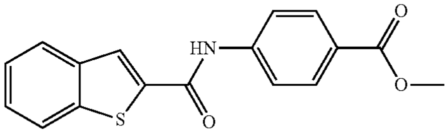 [SMILES: COC(=O)c1ccc(NC(=O)c2cc3ccccc3s2)cc1] | 41.2 | >300[b] |
| SN-I-235E | 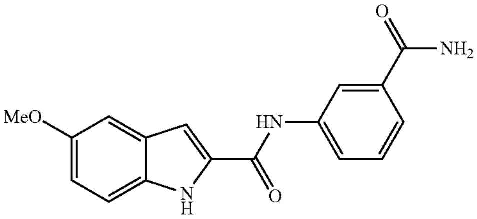 [SMILES: COc1ccc2[nH]c(C(=O)Nc3cccc(C(N)=O)c3)cc2c1] | 56.6 | >300[b] |
| SN-I-235B | 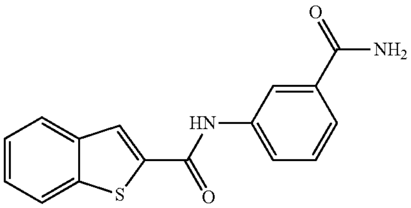 [SMILES: NC(=O)c1cccc(NC(=O)c2cc3ccccc3s2)c1] | 115.9 | >300[b] |
| SN-I-234B | 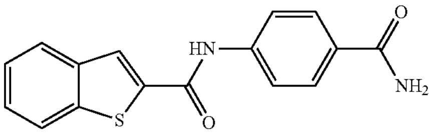 [SMILES: NC(=O)c1ccc(NC(=O)c2cc3ccccc3s2)cc1] | 45.6 | >300[b] |
| SN-I-235D | 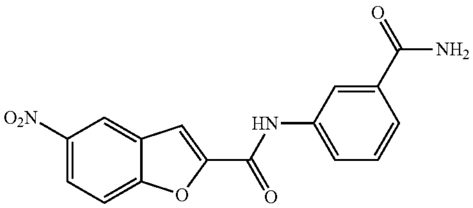 [SMILES: NC(=O)c1cccc(NC(=O)c2cc3cc([N+](=O)[O-])ccc3o2)c1] | 38.8 | >300[b] |
| SN-I-238C | 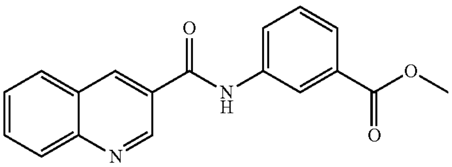 [SMILES: COC(=O)c1cccc(NC(=O)c2cnc3ccccc3c2)c1] | 147.3 | >300[b] |

TABLE 2-continued
Biofilm and Growth inhibitory activity of compounds
| Code | Structure | Biofilm Inhibition $IC_{50}$ (μM)[a] | Growth Inhibition $MIC_{50}$ (μM) |
|---|---|---|---|
| SN-I-238F | 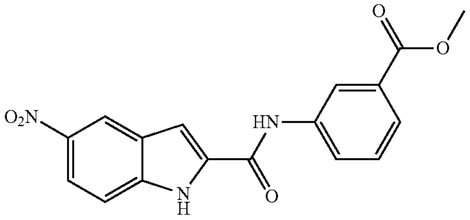 [SMILES: COC(=O)c1cccc(NC(=O)c2cc3cc([N+](=O)[O-])ccc3[nH]2)c1] | 31.4 | >300[b] |
| SN-I-237D | 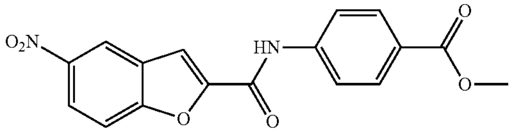 [SMILES: COC(=O)c1ccc(NC(=O)c2cc3cc([N+](=O)[O-])ccc3o2)cc1] | 144.0 | >300[b] |
| SN-I-236 | 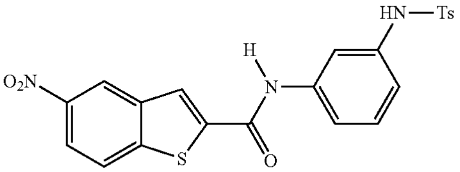 [SMILES: Cc1ccc(S(=O)(=O)Nc2cccc(NC(=O)c3cc4cc([N+](=O)[O-])ccc4s3)c2)cc1] | 63.7 | >300[b] |
| SN-I-238D | 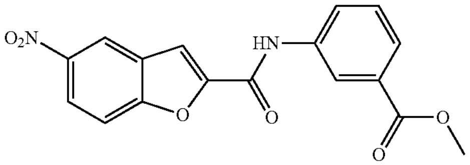 [SMILES: COC(=O)c1cccc(NC(=O)c2cc3cc([N+](=O)[O-])ccc3o2)c1] | 2.7 | >300[b] |
| SN-I-248J | 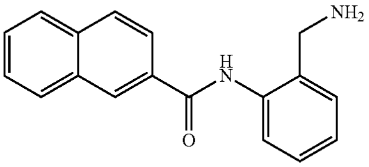 [SMILES: NCc1ccccc1NC(=O)c1ccc2ccccc2c1] | 160.1 | >300[b] |
| SN-I-247B | 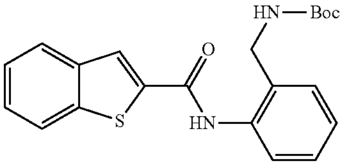 [SMILES: CC(C)(C)OC(=O)NCc1ccccc1NC(=O)c1cc2ccccc2s1] | 43.4 | >300[b] |
| SN-I-247A | 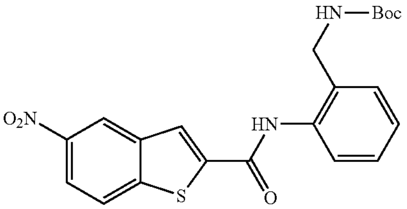 [SMILES: CC(C)(C)OC(=O)NCc1ccccc1NC(=O)c1cc2cc([N+](=O)[O-])ccc2s1] | 51.5 | >300[b] |

TABLE 2-continued
| Biofilm and Growth inhibitory activity of compounds | | | |
|---|---|---|---|
| Code | Structure | Biofilm Inhibition $IC_{50}$ (μM)[a] | Growth Inhibition $MIC_{50}$ (μM) |
| SN-I-247C | 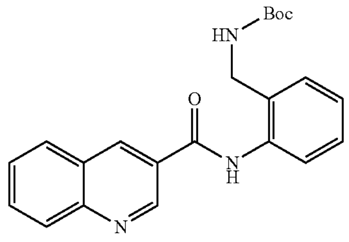 [SMILES: CC(C)(C)OC(=O)NCc1ccccc1NC(=O)c1cnc2ccccc2c1] | 52.8 | >300[b] |
| SN-I-248C | 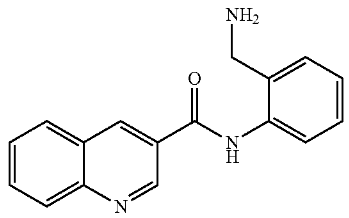 [SMILES: NCc1ccccc1NC(=O)c1cnc2ccccc2c1] | 135.6 | >300[b] |
| SN-I-248A | 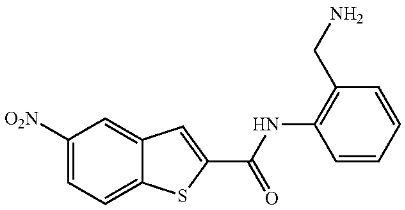 [SMILES: NCc1ccccc1NC(=O)c1cc2cc([N+](=O)[O-])ccc2s1] | 106.2 | >300[b] |
| SN-I-248H | 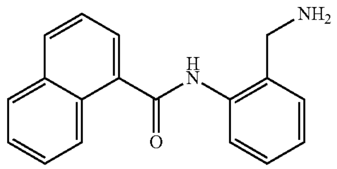 [SMILES: NCc1ccccc1NC(=O)c1cccc2ccccc12] | 93.3 | >300[b] |
| SN-I-247J | 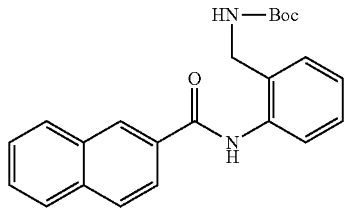 [SMILES: CC(C)(C)OC(=O)NCc1ccccc1NC(=O)c1ccc2ccccc2c1] | 56.8 | >300[b] |
| SN-I-247L | 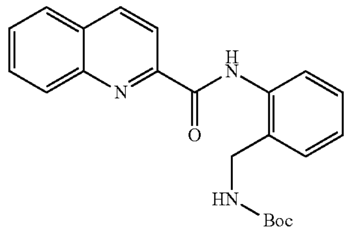 [SMILES: CC(C)(C)OC(=O)NCc1ccccc1NC(=O)c1ccc2ccccc2n1] | 67.5 | >300[b] |

TABLE 2-continued
| Biofilm and Growth inhibitory activity of compounds | | | |
|---|---|---|---|
| Code | Structure | Biofilm Inhibition $IC_{50}$ (μM)[a] | Growth Inhibition $MIC_{50}$ (μM) |
| SN-I-243J | 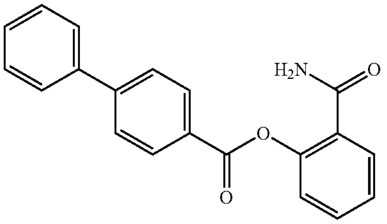 [SMILES: NC(=O)c1ccccc1OC(=O)c1ccc(-c2ccccc2)cc1] | 55.6 | >300[b] |
| SN-I-241J | 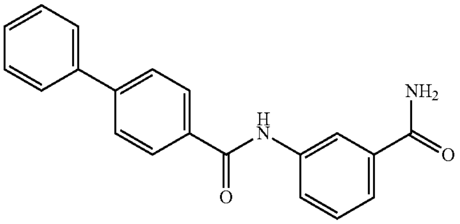 [SMILES: NC(=O)c1cccc(NC(=O)c2ccc(-c3ccccc3)cc2)c1] | 79.9 | >300[b] |
| SN-I-241I | 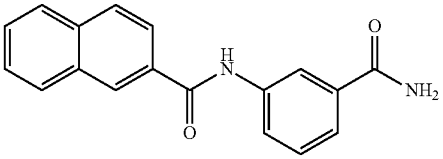 [SMILES: NC(=O)c1cccc(NC(=O)c2ccc3ccccc3c2)c1] | 67.7 | >300[b] |
| SN-I-241L | 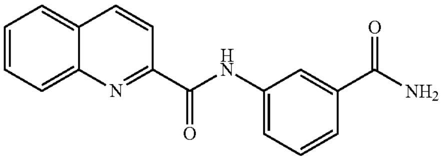 [SMILES: NC(=O)c1cccc(NC(=O)c2ccc3ccccc3n2)c1] | 111 | >300[b] |
| SN-I-243I | 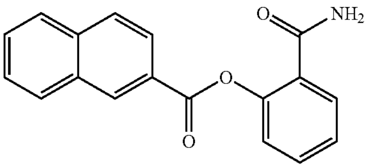 [SMILES: NC(=O)c1ccccc1OC(=O)c1ccc2ccccc2c1] | 98.3 | >300[b] |
| SN-I-257I | 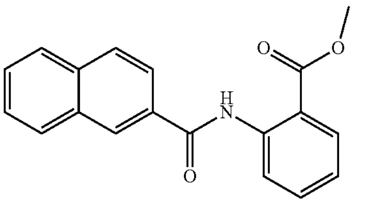 [SMILES: COC(=O)c1ccccc1NC(=O)c1ccc2ccccc2c1] | 121.3 | >300[b] |
| SN-I-257D | 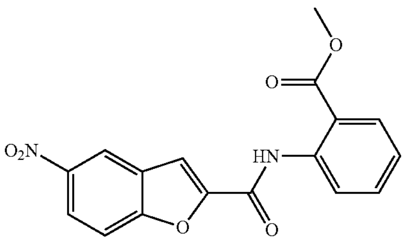 [SMILES: COC(=O)c1ccccc1NC(=O)c1cc2cc([N+](=O)[O-])ccc2o1] | 71.4 | >300[b] |

TABLE 2-continued
| Code | Structure | Biofilm Inhibition $IC_{50}$ (μM)[a] | Growth Inhibition $MIC_{50}$ (μM) |
|---|---|---|---|
| Biofilm and Growth inhibitory activity of compounds | | | |
| SN-I-258L | 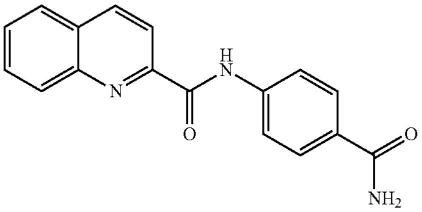 | 54.4 | >300[b] |
| SN-I-257L | 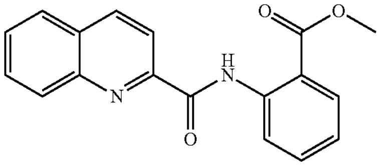 [SMILES: COC(=O)c1ccccc1NC(=O)c1ccc2ccccc2n1] | 89.5 | >300[b] |
| SN-I-257B | 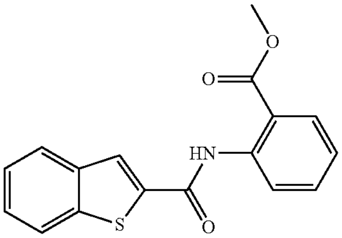 [SMILES: COC(=O)c1ccccc1NC(=O)c1cc2ccccc2s1] | 74.9 | >300[b] |
| HW-1-157 | 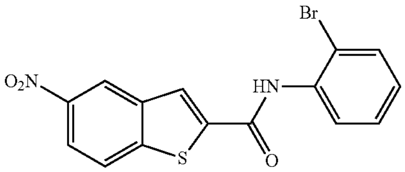 [SMILES: O=C(Nc1ccccc1Br)c1cc2cc([N+](=O)[O-])ccc2s1] | 122.1 | >300[b] |
| HW-1-171 | 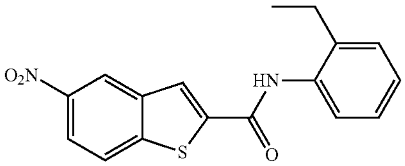 [SMILES: CCc1ccccc1NC(=O)c1cc2cc([N+](=O)[O-])ccc2s1] | 157.7 | >300[b] |
| HW-1-170 | 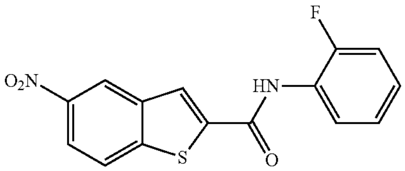 [SMILES: O=C(Nc1ccccc1F)c1cc2cc([N+](=O)[O-])ccc2s1] | 162.3 | >300[b] |
| SN-I-242G | 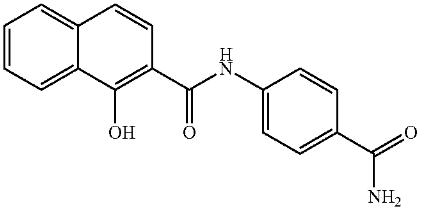 [SMILES: NC(=O)c1ccc(NC(=O)c2ccc3ccccc3c2O)cc1] | 56.9 | >300[b] |

TABLE 2-continued
| Biofilm and Growth inhibitory activity of compounds | | | |
|---|---|---|---|
| Code | Structure | Biofilm Inhibition $IC_{50}$ (μM)[a] | Growth Inhibition $MIC_{50}$ (μM) |
| SN-I-241K | 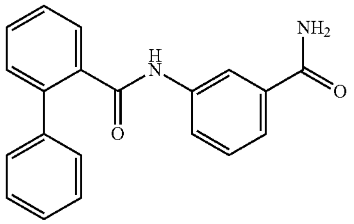 [SMILES: NC(=O)c1cccc(NC(=O)c2ccccc2-c2ccccc2)c1] | 49.4 | >300[b] |
| SN-I-242H | 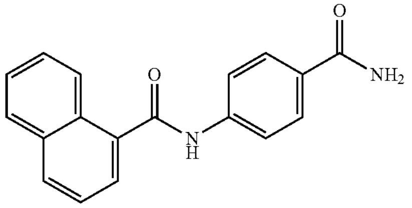 [SMILES: NC(=O)c1ccc(NC(=O)c2cccc3ccccc23)cc1] | 167.3 | >300[b] |
| SN-I-241H | 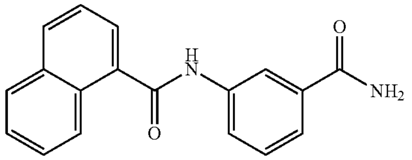 [SMILES: NC(=O)c1cccc(NC(=O)c2cccc3ccccc23)c1] | 195.2 | >300[b] |
| SN-I-238e | 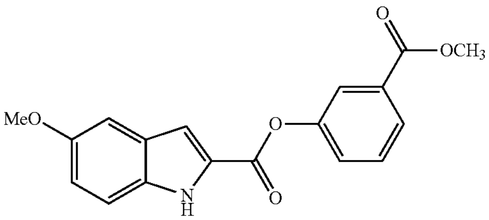 [SMILES: COC(=O)c1cccc(OC(=O)c2cc3cc(OC)ccc3[nH]2)c1] | 112.8 | >300[b] |
| SN-I-248b | 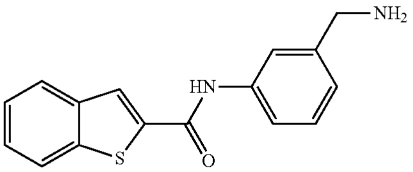 [SMILES: NCc1cccc(NC(=O)c2cc3ccccc3s2)c1] | 209.0 | >300[b] |
| SN-I-237f | 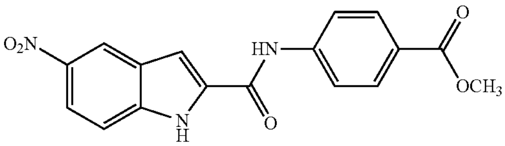 [SMILES: COC(=O)c1ccc(NC(=O)c2cc3cc([N+](=O)[O-])ccc3[nH]2)cc1] | 196.1 | >300[b] |
| SN-I-272VH | 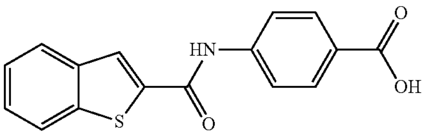 [SMILES: O=C(O)c1ccc(NC(=O)c2cc3ccccc3s2)cc1] | 179.84 | >300[b] |
| SN-I-272OH | 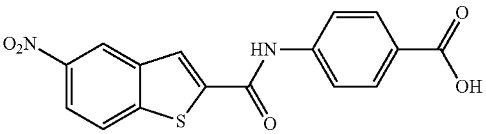 [SMILES: O=C(O)c1ccc(NC(=O)c2cc3cc([N+](=O)[O-])ccc3s2)cc1] | 15.6 | >300[b] |

TABLE 2-continued
| Biofilm and Growth inhibitory activity of compounds | | | |
|---|---|---|---|
| Code | Structure | Biofilm Inhibition $IC_{50}$ (μM)[a] | Growth Inhibition $MIC_{50}$ (μM) |
| SN-I-271U | 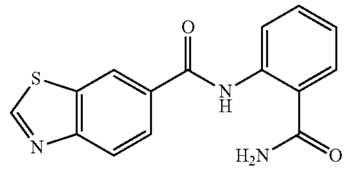 [SMILES: NC(=O)c1ccccc1NC(=O)c1ccc2ncsc2c1] | 36.1 | >300[b] |
| SN-I-271S | 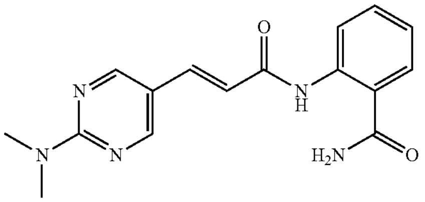 [SMILES: CN(C)c1ncc(/C=C/C(=O)Nc2ccccc2C(N)=O)cn1] | 12.8 | >300[b] |
| HW-1-179 | 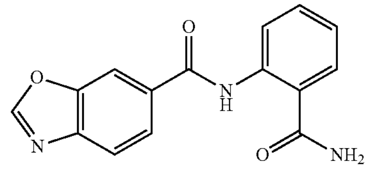 [SMILES: NC(=O)c1ccccc1NC(=O)c1ccc2ncoc2c1] | 65.1 | >300[b] |
| SN-I-287 | 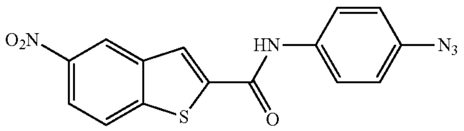 [SMILES: [N-]=[N+]=Nc1ccc(NC(=O)c2cc3cc([N+](=O)[O-])ccc3s2)cc1] | 250 | >300[b] |
| SN-I-288 | 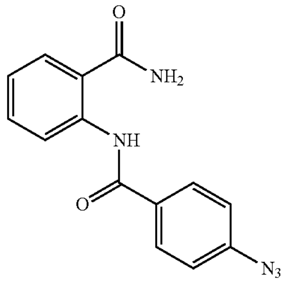 [SMILES: [N-]=[N+]=Nc1ccc(C(=O)Nc2ccccc2C(N)=O)cc1] | 212 | >300[b] |
| SN-I-285 | 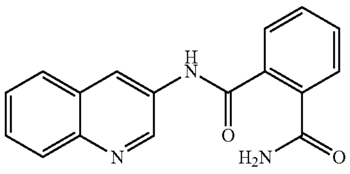 [SMILES: NC(=O)c1ccccc1C(=O)Nc1cnc2ccccc2c1] | 102 | >300[b] |
| SN-II-14 | 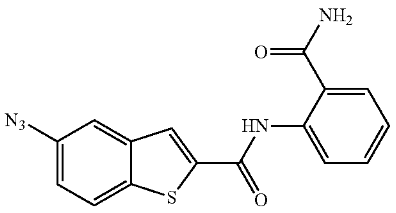 [SMILES: [N-]=[N+]=Nc1ccc2sc(C(=O)Nc3ccccc3C(N)=O)cc2c1] | 57.2 | >300[b] |

TABLE 2-continued
Biofilm and Growth inhibitory activity of compounds
| Code | Structure | Biofilm Inhibition $IC_{50}$ (μM)[a] | Growth Inhibition $MIC_{50}$ (μM) |
|---|---|---|---|
| SN-II-50 | 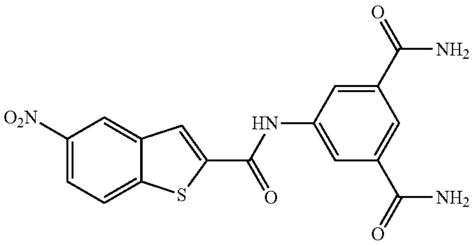 [SMILES: NC(=O)c1cc(NC(=O)c2cc3cc([N+](=O)[O-])ccc3s2)cc(C(N)=O)c1] | 4.6 | >300[b] |
| SN-II-59 | 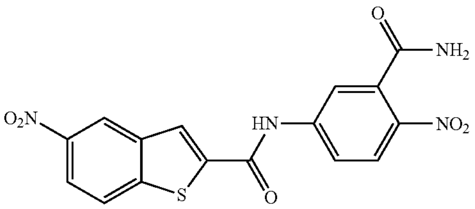 [SMILES: NC(=O)c1cc(NC(=O)c2cc3cc([N+](=O)[O-])ccc3s2)ccc1[N+](=O)[O-]] | 23.4 | >300[b] |
| 298b2 | 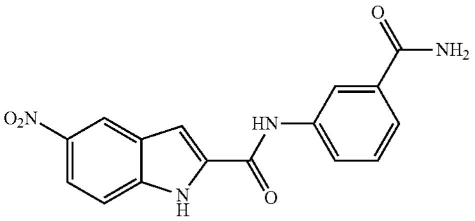 [SMILES: NC(=O)c1cccc(NC(=O)c2cc3cc([N+](=O)[O-])ccc3[nH]2)c1] | 138.3 | >300[b] |
| 298C9 | 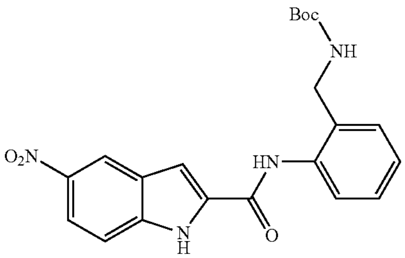 [SMILES: CC(C)(C)OC(=O)NCc1ccccc1NC(=O)c1cc2cc([N+](=O)[O-])ccc2[nH]1] | 26.8 | >300[b] |
| 298C10 | 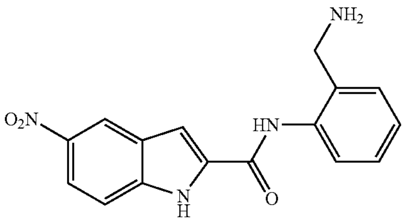 [SMILES: NCc1ccccc1NC(=O)c1cc2cc([N+](=O)[O-])ccc2[nH]1] | 98.3 | >300[b] |
| 298D5 | 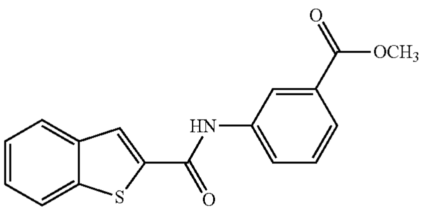 [SMILES: COC(=O)c1cccc(NC(=O)c2cc3ccccc3s2)c1] | 120.7 | >300[b] |

TABLE 2-continued
| Biofilm and Growth inhibitory activity of compounds | | | |
|---|---|---|---|
| Code | Structure | Biofilm Inhibition $IC_{50}$ (μM)[a] | Growth Inhibition $MIC_{50}$ (μM) |
| 298F7 | 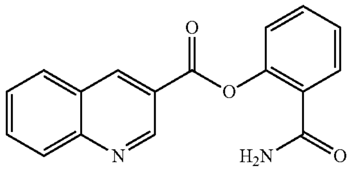 [SMILES: NC(=O)c1ccccc1OC(=O)c1cnc2ccccc2c1] | 30.4 | >300[b] |
| 298G5 | 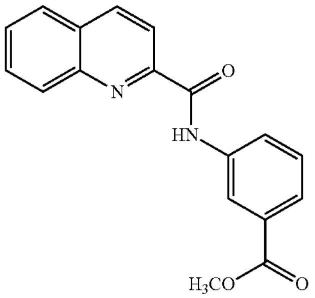 [SMILES: COC(=O)c1cccc(NC(=O)c2ccc3ccccc3n2)c1] | 92.3 | >300[b] |
| 298G6 | 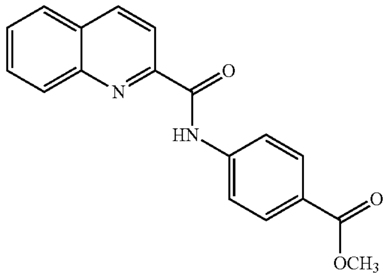 [SMILES: COC(=O)c1ccc(NC(=O)c2ccc3ccccc3n2)cc1] | 105.6 | >300[b] |
| 298G7 | 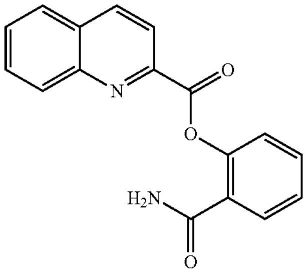 [SMILES: NC(=O)c1ccccc1OC(=O)c1ccc2ccccc2n1] | 104.8 | >300[b] |
| SN-II-81Cl | 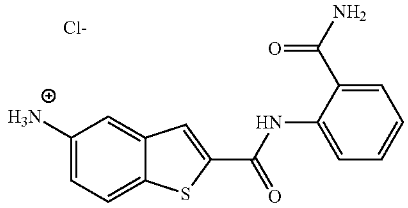 [SMILES: NC(=O)c1ccccc1NC(=O)c1cc2cc([NH3+])ccc2s1 ; [Cl-]] | 9.6 | >300[b] |
| SN-II-81F | 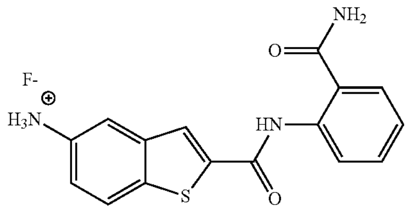 | 56.4 | >300[b] |

TABLE 2-continued

Biofilm and Growth inhibitory activity of compounds

| Code | Structure | Biofilm Inhibition $IC_{50}$ (μM)[a] | Growth Inhibition $MIC_{50}$ (μM) |
|---|---|---|---|
| SN-II-105 | 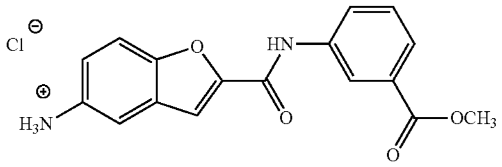 [SMILES: [Cl-] ; COC(=O)c1cccc(NC(=O)c2cc3cc(N)ccc3o2)c1] | 5.5 | 346.7 |
| SN-II-106 | 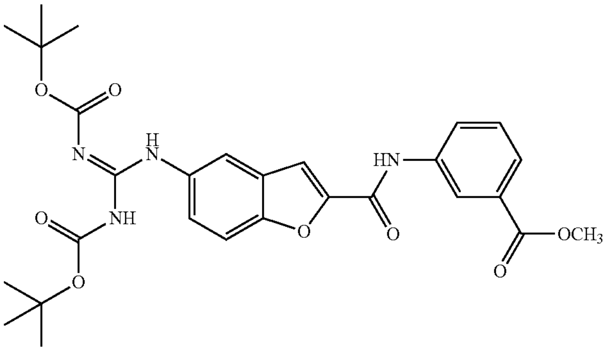 [SMILES: COC(=O)c1cccc(NC(=O)c2cc3cc(N/C(=N\C(=O)OC(C)(C)C)NC(=O)OC(C)(C)C)ccc3o2)c1] | 14.0 | 29.0 |
| SN-II-107 | 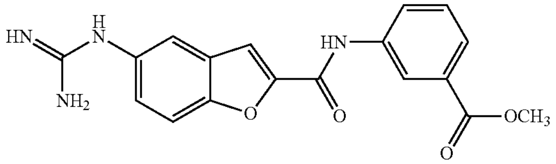 [SMILES: COC(=O)c1cccc(NC(=O)c2cc3cc(NC(=N)N)ccc3o2)c1] | 16.6 | 45.9 |

[a]Determined by *S. mutans* biofilm inhibition assay.

[b]No inhibition up to 300 μM.

TABLE 3

Biofilm and Growth Inhibitory activity of compounds

| Code | Structure | Growth Inhibition $MIC_{50}$ (μM) | Biofilm Inhibition $IC_{50}$ (μM)[a] |
|---|---|---|---|
| SN-II-113 | 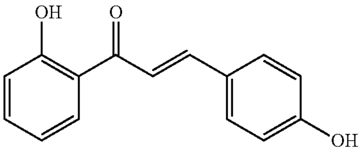 [SMILES: O=C(/C=C/c1ccc(O)cc1)c1ccccc1O] | >300[b] | 213.2 ± 7 |
| SN-II-32 | 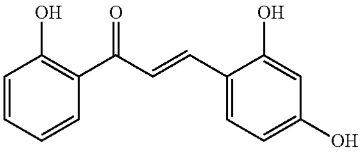 [SMILES: O=C(/C=C/c1ccc(O)cc1O)c1ccccc1O] | 327 ± 24 | 250.0 ± 16 |
| RZ-1-90 | 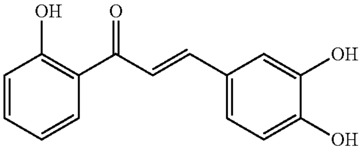 [SMILES: O=C(/C=C/c1ccc(O)c(O)c1)c1ccccc1O] | >300[b] | 356.2 ± 14 |

TABLE 3-continued
| Biofilm and Growth Inhibitory activity of compounds | | | |
|---|---|---|---|
| Code | Structure | Growth Inhibition $MIC_{50}$ (μM) | Biofilm Inhibition $IC_{50}$ (μM)[a] |
| LC-I-206 | 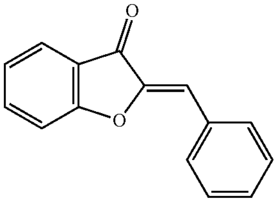 [SMILES: O=C1/C(=C/c2ccccc2)Oc2ccccc21] | >300[b] | 320.5 ± 21 |
| LC-I-203 | 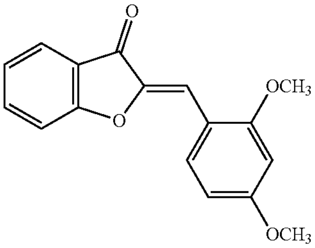 [SMILES: COc1ccc(/C=C2\Oc3ccccc3C2=O)c(OC)c1] | >300[b] | 40.6 ± 3 |
| LC-I-197 | 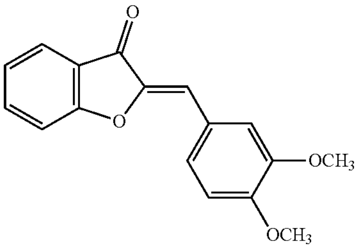 [SMILES: COc1ccc(/C=C2\Oc3ccccc3C2=O)cc1OC] | 37.1 ± 6 | 8.4 ± 1 |
| LC-I-205 | 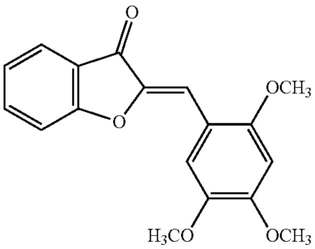 [SMILES: COc1cc(OC)c(OC)cc1/C=C1\Oc2ccccc2C1=O] | >300[b] | 8.3 ± 1 |
| SN-II-115 | 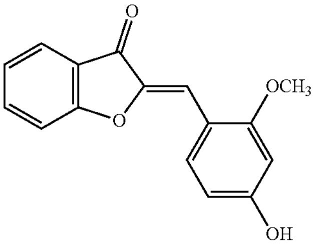 [SMILES: COc1cc(O)ccc1/C=C1\Oc2ccccc2C1=O] | 152.9 ± 21 | 132.7 ± 24 |
| SN-II-118 | 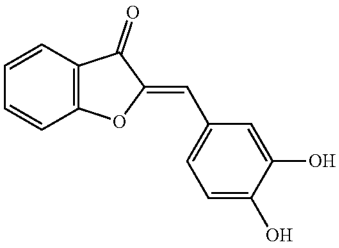 [SMILES: O=C1/C(=C/c2ccc(O)c(O)c2)Oc2ccccc21] | 262.9 ± 14 | 280.2 ± 35 |

TABLE 3-continued
| Biofilm and Growth Inhibitory activity of compounds | | | |
|---|---|---|---|
| Code | Structure | Growth Inhibition $MIC_{50}$ (μM) | Biofilm Inhibition $IC_{50}$ (μM)[a] |
| SN-II-110 | 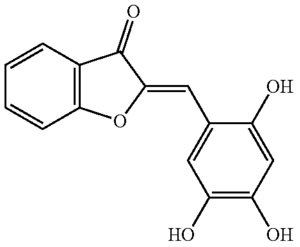 [SMILES: O=C1/C(=C/c2cc(O)c(O)cc2O)Oc2ccccc21] | 156.6 ± 13 | 10.2 ± 2 |
| SN-II-78 | 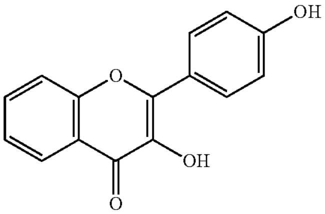 [SMILES: O=c1c(O)c(-c2ccc(O)cc2)oc2ccccc12] | NI | 200.3 ± 10 |
| SN-II-92 | 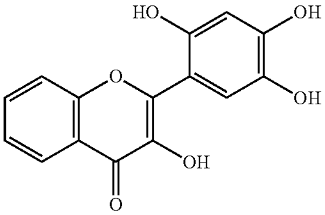 [SMILES: O=c1c(O)c(-c2cc(O)c(O)cc2O)oc2ccccc12] | 63.1 ± 4 | 19.8 ± 2 |
| LC-I-203 | 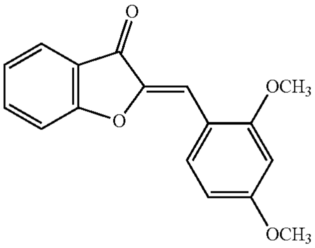 [SMILES: COc1ccc(/C=C2\Oc3ccccc3C2=O)c(OC)c1] | NI | 40.6 ± 3 |
| LC-I-197 | 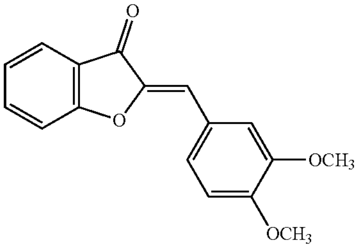 [SMILES: COc1ccc(/C=C2\Oc3ccccc3C2=O)cc1OC] | 37.1 ± 6 | 8.4 ± 1 |
| LC-I-205 | 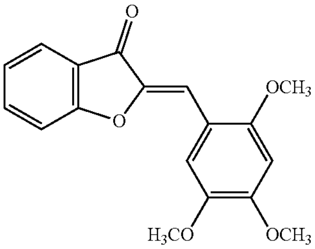 [SMILES: COc1cc(OC)c(OC)cc1/C=C1\Oc2ccccc2C1=O] | NI | 8.3 ± 1 |

TABLE 3-continued
| Biofilm and Growth Inhibitory activity of compounds | | | |
|---|---|---|---|
| Code | Structure | Growth Inhibition $MIC_{50}$ (μM) | Biofilm Inhibition $IC_{50}$ (μM)[a] |
| SN-II-115 | 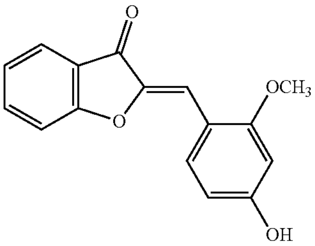 [SMILES: COc1cc(O)ccc1/C=C1\Oc2ccccc2C1=O] | 152.9 ± 21 | 132.7 ± 24 |
| SN-II-110 | 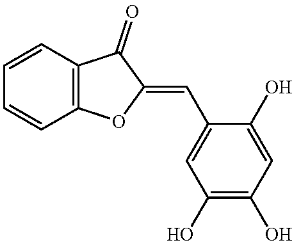 [SMILES: O=C1/C(=C/c2cc(O)c(O)cc2O)Oc2ccccc21] | 156.6 ± 13 | 10.2 ± 2 |
| Okanin (natural) | 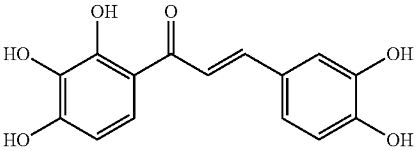 [SMILES: O=C(/C=C/c1ccc(O)c(O)c1)c1ccc(O)c(O)c1O] | 534 ± 17 | 64 ± 7 |
| RZ-1-86 | 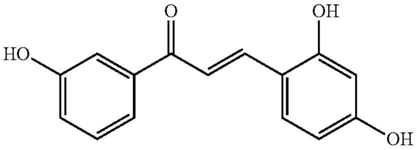 [SMILES: O=C(/C=C/c1ccc(O)cc1O)c1cccc(O)c1] | 468.9 ± 16 | 32 ± 5 |
| SN-II-24-B6 | 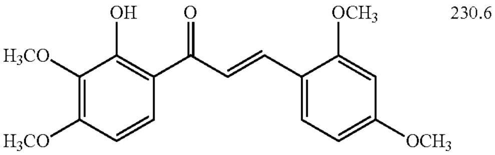 | 230.6 ± 12 | 101 ± 3 |
| SN-II-49C | 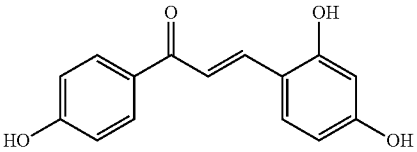 [SMILES: O=C(/C=C/c1ccc(O)cc1O)c1ccc(O)cc1] | 782 ± 96 | 77 ± 8 |
| AP-I-240 | 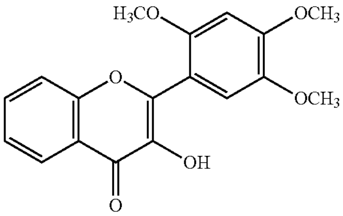 [SMILES: COc1cc(OC)c(-c2oc3ccccc3c(=O)c2O)cc1OC] | 15.3 ± 3 | 10.1 ± 1 |

TABLE 3-continued
Biofilm and Growth Inhibitory activity of compounds
| Code | Structure | Growth Inhibition $MIC_{50}$ (μM) | Biofilm Inhibition $IC_{50}$ (μM)[a] |
|---|---|---|---|
| SN-II-79 | 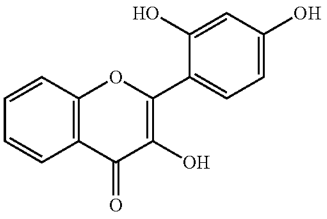 [SMILES: O=c1c(O)c(-c2ccc(O)cc2O)oc2ccccc12] | 30.0 ± 1 | 65.9 ± 1 |
| PBF | 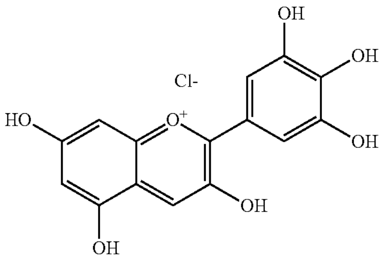 [SMILES: Oc1cc(O)c2cc(O)c(-c3cc(O)c(O)c(O)c3)[o+]c2c1 ; [Cl-]] | 262.5 ± 21.0 | 135.4 ± 5.6 |
| PAY | 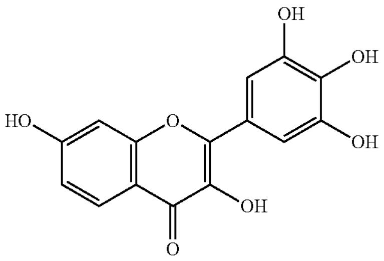 [SMILES: O=c1c(O)c(-c2cc(O)c(O)c(O)c2)oc2cc(O)ccc12] | NI | 74.5 ± 9.8 |
| PAC | 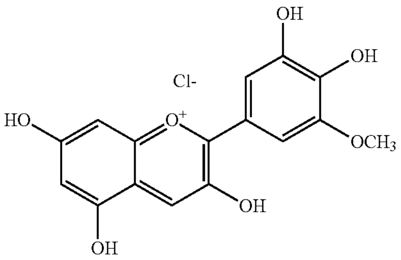 [SMILES: COc1cc(-c2[o+]c3cc(O)cc(O)c3cc2O)cc(O)c1O ; [Cl-]] | 274.2 ± 45.8 | 61.2 ± 2.3 |
| Piceatannol (natural) | 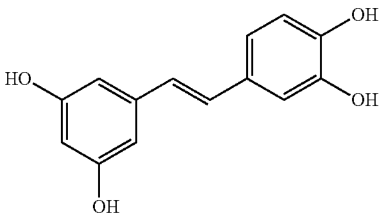 [SMILES: Oc1cc(O)cc(/C=C/c2ccc(O)c(O)c2)c1] | 564 ± 38 | 52 ± 6 |

TABLE 3-continued

| Biofilm and Growth Inhibitory activity of compounds | | | |
|---|---|---|---|
| Code | Structure | Growth Inhibition $MIC_{50}$ (μM) | Biofilm Inhibition $IC_{50}$ (μM)[a] |
| Resveratrol (natural) | 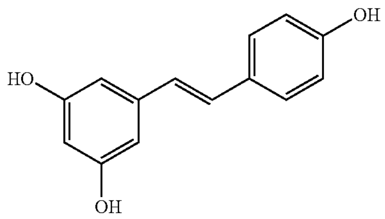 [SMILES: Oc1ccc(/C=C/c2cc(O)cc(O)c2)cc1] | 546 ± 16 | 82 ± 4 |

[a]Determined by *S. mutans* biofilm inhibition assay.
[b]No inhibition up to 300 μM.
NI = No inhibition up to 400 μM.

TABLE 4

| Biofilm and Growth Inhibitory activity of stilbenes | | | | | |
|---|---|---|---|---|---|
| Entry | NSC Code | Structure | Biofilm $IC_{50}$ (μM) | Growth $MIC_{50}$ (μM)[a] | Selectivity |
| 1 | NA | 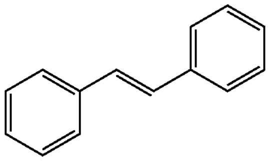 [SMILES: C(=C\c1ccccc1)/c1ccccc1] | NI | NI | NA |
| 2 | NA | 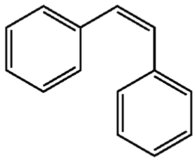 [SMILES: C(=C/c1ccccc1)/c1ccccc1] | NI | NI | NA |
| 3 | 403525 | 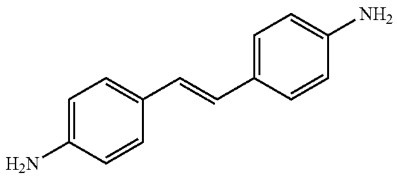 | NI | NI | NA |
| 4 | 4184 | 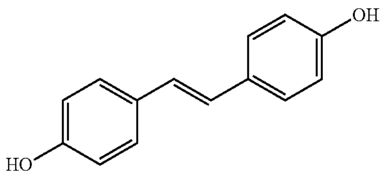 [SMILES: Oc1ccc(/C=C/c2ccc(O)cc2)cc1] | 344 ± 17 | 854 ± 58 | 2.4 |
| 5 | 78326 | 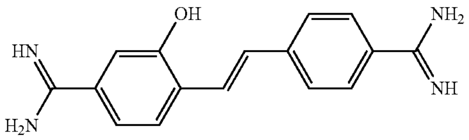 | 104 ± 7 | 179 ± 23 | 1.7 |

TABLE 4-continued
Biofilm and Growth Inhibitory activity of stilbenes
| Entry | NSC Code | Structure | Biofilm $IC_{50}$ (μM) | Growth $MIC_{50}$ (μM)[a] | Selectivity |
|---|---|---|---|---|---|
| 6 | 43312 | 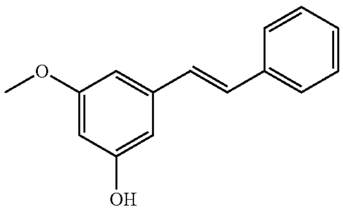 [SMILES: COc1cc(O)cc(/C=C/c2ccccc2)c1] | 477 ± 51 | 546 ± 25 | 1.1 |
| 7 | NA | 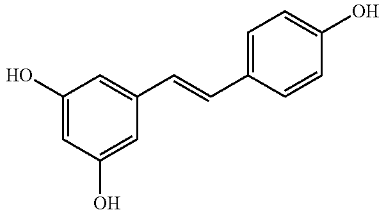 [SMILES: Oc1ccc(/C=C/c2cc(O)cc(O)c2)cc1] | 102.2 ± 4 | 546.4 ± 15.9 | 5.3 |
| 8 | 365798 | 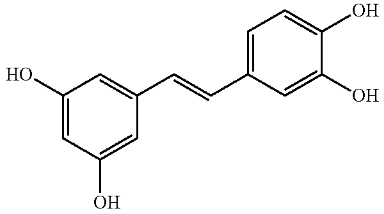 [SMILES: Oc1cc(O)cc(/C=C/c2ccc(O)c(O)c2)c1] | 52 ± 6 | 564 ± 37.8 | 10.8 |
| 9 | 381864 | 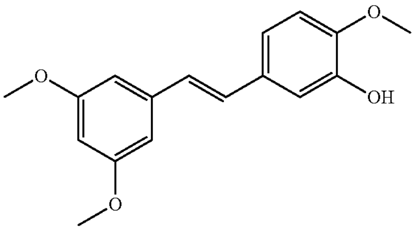 | 122 ± 11 | 137 ± 6 | 1.1 |
| 10 | 70861 | 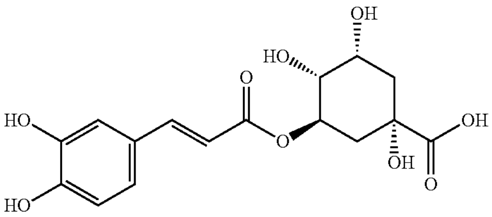 [SMILES: O=C(/C=C/c1ccc(O)c(O)c1)O[C@@H]1C[C@](O)(C(=O)O)C[C@@H](O)[C@H]1O] | 518 ± 85 | 1724 ± 53 | 3.3 |
| 11 | 123262 | 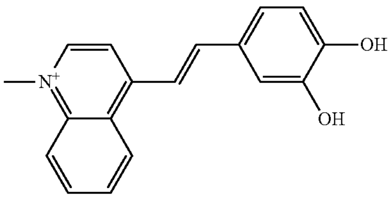 [SMILES: C[n+]1ccc(/C=C/c2ccc(O)c(O)c2)c2ccccc21] | 104 ± 6 | >400 | 4.0 |
| 12 | 43321 | 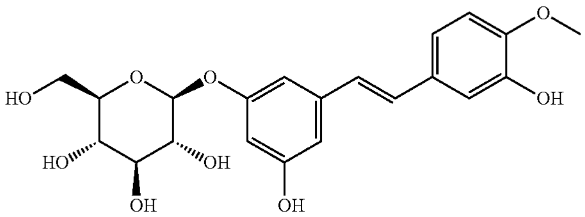 [SMILES: COc1ccc(/C=C/c2cc(O)cc(O[C@@H]3O[C@H](CO)[C@@H](O)[C@H](O)[C@H]3O)c2)cc1O] | 106 ± 11 | 134 ± 11 | 1.2 |

TABLE 4-continued

| Biofilm and Growth Inhibitory activity of stilbenes | | | | | |
|---|---|---|---|---|---|
| Entry | NSC Code | Structure | Biofilm $IC_{50}$ (μM) | Growth $MIC_{50}$ (μM)[a] | Selectivity |
| 13 | 16952974 | 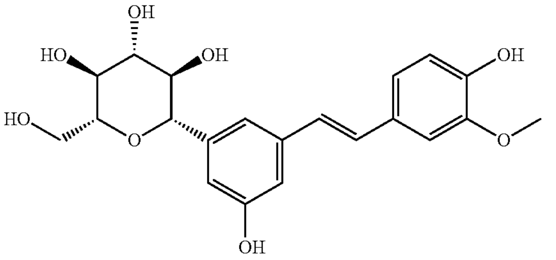 [SMILES: COc1cc(/C=C/c2cc(O)cc([C@@H]3O[C@H](CO)[C@@H](O)[C@H](O)[C@H]3O)c2)ccc1O] | NI | NI | NA |

[a]Average of at least 5 measurements;
NI No inhibition;
NA Not available.

Table 5 lists the $IC_{50}$ for *S. mutans* biofilm inhibition as well as percent inhibition of Gtfs at a 10 μM concentration of selected compounds from Table 1. A well-established zymographic assay was used to determine enzymatic activity of Gtfs (Mattos-Graner et al. (2004) *J. Clin. Microbiol.* 42, 2752). In brief, overnight *S. mutans* UA159 cultures were diluted 1:100 in fresh 5 mL THB with 50 μL of selective compounds at a series of concentrations. Treated bacteria were grown to OD470 of 1.0, and spun down by centrifugation at 4° C., and culture supernatants were collected and filtered through a 0.22-μm-pore-size filter membrane to remove residual bacterial cells and dialyzed at 4° C. against 0.02 M sodium phosphate buffer (pH 6.8), with 10 μM phenylmethylsulfonyl fluoride (PMSF), followed by a second dialysis against 0.2 mM sodium phosphate containing 10 μM PMSF. After dialysis, 4 mL of samples were concentrated to 40 μL by 100K Amicon Ultra-4 centrifugal filter (Merck Millipore Ltd.). For electrophoresis and zymographic analysis, 10 μL of each concentrated culture supernatant was applied to 8% SDS-PAGE in duplicate. One gel was used for protein staining with Coomassie blue dye, while the other one was subjected to zymographic assay as described (Mattos-Graner et al. (2004) *J. Clin. Microbiol.* 42, 2752). The resultant white opaque glucan bands were visualized against a black background.

TABLE 5

| Biofilm and Gtf inhibitory activities of selected compounds | | | | |
|---|---|---|---|---|
| Code | Structure | Notebook | Biofilm Inhibition $IC_{50}$ (μM)[a] | % Inhibition of GTFs at 10 μM[b] |
| 3A | 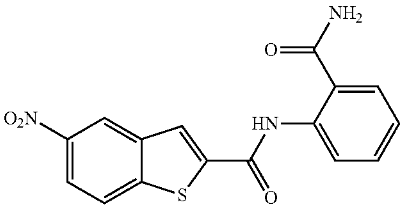 | SN-I-204 | 16.7 | 30.3 |
| 3D | 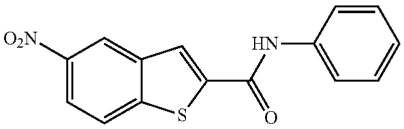 [SMILES: O=C(Nc1ccccc1)c1cc2cc([N+](=O)[O-])ccc2s1] | SN-I-209 | >500[c] | NI[d] |
| 3I | 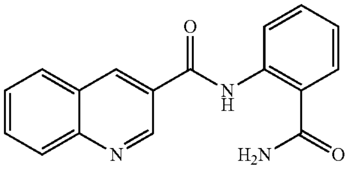 | SN-I-199 | 15.3 | 36.6 |

TABLE 5-continued

Biofilm and Gtf inhibitory activities of selected compounds

| Code | Structure | Notebook | Biofilm Inhibition $IC_{50}$ (μM)[a] | % Inhibition of GTFs at 10 μM[b] |
|---|---|---|---|---|
| 3L | 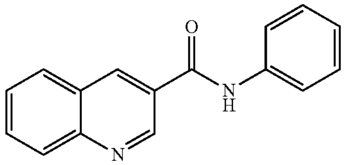 [SMILES: O=C(Nc1ccccc1)c1cnc2ccccc2c1] | SN-I-210 | >500[c] | NI[d] |
| 3M | 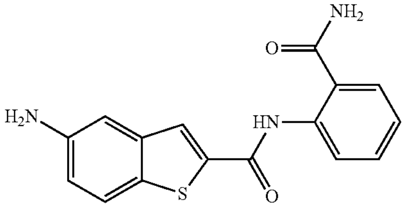 | SN-I-216 | 10.2 | 42.2 |
| 3N | 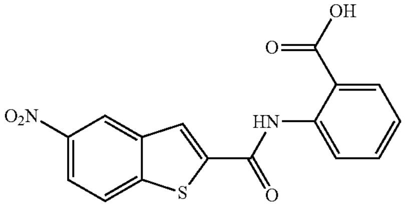 [SMILES: O=C(Nc1ccccc1C(=O)O)c1cc2cc([N+](=O)[O-])ccc2s1] | SN-I-222 | 89.3 | 30.1 |
| 3O | 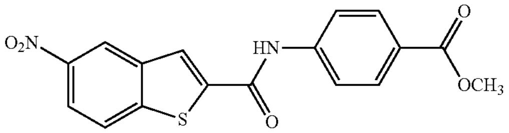 [SMILES: COC(=O)c1ccc(NC(=O)c2cc3cc([N+](=O)[O-])ccc3s2)cc1] | SN-I-217 | 9.6 | 54.8 |

[a]Determined by *S. mutans* biofilm inhibition assay.
[b]Determined by *S. mutans* GTF zymogram assay.
[c]No inhibition up to 500 μM.
[d]No inhibition up to 10 μM.

Example 2: Structure-Based Discovery of Small Molecule Inhibitors of Cariogenic Virulence

*Streptococcus mutans* employs a key virulence factor, three glucosyltransferase (GtfBCD) enzymes to establish cariogenic biofilms. Therefore, the inhibition of GtfBCD would provide anti-virulence therapeutics. Here a small molecule library of 500,000 small molecule compounds was screened in silico against the available crystal structure of the GtfC catalytic domain. Based on the predicted binding affinities and drug-like properties, small molecules were selected and evaluated for their ability to reduce *S. mutans* biofilms, as well as inhibit the activity of Gtfs. The most potent inhibitor was further characterized for Gtf binding using OctetRed instrument, which yielded low micromolar $K_D$ against GtfB and nanomolar $K_D$ against GtfC, demonstrating selectivity towards GtfC. Additionally, the lead compound did not affect the overall growth of *S. mutans* and commensal oral bacteria, and selectively inhibit the biofilm formation by *S. mutans*, indicative of its selectivity and non-bactericidal nature. The lead compound also effectively reduced cariogenicity in vivo in a rat model of dental caries. An analog that docked poorly in the GtfC catalytic domain failed to inhibit the activity of Gtfs and *S. mutans* biofilms, signifying the specificity of the lead compound. This report illustrates the validity and potential of structure-based design of anti-*S. mutans* virulence inhibitors.

Though the oral cavity harbors over 700 different bacterial species, *Streptococcus mutans* initiates the cariogenic process and remains as the key etiological agent. Using key matrix producing enzymes, glucosyltransferases (Gtfs), *S. mutans* produces sticky glucosyl glucan polymers, which facilitate the attachment of the bacteria to the tooth surface. The glucans is a major component of the biofilm matrix that shields the microbial community from host defenses, mechanical and oxidative stresses, and orchestrates the formation of cariogenic biofilms. Furthermore, copious amounts of lactic acid are produced as a byproduct of bacterial consumption of dietary sugars within the mature biofilm community, which ultimately leads to demineralization of the tooth surface, ensuing cariogenesis.

Current practices to prevent dental caries remove oral bacteria non-discriminatively through chemical and physical means such as mouthwash and tooth brushing (Lingstrom, P., van Houte, J. & Kashket, S. Food starches and dental caries. *Critical reviews in oral biology and medicine: an official publication of the American Association of Oral Biologists* 11, 366-380 (2000)). Since the biofilm assembly renders bacteria to become more resistant to antibiotics and other manipulations, these traditional approaches have had only limited success. Additionally, existing mouthwashes are often associated with adverse side effects because the use of broad-spectrum antimicrobials are often detrimental to beneficial commensal species. Selectively targeting cariogenic pathogens such as *S. mutans* has been explored previously, however it was found that the antimicrobial peptide also alters the overall microbiota (Guo, L. et al. Precision-guided antimicrobial peptide as a targeted modulator of human microbial ecology. Proceedings of the National Academy of Sciences of the United States of America 112, 7569-7574, (2015). Increasing understanding of bacterial virulence mechanisms provides new opportunities to target and interfere with crucial virulence factors such as Gtfs. This approach has the added advantages of not only being selective, but may also help to preserve the natural microbial flora of the mouth, which may avoid to exert the strong pressure to promote the development of antibiotic resistance, overcoming a major public health issue in the antibiotic era. It is well established that glucans produced by *S. mutans* Gtfs contribute significantly to the cariogenicity of dental biofilms. Therefore, the inhibition of the Gtf activity and the consequential glucan synthesis would impair the *S. mutans* virulence, which could offer an alternative strategy to prevent and treat biofilm-related diseases.

*S. mutans* harbors three Gtfs: GtfB, GtfC, and GtfD. While GtfB synthesizes predominantly insoluble glucans, GtfD only produces water-soluble glucans, and GtfC can synthesize both soluble and insoluble glucans. All Gtfs are composed of three functional regions: the N-terminal variable junction region, the C-terminal glucan-binding region, and the highly conserved catalytic region in the middle, which is essential for the glucan synthesis. The crystal structural of GtfC from *S. mutans* has been determined (Ito, K. et al. Crystal Structure of Glucansucrase from the Dental Caries Pathogen *Streptococcus mutans. J Mol Biol* 408, 177-186 (2011), which provides key molecular insights for the design and development of novel Gtf inhibitors.

Polyphenolic compounds that include catechins, flavonoids, proanthocyanidin oligomers (Duarte, S. et al. Inhibitory effects of cranberry polyphenols on formation and acidogenicity of *Streptococcus mutans* biofilms. *FEMS Microbiology Letters* 257, 50-56 (2006); Percival, R. S., Devine, D. A., Duggal, M. S., Chartron, S. & Marsh, P. D. The effect of cocoa polyphenols on the growth, metabolism, and biofilm formation by *Streptococcus mutans* and *Streptococcus sanguinis. European journal of oral sciences* 114, 343-348, doi:10.1111/j.1600-0722.2006.00386.x (2006); Duarte, S. et al. Inhibitory effects of cranberry polyphenols on formation and acidogenicity of *Streptococcus mutans* biofilms. *FEMS Microbiol Lett* 257, 50-56, doi:10.1111/j.1574-6968.2006.00147.x (2006); Ferrazzano, G. F., Amato, I., Ingenito, A., De Natale, A. & Pollio, A. Anti-cariogenic effects of polyphenols from plant stimulant beverages (cocoa, coffee, tea). *Fitoterapia* 80, 255-262, doi:10.1016/j.fitote.2009.04.006 (2009); Stauder, M. et al. Inhibitory activity by barley coffee components towards *Streptococcus mutans* biofilm. *Current microbiology* 61, 417-421, doi:10.1007/s00284-010-9630-5 (2010); Sendamangalam, V., Choi, O. K., Kim, D. & Seo, Y. The anti-biofouling effect of polyphenols against *Streptococcus mutans. Biofouling* 27, 13-19, doi:10.1080/08927014.2010.535897 (2011); Dong, L. et al. Effects of sub-minimum inhibitory concentrations of antimicrobial agents on *Streptococcus mutans* biofilm formation. *International journal of antimicrobial agents* 39, 390-395, doi:10.1016/j.ijantimicag.2012.01.009 (2012); Nijampatnam, B., Casals, L., Zheng, R., Wu, H. & Velu, S. E. Hydroxychalcone inhibitors of *Streptococcus mutans* glucosyl transferases and biofilms as potential anticaries agents. *Bioorganic & medicinal chemistry letters* 26, 3508-3513, doi:10.1016/j.bmcl.2016.06.033 (2016)), and other plant-derived analogs (Newbrun, E., Hoover, C. I. & Walker, G. J. Inhibition by acarbose, nojirimycin and 1-deoxynojirimycin of glucosyltransferase produced by oral streptococci. *Arch Oral Biol* 28, 531-536 (1983); Nijampatnam, B., Nadkarni, D. H., Wu, H. & Velu, S. E. Antibacterial and Antibiofilm Activities of Makaluvamine Analogs. *Microorganisms* 2, 128-139, doi:10.3390/microorganisms2030128 (2014)) and synthetic small molecules (Ren, Z. et al. Molecule Targeting Glucosyltransferase Inhibits *Streptococcus mutans* Biofilm Formation and Virulence. *Antimicrobial agents and chemotherapy* 60, 126-135, doi:10.1128/aac.00919-15 (2015)) have been studied extensively for years and were found to display modest anti-biofilm activities through modulating the expression of Gtfs of *S. mutans*. However, the selectivity of these bioactive compounds remains to be determined and the potency is not satisfactory for the biofilm inhibition.

In the present study, novel inhibitors of *S. mutans* Gtfs were developed through in silico screening of commercial compound libraries against the active site of the catalytic domain from the *S. mutans* GtfC. A lead compound targeting Gtfs was identified, synthesized, and shown to have the ability to bind to Gtfs and inhibit *S. mutans* biofilm formation selectively in vitro. Furthermore, the lead compound possesses anti-virulence properties in vivo.

Figure 2B:
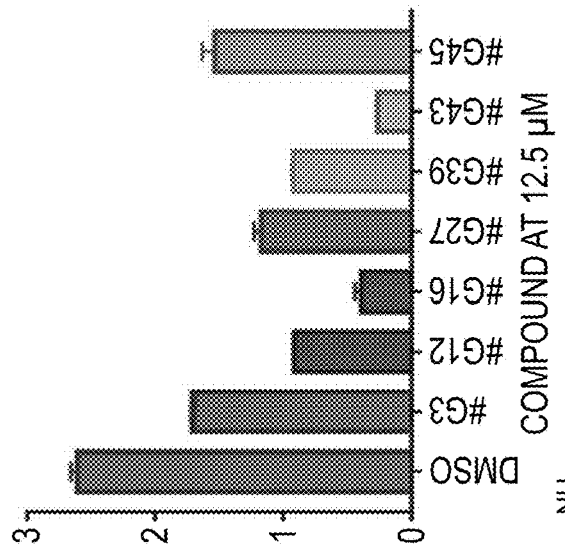
FIG. 2B shows biofilm inhibitory activities of the potent inhibitors at 12.5 μM as determined by the crystal violet assay.

Structure-based virtual screening to identify small-molecule compounds that target Gtfs and inhibit biofilm formation. Taking advantage of the available crystal structure of the GtfC catalytic domain complexed with acarbose, a structure-based in silico screening of 500,000 drug-like compounds was conducted using the FlexX/LeadIT software. The top ranked small molecules, as calculated using the binding energy scores in the FlexX software, were considered based on their binding pose, potential interactions with key residues, and ease of synthesis. Due to the abundance of polar residues in the GtfC active site, several of the top scored docking scaffolds contain aromatic rings, nitro groups, and polar functional groups such as amides and heteroatoms such as sulfur, etc. A total of 90 compounds with diverse scaffolds which vary in their functional groups, hydrophobicity, and H-bond accepting/donating capacity were then purchased and subjected to in vitro biofilm assays using cariogenic *S. mutans*. Seven potent low micromolar inhibitors were identified (FIG. 2A). Two of these compounds (#G16 and #G43) were the most potent, as they inhibited more than 85% of *S. mutans* biofilms at 12.5 μM (FIG. 2B). Compounds #G16 and #G43 share several functional groups including a nitro group, heterocyclic rings, and polar carbonyl functional property.

Figure 3A:
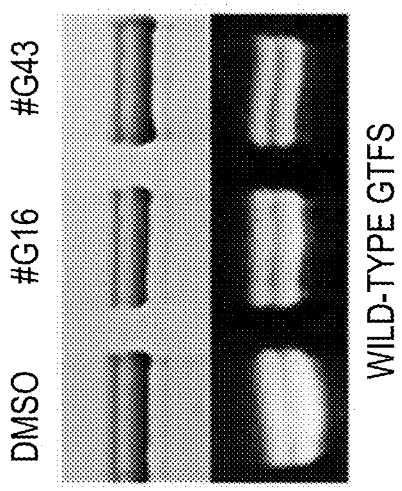
FIGS. 3A-3C show Gtf patterns of *S. mutans* UA159 and its mutant variants. Culture supernatants were prepared from *S. mutans* UA159 and gtf double mutants, and then subjected to SDS-PAGE analysis with equivalent amount of proteins in each lane. The upper panel was stained with Coomassie blue to monitor the total protein amounts while the lower panel shows enzymatic activities of Gtfs with the treatment of the lead by the zymographic assay. The intensity of the bands were quantified using ImageJ in comparison to DMSO.
Figure 3B:
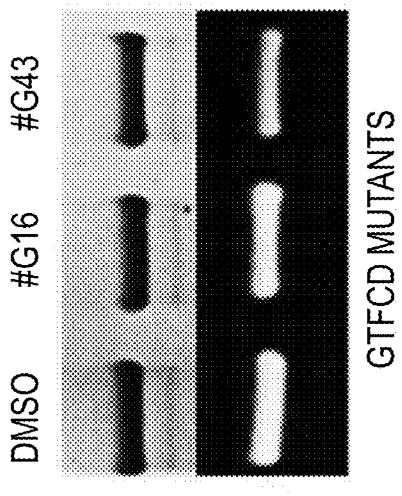
Figure 3C:
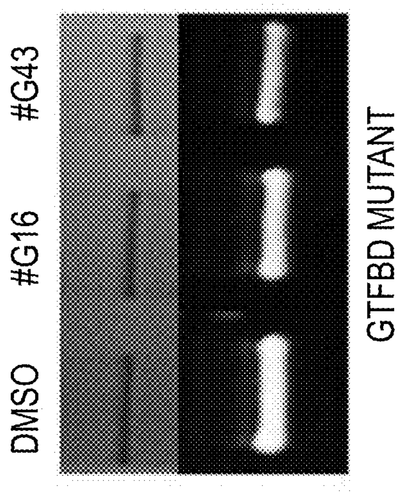

Inhibition of Gtfs by lead compounds. Zymographic enzymatic assay was used to determine whether the lead compounds inhibited the activity of Gtfs that are responsible for the production of glucans and biofilm formation. Supernatants containing Gtf proteins prepared from *S. mutans* bacterial cultures were subjected to SDS-PAGE analysis and zymographic assay. Treatment of the SDS-PAGE gels with lead compounds #G16 and #G43 in a zymographic assay revealed that both #G16 and #G43 drastically reduced the glucan production of the Gtfs, #G43 was more potent (FIG. 3A, bottom panels). The same amount of the protein sample was used as controls and visualized by protein staining (FIG. 3A, top panels). The lead compounds were also tested against individual Gtfs using supernatant proteins harvested from cultures of various double mutants. Compound #G43 consistently inhibited the activity of both GtfB and GtfC (FIGS. 3B and 3C), ImageJ analysis of the intensities suggest 80% inhibition of both enzymes, while compound #G16 had a smaller effect on the activity of GtfB (65% inhibition) and GtfC (72% inhibition) (FIG. 3C). Overall #G43 is more potent than #G16 in inhibiting Gtfs.

Figure 4A:
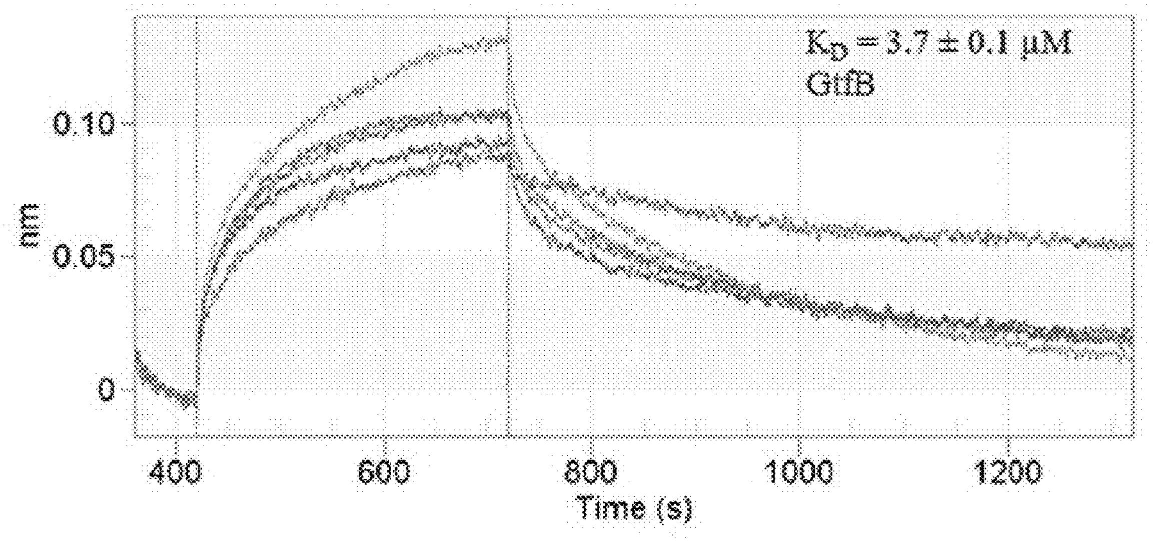
FIGS. 4A-4B show the binding curves of compound #G43 at varying concentrations with (FIG. 4A) GtfB, and (FIG. 4B) FtgC catalytic domain.
Figure 4B:
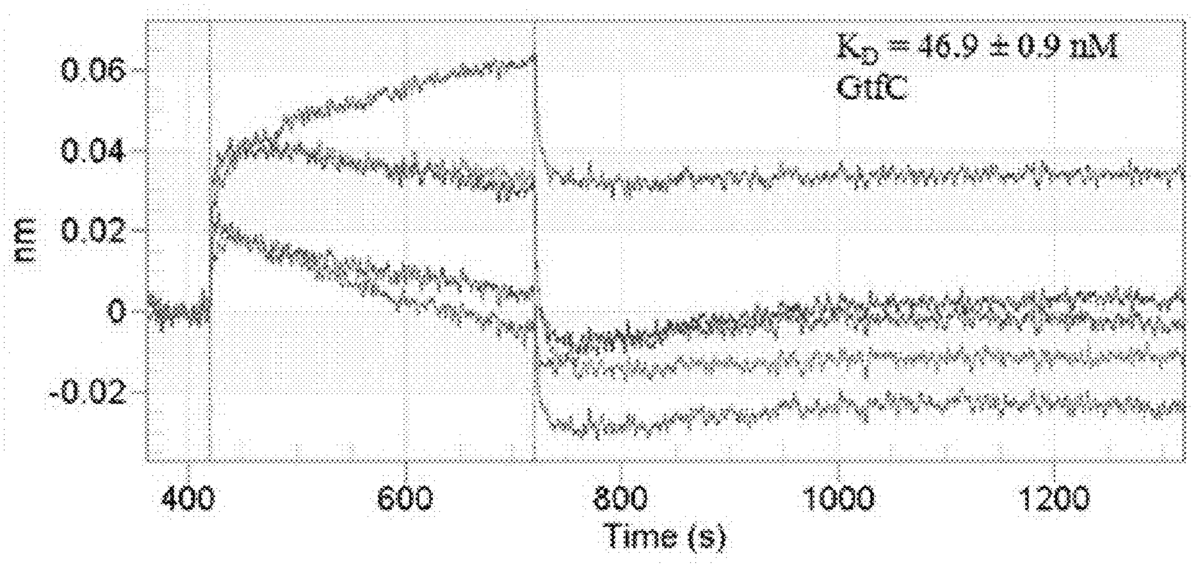

Binding kinetics of #G43 lead compound determined by OctetRed Analysis. Zymograhic assays suggest that the lead compound #43 inhibited the activity of both GtfB and GtfC. To determine if the inhibition is attributed by the binding of the lead compound to the enzymes, the OctetRed96 system was used to characterize protein-small molecule binding kinetics. The his-tagged catalytic domains of GtfB and GtC were immobilized separately onto an anti-penta-HIS (HIS1K) biosensor which consists of high affinity, high specificity penta-his antibody pre-immobilized on a fiber optic biosensor. This sensor was then exposed to varying concentrations of #G43. Assay data fit to a 1:1 binding model with a fixed maximum response, which produced a $K_D$ value of 3.7 μM for GtfB. The $K_D$ value for GtfC was more potent at 46.9 nM (FIGS. 4A and 4B). These data suggest that the lead compound is selective toward GtfC, the protein used in the in-silico analysis. It should be noted that the catalytic domain of GtfC is less soluble compared to that of GtfB's, which may be responsible for the inherent higher off rate of the his-tag from the sensor, leading to a weaker association curve when compared to GtfB. Nevertheless, consistent nanomolar $K_D$ values were obtained from independent experiments.

Figure 5:
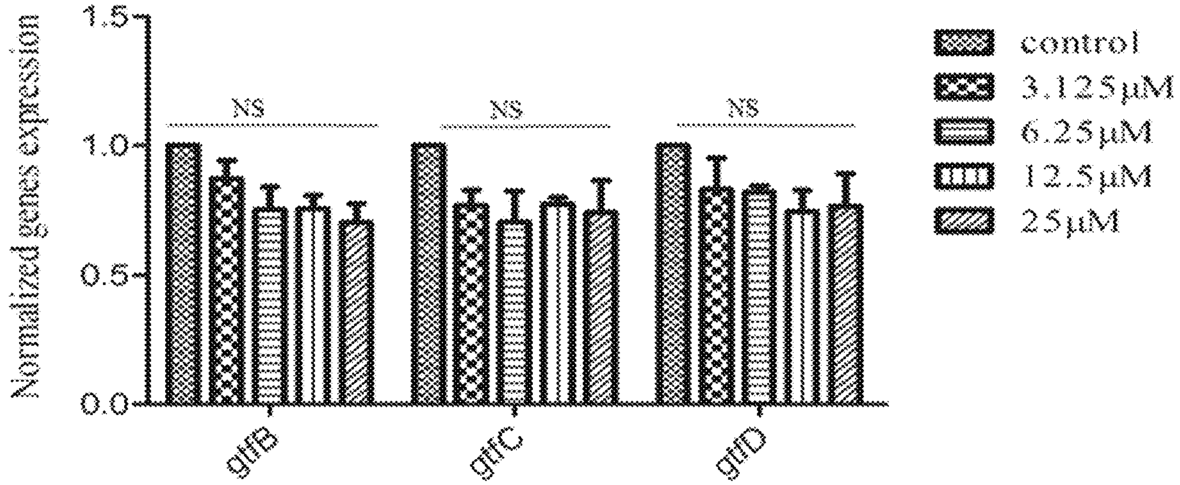
FIG. 5 shows the effect of the compound #G43 on expression of gtfs in *S. mutans* UA159 cells treated with different concentration of #G43 and then harvested and used to prepare RNA. The expression of gtfs was examined by real time RT-PCR. The mRNA expression levels were calibrated by 16S rRNA. Values represent the means±standard deviations from three independent experiments. NS indicates no significant difference between DMSO control and compound-treated groups. The P value>0.05 is considered to be not significant.

Expression of gtfs was not significantly affected by compound #043. The effect of this potent small molecule on the gene expression of gtfs was also examined. The relative expression level of gtfs was evaluated by real time RT-PCR. Compared to the DMSO treated group, expression of gtfs were marginally down-regulated after the treatment with compound #G43 at different concentrations. However, no significant difference was observed between the treated and untreated groups, suggesting that compound #G43 inhibited Gtfs via binding to the targets rather than altered expression of its targeting genes, gtfs (FIG. 5). The most potent compound is not bactericidal and did not inhibit the growth of commensal streptococcal species, and other oral bacteria.

Figure 6A:
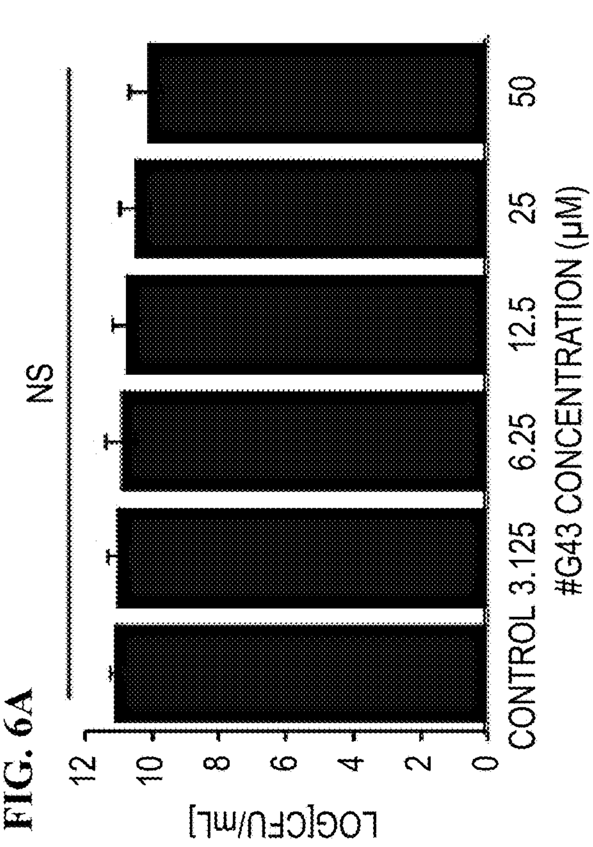
FIG. 6A-6C show effects of the lead compound #G43 on cell viability.
Figure 6B:
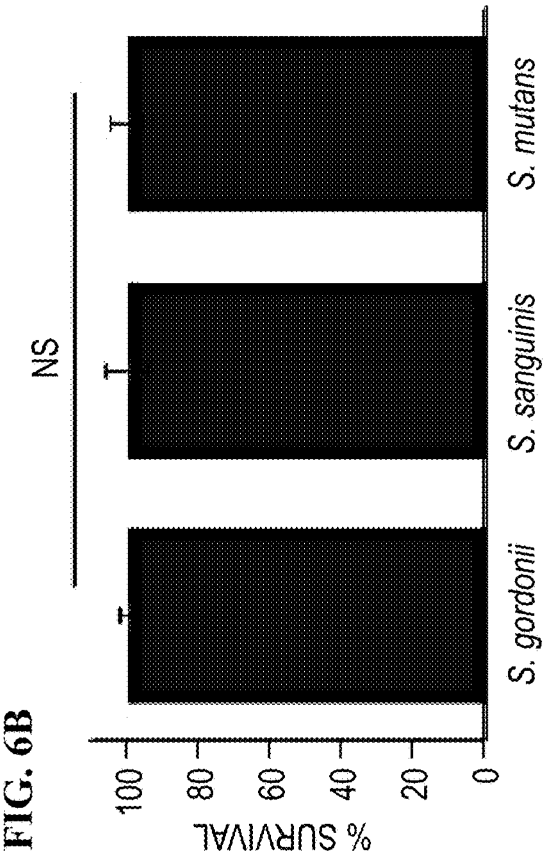
Figure 6C:
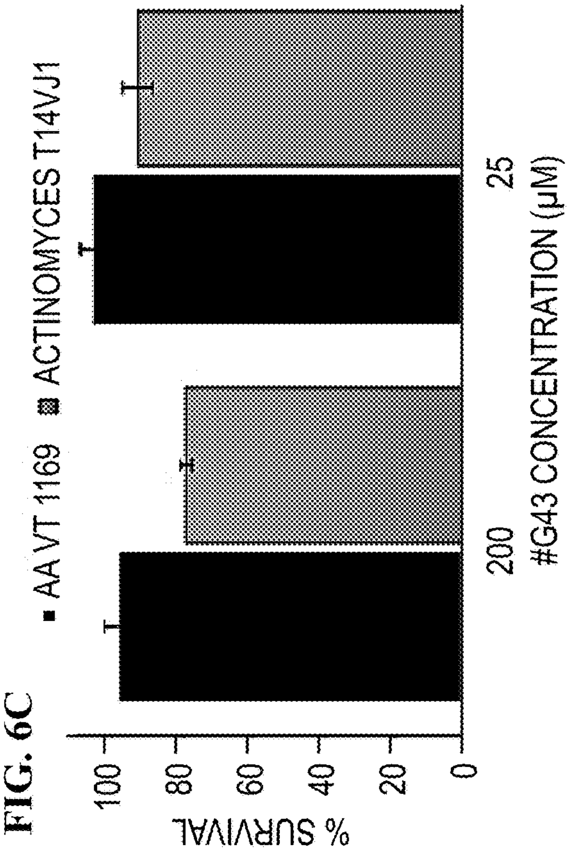

To determine the selectivity of the lead compound toward *S. mutans* biofilm formation versus bacterial growth, effects of the compound on bacterial growth and viability was evaluated. No significant difference in *S. mutans* cell viability was observed between the control group and #G43 treated groups up to 200 μM (FIG. 6A), suggesting that the compound is not bactericidal towards *S. mutans*. This compound was also evaluated for its ability to inhibit two oral commensal streptococci: *S. sanguinis* and *S. gordonii* as the goal was to develop non-bactericidal and species-selective agents. The compound did not have any effect on bacterial growth (FIG. 6B) of both streptococcal species. In addition, we evaluate effects of the compound on other oral bacteria including *Aggregatibacter actinomycetemcomitans* VT1169, a Gram-negative, facultative anaerobe, and *Actinomyces naeslundii* T14VJ1, a gram-positive, facultative anaerobe (FIG. 6C). At 200 μM, the compound had no significant inhibition of *Aggregatibacter actinomycetemcomitans*. Slight inhibition (>20%) was observed of *Actinomyces naeslundii* growth at 200 μM, suggesting the selectivity towards *S. mutans.*

Figure 7A:
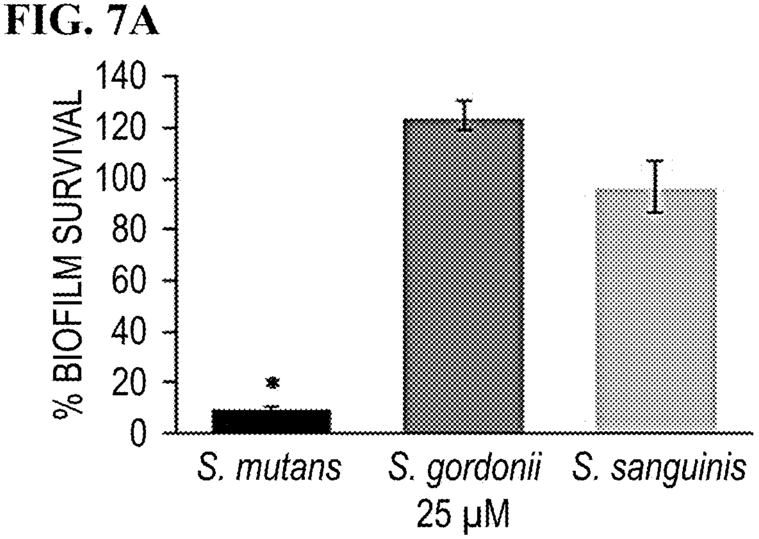
Figure 7B:
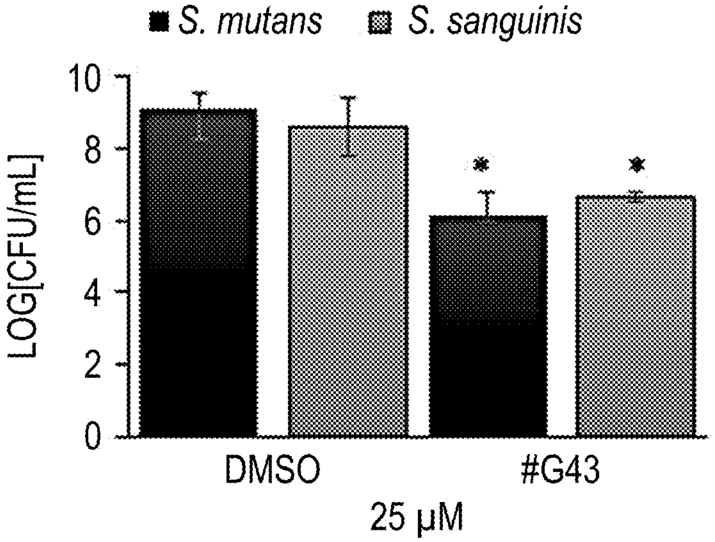
Figure 7C:
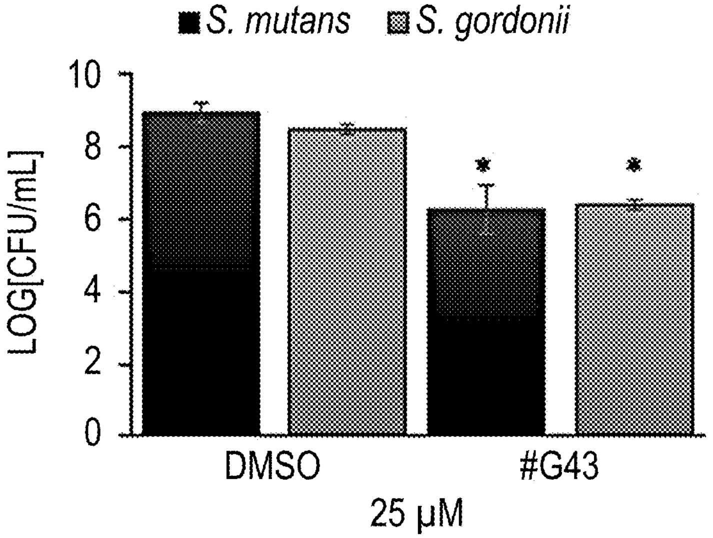

#G43 did not inhibit the biofilm formation by commensal streptococci but inhibit *S. mutans* in the dual species biofilms. To determine the selectivity of the lead compound toward *S. mutans* biofilm formation over the biofilms of other species, effects of the compound was evaluated on the biofilm formation by two oral commensal bacteria: *S. sanguinis* and *S. gordonii*. No significant difference in *S. sanguinis* biofilm formation was observed between the control group and #G43 treated groups up to 200 μM (FIG. 7A). A slight increase in the biofilm formation by *S. gordonii* was observed when treated with the lead compound. Further, experiments using a dual species model was conducted using *S. mutans* with either *S. sanguinis* (FIG. 7B), or *S. gordonii* (FIG. 7C). A reduction in the overall biofilm formation was observed with the treatment of our compound. Moreover, the lead compound shifted the bacterial composition ratio of commensal *streptococcus* to *S. mutans* from untreated 1:4 to either 4:1 for *S. sanguinis*, or 3:2 for *S. gordonii* (FIGS. 7D-7E). FIG. 7F shows tabular results. The increase in commensal bacteria by the treatment again suggests that the lead selectively affected *S. mutans* biofilm.

Docking analysis, the facile synthesis of #G43 and its inactive analog to establish that the ortho primary benzamide moiety is crucial for its potency. To explore the underlying mechanism of #G43's bioactivity, the compound was docked into the active site of GtfC to elucidate plausible interactions. The top docking pose of #G43 within the GtfC active site revealed several key interactions. The nitro group on the benzothiophene ring interacts with Arg540, the amide linker is within close proximity of Gln592, and pi-pi stacking interactions are observed between Trp517 and the benzene ring. Of particular importance is the interaction of the primary ortho amide group on the benzene ring with Glu515, Asp477, and Asp588. While the mechanism of the glucan formation is not fully understood, Glu515, Asp477, and Asp588 are assumed to function as a nucleophile, a general acid/base catalyst, and a stabilizer of the glucosyl intermediate, respectively (Ito, K. et al. Crystal Structure of Glucansucrase from the Dental Caries Pathogen *Streptococcus mutans. J Mol Biol* 408, 177-186 (2011)). Thus, we hypothesized that this functional ortho amide group is crucial for the binding of the compound to the protein.

Figure 8A:
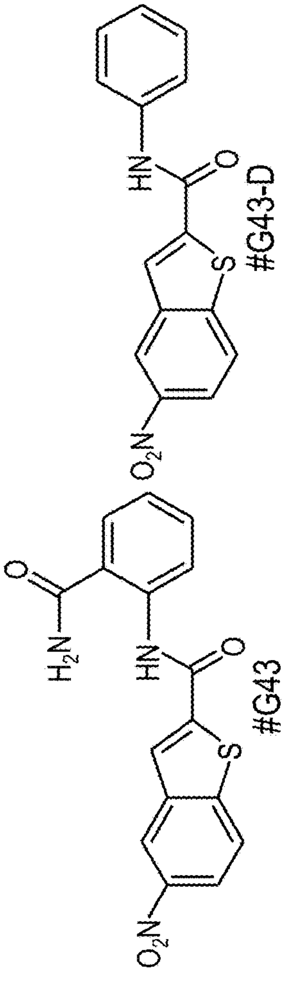
FIGS. 8A-8E show effects of the lead compound #G43 and its inactive analog #G43-D.
Figure 8B:
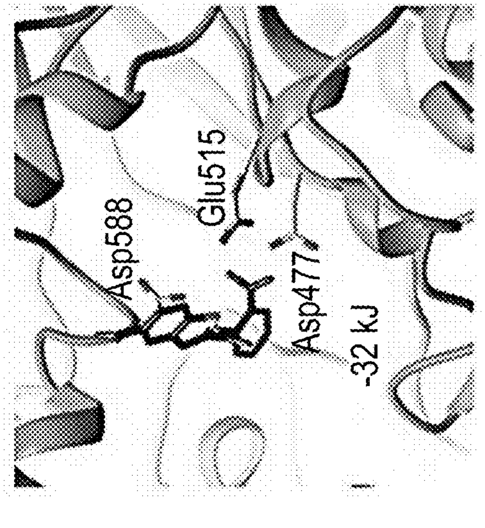
Figure 8C:
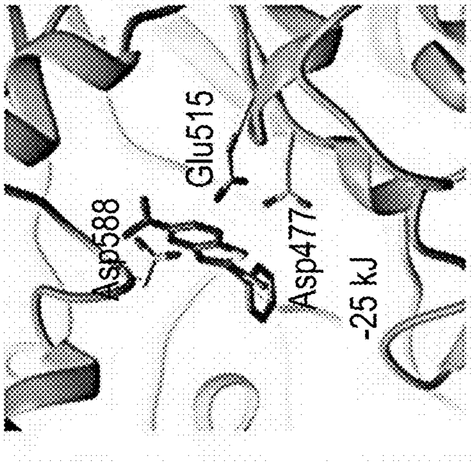
Figure 8D:
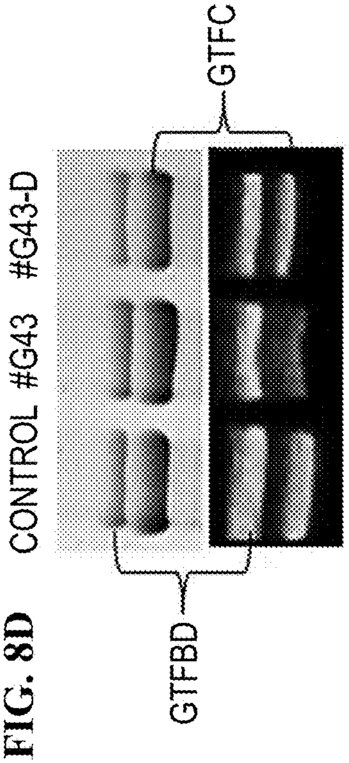
Figure 8E:
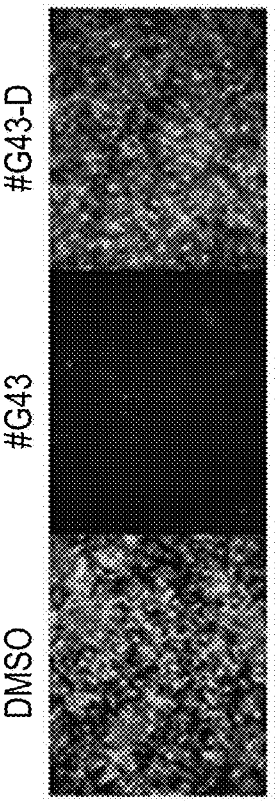

In order to test this, an analog (#G43-D) with a 3D structure (FIG. 8A) that does not contain the primary amide group was designed and subjected it to docking analysis, as a theoretical design. This scaffold failed to produce a good docking score in FlexX (greater than −25 kJ/mol) and yielded a weak binding pose (FIG. 8B). Due to the absence of the primary amide group, the scaffold takes on a different orientation and possesses poor interactions with the active site. The lead compound was re-synthesized in one step using commercially available reagents, anthranlinamide and 5-nitro-1-benzothiophene-2-carboxylic acid, in an excellent yield and fully characterized (described below). We also synthesized the "inactive" analog (#G43-D) in one step by replacing the anthranilinamide with aniline in the EDAC coupling synthesis. Zymographic analysis consistently showed that the lead compound #G43 drastically reduced the glucan bands, especially of those produced by GtfC. However the designed "inactive" compound #G43-D significantly reduced the ability to inhibit the glucan production (FIG. 8D). Additionally, in vitro biofilm assay and fluorescence microscopy revealed that the analog #G43-D did not inhibit *S. mutans* biofilms at concentrations up to 200 μM (FIG. 8E). Binding studies of this analog against GtfB yielded a $K_D$ value of 68 μM, compared to a $K_D$ value of 3.7 μM by the active analog. This data demonstrates that not only is the inhibition of biofilms by selectively targeting Gtfs plausible, but the inclusion of the primary ortho amide group is crucial to maintain potent anti-biofilm activity. Further structure and activity relationship studies are ongoing to improve the potency of #G43.

#G43 reduced *S. mutans* virulence in vivo. To evaluate in vivo efficacy of the lead compound #G43, we tested the compound using a rat model of dental caries (Michalek, S. M., McGhee, J. R., Shiota, T. & Devenyns, D. Virulence of *Streptococcus mutans*: cariogenicity of *S. mutans* in adult gnotobiotic rats. *Infection and Immunity* 15, 466-471 (1977)) (FIG. 9). All rats from the two experimental groups were colonized with *S. mutans*. The bacterial colonization appears to be reduced in #G43 treated rats, however the reduction did not reach the statistically significant difference when compared with the control group. The buccal, sulcal, and proximal surface caries scores of the treated animals were significantly reduced. These data suggest that the lead small molecule selectively targets virulence factors, Gtfs and Gtf-mediated biofilm formation, rather than a simple inhibition of bacterial growth. Furthermore, the #G43 treated rats did not lose weight over the course of the study in comparison with the control group, suggesting that the compound is not toxic.

Dental caries is a multifactorial disease, in which *S. mutans* and other cariogenic species interact with dietary sugars to promote virulence. The current marketed therapies for dental caries and other infectious diseases are non-selective and broad spectrum in nature, which compromises the benefit of commensal bacteria in the oral flora. Thus, we have conducted this study to develop novel small molecule inhibitors selective for key virulence factors of *S. mutans*. As Gtfs are crucial for the biofilm formation and the cariogenicity of *S. mutans*, we conducted an in silico screening of 500,000 drug-like small molecule compounds targeting GtfC and identified top scored scaffolds for in vitro biofilm assays. Seven potent biofilm inhibitors emerged from this study, the lead compound #G43 was further characterized and shown to have anti-biofilm activity through the binding to GtfBC and the inhibition of the activity of GtfBC. The lead compound drastically reduced bacterial virulence in the rat model of dental caries.

In addition, the protein-small molecule binding kinetic analysis of #G43 and GtfBC revealed the lead compound has strong selectivity; it has low micromolar affinity for GtfB and more potent nanomolar affinity for GtfC. Furthermore, compound #G43 selectively inhibited *S. mutans* biofilms in single-species and dual-species biofilm. As the catalytic domain of GtfB and GtfC shares 96% similarity at amino acid sequence level, the selectivity by the compound is remarkable. Since the crystal structure of GtfC/acarbose complex was used for screening and identification of potent lead compounds, this result further demonstrates the validity of this structure-based drug design approach for precision drug discovery. Numerous studies have claimed the identification of natural and synthetic small molecules that inhibit the biofilm formation of *S. mutans* through affecting the gene expression of a variety of biofilm regulatory genes including gtfs (Subramenium, G. A., Vijayakumar, K. & Pandian, S. K. Limonene inhibits streptococcal biofilm formation by targeting surface-associated virulence factors. *Journal of medical microbiology* 64, 879-890, doi:10.1099/jmm.0.000105 (2015); Koo, H. et al. Influence of apigenin on gtf gene expression in *Streptococcus mutans* UA159. *Antimicrobial agents and chemotherapy* 50, 542-546, doi:10.1128/aac.50.2.542-546.2006 (2006); Branco-de-Almeida, L. S. et al. Effects of 7-epiclusianone on *Streptococcus mutans* and caries development in rats. *Planta medica* 77, 40-45, doi:10.1055/s-0030-1250121 (2011); Vahid-Dastjerdi, E., Monadi, E., Khalighi, H. R. & Torshabi, M. Down-Regulation of Glycosyl Transferase Genes in *Streptococcus Mutans* by *Punica granatum* L. Flower and *Rhus coriaria* L. Fruit Water Extracts. *Iranian journal of pharmaceutical research; IJPR* 15, 513-519 (2016)). Many compounds may have indirect effects on the expression of gfs as they can target different signaling and metabolic pathways. None has been shown to have a direct effect on the activity of Gtfs.

Further investigation through docking analysis of this lead compound identified critical interactions of the ortho primary amide group of the compound with key active site residues of GtfC. An analog that does not contain this functional group lost the ability to inhibit the activity of Gtfs and in vitro biofilm formation, demonstrating that these effects are directly related and that the inclusion of the primary ortho amide group is crucial to maintaining potent anti-biofilm activity.

The lead compound contains a nitro group, and typically, nitro groups are not amenable for development of drugs due to the potential of hazardous production of the nitroanion radical, nitroso intermediate, and N-hydroxy derivative (Boelsterli, U. A., Ho, H. K., Zhou, S. & Leow, K. Y. Bioactivation and hepatotoxicity of nitroaromatic drugs. *Current drug metabolism* 7, 715-727 (2006)). However, this is a concern only for systemic drugs and not for topical applications we intend to carry out. Nevertheless, efforts are underway to optimize the activity and explore the removal of such predicted groups. Further, we were encouraged to find that #G43 did not affect the survival rates of *S. mutans* and two commensal streptococcal species up to 200 μM, and did not significantly affect other common oral bacteria such as *Actinomeyes naeslundii* and *Aggregatibacter actinomycetemcomitans*. The non-toxic feature of #G43 was also evident in the rodent caries models as no weight loss was observed in rats.

A recent study also reported the development of a Gtf inhibitor through a similar approach. The observed potency of our lead compound #G43 is slightly better than the previously reported scaffold (Ren, Z. et al. Molecule Targeting Glucosyltransferase Inhibits *Streptococcus mutans* Biofilm Formation and Virulence. *Antimicrobial agents and chemotherapy* 60, 126-135, doi:10.1128/aac.00919-15 (2015)). Further #G43 drastically inhibited cariogenicity in vivo, but did not significantly inhibit *S. mutans* colonization. This is interesting finding as the compound effectively inhibited the biofilm formation by *S. mutans* in vitro. It is possible that the sampling method skewed our results toward the total numbers of *S. mutans* recovered from the oral cavity rather than only the biofilm bacteria. In addition, in vivo inhibition of *S. mutans* glucan production may not be sufficient to inhibit in vivo biofilm formation thus bacterial colonization. This would be a desirable outcome as we can inhibit virulence but minimally affect bacterial colonization and demonstrate a virulence-selective therapeutic approach. Moreover, in contrast to the reported compound, #G43 did not significantly affect the expression of Gtfs. This study also demonstrated that the lead compound selectively binds to GtfC and GtfB, suggesting the impact on the activity of GtfBC by the direct interaction rather than through down-regulation of gene expression of gtfBC.

In conclusion, using structure-based design, a unique low micromolar biofilm inhibitor that targets *S. mutans* Gtfs through binding to key virulence factors, Gtfs, was developed. The compound is drug-like, non-bactericidal, easy to synthesize, and exhibits very potent efficacy in vivo.

Structure-Based 3D Database Search. The crystal structure of the complex of GtfC and acarbose (PDB code: 3AIC)

was used for in silico screening. The GtfC active site was prepared by selecting residues and cofactors (water and MES) within 6.5 Å of acarbose and then a pharmacophore that consists of Asp588 (H-acceptor) and Gln960 (H-donor) was generated. The reliability of the FlexX/LeadIT package was assessed by virtually generating a 3D structure of acarbose using VEGA-Z, and then by docking the structure into the prepared GtfC active site. This resulting docking generated a comparable binding mode to the experimental data. A large library of about 500,000 small molecules obtained in 3D mol2 format from the free-access ZTNC database was used for the in silico screening. Docking runs were performed with a maximum allowed number of 2000 poses for each compound. The produced binding energies were ranked according to the highest scoring conformation. Compounds with binding energies better than −20 kJ/mol were selected for further investigation. The structures of top scoring compounds were examined for their bindings inside the GtfC pocket, drug-like properties based on Lipinski's rules, and for synthetic feasibility.

Bacterial strains, culture conditions, and chemicals. Bacterial strains, including *S. mutans* UA159 and various Gtf mutants as described below, *S. sanguinis* SK36, and *S. gordonii* were grown statically at 37° C. with 5% $C_{102}$ in Todd-Hewitt (TH) broth or on THB agar plate, or in chemically defined biofilm medium supplemented with 1% sucrose (Loo, C., Corliss, D. & Ganeshkumar, N. *Streptococcus gordonii* biofilm formation: identification of genes that code for biofilm phenotypes. J Bacteriol 182, 1374-1382 (2000)). *Aggregatibacter actinomycetemcomitans* VT1169 and *Actinomyces naeslundii* T14VJ1 were grown in Tryptic soy broth with yeast extract (TYE). Small molecule candidates were purchased from either ChemBridge Corporation or Enamine Ltd in USA. Stock solutions were prepared in dimethyl sulfoxide at 10 mM and arrayed in a 96-well format for biological screening.

*S. mutans* biofilm formation and inhibition assays. Biofilm assays using 96-well flat-bottom polystyrene microtiter plates were performed to evaluate *S. mutans* biofilm formation at various conditions of small molecule inhibitors as described (Liu, C., Worthington, R. J., Melander, C. & Wu, H. A new small molecule specifically inhibits the cariogenic bacterium *Streptococcus mutans* in multispecies biofilms. Antimicrobial agents and chemotherapy 55, 2679-2687 (2011); Zhang, Q. et al. New small-molecule inhibitors of dihydrofolate reductase inhibit *Streptococcus mutans*. International journal of antimicrobial agents 46, 174-182, doi: 10.1016/j.ijantimicag.2015.03.015 (2015)). Each assay was replicated three times. Minimum biofilm inhibitory concentration (MBIC) of compounds was determined by serial dilutions. The most active compounds identified from the tested candidates were selected for further examination.

Construction of *S. mutans* Gtfs mutants. GtfB, GtfC single mutant, and GtfBC double mutant in which gtf was replaced with a kanamycin resistance cassette, aphA3 (encoding an aminoglycoside phosphotransferase), were gifts from Dr. Robert Burne's Laboratory, University of Florida, Gainesville, Fla. The GtfD mutant was constructed by an overlapping PCR ligation strategy using an erythromycin resistance cassette isolated from the IFDC2 cassette (Xie, Z., Okinaga, T., Qi, F., Zhang, Z. & Merritt, J. Cloning-independent and counterselectable markerless mutagenesis system in *Streptococcus mutans*. *Appl Environ Microbiol* 77, 8025-8033 (2011)). In brief, a 1-kb DNA fragment upstream of gtfD was PCR amplified with a primer pair of GtfD-UpF1 and GtfD-UpR-ldh, while a 1-kb DNA fragment downstream of gtfD was PCR amplified with a primer pair of GtfD-DnF-erm and GtfD-DnR1. The erythromycin cassette was PCR amplified with a primer pair of ldhF and ermR. With a primer pair of GtfD-UpF and GtfD-DnR, the overlapping PCR was used to amplify the three fragments that contain overlapping regions (primers listed below). The resulting 2.8-kb ΔgtfD/erm amplicon was transformed into *S. mutans* UA159, and transformants were selected on THB plates containing erythromycin after 48 h incubation. The GtfBD and GtfCD double mutants were constructed by transformation of the GtfB and GtfC single mutant with the ΔgtfD/erm amplicon and followed by the selection of kanamycin- and erythromycin-resistant colonies. The in-frame insertion of erm in the place of gtfD for each mutant allele was verified by DNA sequencing analyses. The mutants were further validated by the production of respective Gtf.

Inhibition of the activity of Gtfs determined by zymographic assays. Well established zymographic assay was used to determine enzymatic activity of Gtfs. In brief, overnight *S. mutans* UA159 cultures were diluted 1:100 in fresh 5 mL THB. Bacteria were grown to $OD_{470}$ of 1.0, and spun down by centrifugation at 4° C. and culture supernatants were collected and filtered through a 0.22-μm-pore-size filter membrane to remove residual bacterial cells and dialyzed at 4° C. against 0.02 M sodium phosphate buffer (pH 6.8), with 10 μM phenylmethylsulfonyl fluoride (PMSF), followed by a second dialysis against 0.2 mM sodium phosphate containing 10 μM PMSF. After dialysis, 4 mL of samples were concentrated to 40 μL by 100K Amicon Ultra-4 centrifugal filter (Merk Millipore Ltd.). For electrophoresis and zymographic analysis, 10 μL of each concentrated culture supernatant was applied to 8% SDS-PAGE in duplicate. One gel was used for protein staining with Coomassie blue dye, while the other one was subjected to zymographic assay. For zymogram analysis, following electrophoretic separation, gels were washed twice for 15 min each with renaturing buffer containing 2.5% Triton X-100. Gels were then incubated for 18 h at 37° C. with 0.2 M sodium phosphate buffer (pH 6.5) containing 0.2% dextran T70, 5% sucrose, and varying concentrations of the small molecule inhibitors. The reactions were stopped by washing gels with distilled water at 4° C. for 10 min, and digital images of the resultant white opaque glucan bands were visualized against a black background and captured using a digital camera.

Expression and purification of GtfB and GtfC catalytic domains. The DNA fragment coding for either GtfB catalytic (residues 268 aa-1074 aa) or GtfC-catalytic (residues 295 aa-1103 aa) was PCR amplified with primer sets of GtfB-BamH1-F and GtfB-Xho1-R, GtfC-BamH1-F and GtfC-Xhol1-R respectively using *S. mutans* genomic DNA as a template. Each amplified fragment was cloned into pET-sumo vector respectively and transformed in *Escherichia coli* BL21(DE3). The recombinant strain grown to $OD_{600}$=0.8 in LB medium was induced with 0.1 mM IPTG at 18° C. overnight. Cell lysates prepared form the overnight grown *E. coli* cells were subjected to protein purification using HiTrap™ Column ($Ni^{2+}$ affinity) followed by gel filtration experiments as described (Zhu, F. et al. Structural and functional analysis of a new subfamily of glycosyltransferases required for glycosylation of serine-rich streptococcal adhesins. *The Journal of biological chemistry* 286, 27048-27057, doi:10.1074/jbc.M110.208629 (2011); Zhang, H. et al. The highly conserved domain of unknown function 1792 has a distinct glycosyltransferase fold. *Nature* communications 5, 4339, doi:10.1038/ncomms5339 (2014)).

Octet Red analysis. Octet full kinetic binding analysis was performed for binding of #G43 to GtfB and GtfC. The rate constant, KD, was determined using the Octet® Red96 system (ForteBio, Menlo Park, Calif.). Phosphate buffer with 3.5% (w/v) DMSO was used. The proteins were captured on dip-and-read Anti-Penta-HIS (HIS1K) Biosensor. These consist of high affinity, high specificity Penta-His antibody from Qiagen pre-immobilized on a fiber optic biosensor. The binding of #G43 at 3-fold serial dilutions in phosphate buffer from 200, 66.6, 22.2, 7.4, 2.5 to 0 μM was assessed. The ForteBio Octet analysis software (ForteBio, Menlo Park, Calif.) was used to generate the sensorgram and the accuracy of the analysis.

Cell viability of *S. mutans, S. gordonii, S. sanguinis, Aggregatibacter actinomycetemcomitans* and *Actinomyces*. Effects of lead small molecules on cell viability were examined as described (Liu, C., Worthington, R. J., Melander, C. & Wu, H. A new small molecule specifically inhibits the cariogenic bacterium *Streptococcus mutans* in multispecies biofilms. *Antimicrobial agents and chemotherapy* 55, 2679-2687 (2011)). The number of colony-forming units (CFU) per milliliter of each sample treated with selected compounds at different concentrations was enumerated after incubation for 24 h at 37° C. and compared to the values obtained from the DMSO control group. Overnight broth cultures were transferred by 1:50 dilutions into fresh THB medium and were allowed to grow until mid-exponential phase ($OD_{470}$ nm 0.6) before transfer to 96-well plates containing desired concentration of the compound. After 16 h incubation, bacterial growth was measured at $OD_{470}$, and normalized to the DMSO control (100%).

Growth of commensal and dual-species biofilms. Overnight broth cultures were transferred by 1:50 dilutions into fresh THB medium and were allowed to grow until mid-exponential phase (OD470 nm=0.6) before transfer to 96-well plates. For mono-species biofilms, 1:100 dilution of the individual cultures was added to the 96-well plate containing the desired concentration of compound or DMSO. After incubation for 16 h, the biofilms were gently washed with PBS in triplicate and the biofilms were quantified with crystal violet staining. For dual-species biofilms, 1:100 dilution of *S. mutans* was used and 1:10 dilution of the commensal species (*S. sanguinius* or *S. gordonii*) was used as inoculum to seed the 96-well plate containing the desired concentration of compound or DMSO. After incubation for 16 h, the biofilms were scratched off with a sterile spatula and suspended in 100 μL of PBS, the biofilm samples were vortexed. To determine the total number of viable bacterial cells (colony forming units, CFU), 100 μl from dispersed, 16 h biofilms were serially diluted in potassium phosphate buffer and plated in duplicate on BAP. The commensal species could be differentiated from *S. mutans* due to their characteristic green rings.

Rat model of dental caries. *S. mutans* in vivo colonization and virulence were evaluated using a rat model of dental caries as previously described (Crowley, P. J., Brady, L. J., Michalek, S. M. & Bleiweis, A. S. Virulence of a spaP Mutant of *Streptococcus mutans* in a Gnotobiotic Rat Model. *Infection and Immunity* 67, 1201-1206 (1999)). Fischer 344 rats were bred and maintained in trexler isolators. Rat pups were removed from isolators at 20 days of age and randomly assigned into two groups of 6 animals with or without treatment of the potent inhibitor #G43. Rats were then infected with *S. mutans* UA159 for three consecutive days and provided a caries-promoting Teklad Diet 305 containing 5% sucrose (Harlan Laboratories, Inc., Indianapolis, IN.) and sterile drinking water ad libitum. One group of rats was then treated with vehicle control while another group was topically treated with the lead compound at 100 μM twice daily for 4 weeks beginning 10 days post infection. Following each treatment, drinking water was withheld for 60 min. Animals were weighed at weaning and at the termination of the experiment. The animals were euthanized, their mandibles excised for microbiological analysis of plaque samples on MS agar plates and BAP and for scoring of caries by the method of Keyes (Keyes, P. H. Dental caries in the molar teeth of rats. II. A method for diagnosing and scoring several types of lesions simultaneously. *Journal of dental research* 37, 1088-1099 (1958)). All experimental protocols were approved by University of Alabama at Birmingham Institutional Animal Care and Use Committee. The methods were carried out in accordance with the relevant guidelines and regulations.

The analysis of the in vitro experimental data was performed by ANOVA and Student's t test using SPSS 11.0 software (SPSS Inc., Chicago, IL.). Statistical significance in mean caries scores, colony-forming units (CFU) per mandible and body weights between two groups of rats was determined by one-way ANOVA with the Tukey-Kramer multiple comparison test using the InStat program (Graphpad Software). Differences were considered to be significant when a value of P≤0.05 was obtained.

Primers used in this stud include the following, listed in 5' to 3' order.

```
gtfD-UpF1
                                        (SEQ ID NO: 1)
TTAGCATGATTGGGGCTGC

gtfD-UpR-ldh
                                        (SEQ ID NO: 2)
TTGTTCATGTAATCACTCCTTCGATAACATATACGTTACAAAC

gtfD-DnF-erm
                                        (SEQ ID NO: 3)
GGTATACTACTGACAGCTTCCACTGACATAGCTTAACGTG

gtfD-DnR1
                                        (SEQ ID NO: 4)
GACAAACATACCTTAGACGC

ldhF
                                        (SEQ ID NO: 5)
AAGGAGTGATTACATGAACAA

ermR
                                        (SEQ ID NO: 6)
GAAGCTGTCAGTAGTATACC
```

Used for Real-Time RT-PCR

```
16s rRNA-UpF
                                        (SEQ ID NO: 7)
CCTACGGGAGGCAGCAGTAG

16s rRNA-DnR
                                        (SEQ ID NO: 8)
CAACAGAGCTTTACGATCCGAAA

gtfB-UpF
                                        (SEQ ID NO: 9)
CATACAGTAACGACAATCAGTAGCTCTA

gtfB-DnR
                                       (SEQ ID NO: 10)
GTACGAACTTTGCCGTTATTGTCATA
```

-continued

```
gtfC-UpF
                                       (SEQ ID NO: 11)
GCCACGGAACAAGCAGTTCTGTAA

gtfC-DnR
                                       (SEQ ID NO: 12)
TAATACCAATTATTTCCTAAGCTAA

gtfD-UpF2
                                       (SEQ ID NO: 13)
CACAGGCAAAAGCTGAATTAACA

gtfD-DnR2
                                       (SEQ ID NO: 14)
GAATGGCCGCTAAGTCAACAG
```

Reactions were monitored with thin layer chromatography (TLC), which was done on silica gel plates with fluorescent indicator (Whatmann, silica gel, UV254, 25 μm plates). The TLC spots were observed under UV light with the wavelengths 254 nm and 365 nm. Melting points were determined on a Mel-Temp II melting point apparatus and were uncorrected. Proton nuclear magnetic resonance ($^{1H}$NMR) and carbon nuclear magnetic resonance ($^{13}$CNMR) spectra were recorded on Bruker DPX 300 spectrometers using TMS or appropriate solvent signals as internal standard. The values of chemical shift are given in parts per million (ppm) relative to tetramethylsilane and coupling constants (J) in Hz. Mass spectra were recorded on an Applied Biosystems 4000 Q Trap instrument. Anhydrous solvents used for reactions were purchased in Sure-Seal™ bottles from Aldrich Chemical Company. Other reagents were purchased from Aldrich, Lancaster or Acros chemical companies and used as received.

Figure 10B:
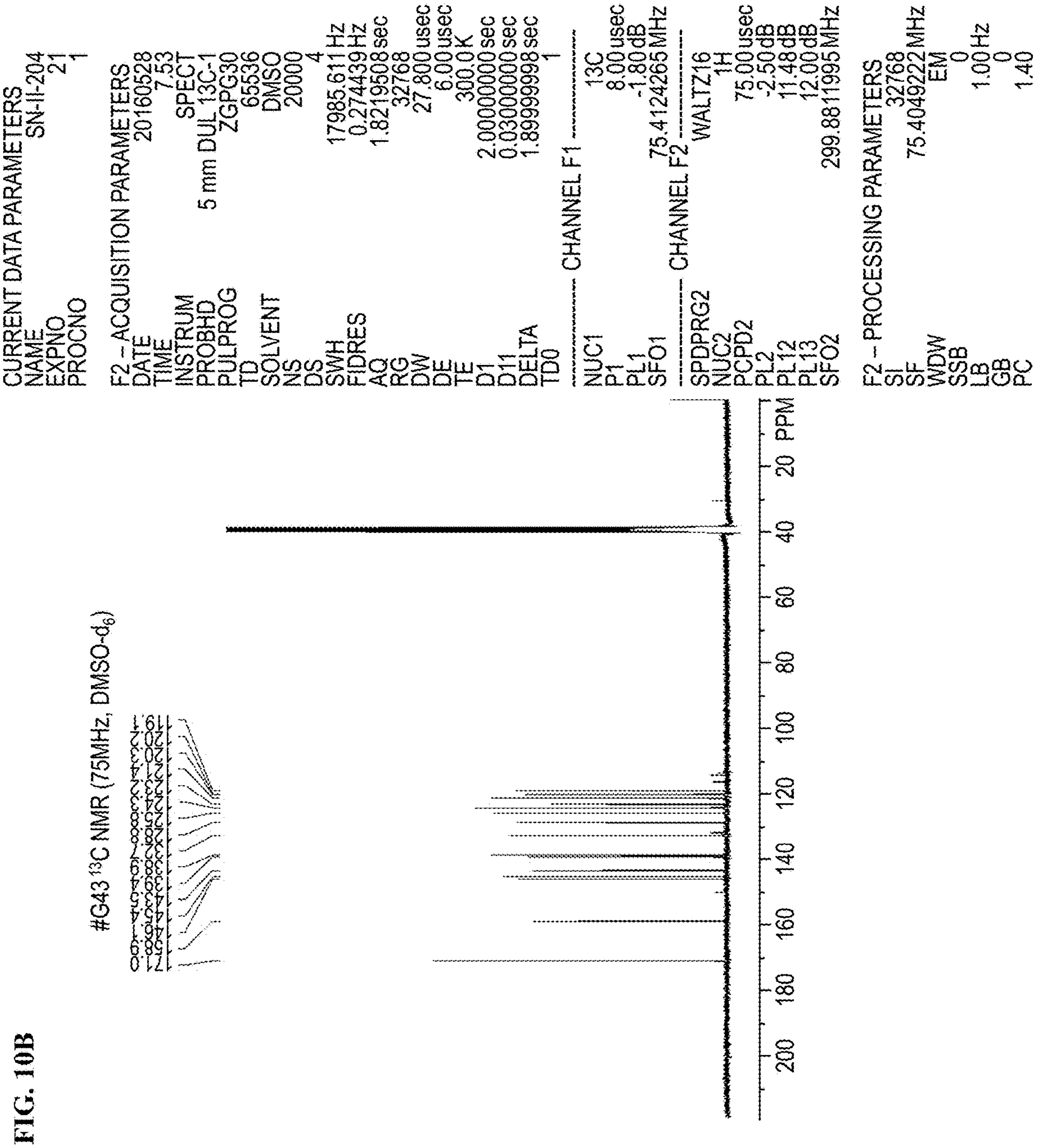

Protocols used to synthesize the lead compound and its subsequent derivatives are (#G43) 5-nitro-1-benzothiophene-2-carboxylic acid (535 mg, 2.4 mmol), anthranlinamide (300 mg, 2.2 mmol), EDAC (630 mg, 2.2 mmol), and DMAP (26 mg, 0.22 mmol) were dissolved in dichloromethane (15 mL) and the mixture was let stir overnight. TLC examination using 10% MeOH in $CH_2Cl_2$ showed the completion of the reaction. The reaction mixture was diluted with $CH_2Cl_2$ (20 mL), washed with water (3×20 mL), brine (1×20 mL) and dried over sodium sulfate. Removal of the drying agent followed by the evaporation of solvent gave the crude product which was filtered and washed with dichloromethane and hexane to afford the pure product as a bright orange solid (654 mg, 80%), mp. 401-402° C.; (FIG. 10A) $^1$H NMR (300 MHz, DMSO-$d_6$) δ: 7.23 (t, 1H, J=7.6 Hz), 7.59 (t, 1H, J=7.8 Hz), 7.96-7.93 (m, 2H), 8.37-8.254 (m, 3H), 8.51 (s, 1H), 8.58 (d, 1H, J=7.8 Hz), 9.03 (d, 1H, J=2.1 Hz), 13.336 (s, 1H). (FIG. 10B)$^{13}$C NMR (75 MHz, DMSO-$d_6$) δ: 119.1, 120.2, 120.4, 121.4, 123.23, 124.34, 125.88, 128.8, 132.71, 138.9, 139.4, 145.5, 146.1, 158.9, 171.0. M/Z=325.1[M−$NH_3$]$^+$.

(#G43-D) 5-nitro-1-benzothiophene-2-carboxylic acid (535 mg, 2.4 mmol), aniline (225 mg, 2.2 mmol), EDAC (630 mg, 2.2 mmol), and DMAP (26 mg, 0.22 mmol) were dissolved in $CH_2Cl_2$ (15 mL) and the mixture was let stir overnight. TLC examination using 10% MeOH in $CH_2Cl_2$ showed the completion of the reaction. The reaction mixture was diluted with dichloromethane (20 mL), washed with water (3×20 mL), brine (1×20 mL) and dried over sodium sulfate. Removal of the drying agent gave the crude product which was filtered and washed with dichloromethane and hexane to afford the pure product as a bright orange solid (350 mg, 52%); mp. 224-226° C., (FIG. 11A) $^1$H NMR (300 MHz, $CDCl_3$): δ 13.26 (s, 1H), 8.58 (d, 1H, J=8.4 Hz), 8.49 (s, 1H), 8.10-7.93 (m, 5H), 7.62-7.48 (m, 3H), 7.19 (t, 1H J=6.9). (FIG. 11B)$^{13}$C-NMR (75 MHz, $CDCl_3$): δ 171.60, 160.14, 140.99, 140.41, 140.17, 139.43, 133.21, 129.29, 127.24, 126.07, 125.70, 125.61, 123.44, 123.40, 120.49, 119.41. M/Z=[280.2]$^+$.

Example 3: Hydroxychalcone Inhibitors of *Streptococcus mutans* Glucosyl Transferases and Biofilms as Potential Anticaries Agents

*Streptococcus mutans* has been implicated as the major etiological agent in the initiation and the development of dental caries due to its robust capacity to form tenacious biofilms. Ideal therapeutics for this disease aim to selectively inhibit the biofilm formation process while preserving the natural bacterial flora of the mouth. Several studies have demonstrated the efficacies of flavonols on *S. mutans* biofilms and have suggested the mechanism of action through their effect on *S. mutans* glucosyltransferases (Gtfs). These enzymes metabolize sucrose into water insoluble and soluble glucans, which are an integral measure of the dental caries pathogenesis. Numerous studies have shown that flavonols and polyphenols can inhibit Gtf and biofilm formation at millimolar concentrations. This study screened a group of 14 hydroxychalcones, synthetic precursors of flavonols, in an *S. mutans* biofilm assay. Several of these compounds emerged to be biofilm inhibitors at low micromolar concentrations. Chalcones that contained a 3-OH group on ring A exhibited selectivity for biofilm inhibition. Moreover, 6 additional analogs of the lead compound were synthesized and evaluated for their potential activity and selectivity against *S. mutans* biofilms. The most active compound identified from these studies had an $IC_{50}$ value of 44 μM against biofilm and $MIC_{50}$ value of 468 μM against growth displaying >10 fold selectivity inhibition towards biofilm. The lead compound displayed a dose dependent inhibition of *S. mutans* Gtfs. The lead compound also did not affect the growth of two commensal species (*Streptococcus sanguinis* and *Streptococcus gordonii*) at least up to 200 μM, indicating that it can selectively inhibit cariogenic biofilms, while leaving commensal and/or beneficial microbes intact. Thus non-toxic compounds have the potential utility in public oral health regimes.

Dental caries is a multifactorial disease evident by localized destruction of susceptible dental surfaces. *S. mutans* is the primary etiological agent. Through the function of its Gtfs, *S. mutans* metabolizes sucrose into water insoluble and soluble glucans. Three types of Gtfs are reported: GtfB, GtfC, and GtfD. Both GtfB and GtfC predominantly synthesize water-insoluble glucans whereas GtfD synthesizes water-soluble glucans. These exopolymeric glucans are an integral measure of the cariogenic biofilms that provide an extracellular matrix, shielding the bacteria from the host immune responses, mechanical stresses, and antimicrobial agents. As *S. mutans* accumulate, the bacterium and other cariogenic species within the biofilm undergo active sugar metabolisms and produce copious amounts of their end-product, lactic acid, leading to the dissolution of the hydroxyapatite crystal lattice of the enamel (Lenander-Lumikari, M., Loimaranta, V., Advances in dental research, 2000, 14, 40).

Current preventive approaches for dental caries include tooth-brushing and the use antimicrobial mouthwashes. Unfortunately, the removal of bacterial biofilms through brushing demands frequent repetition because the tooth surfaces are rapidly re-colonized by bacteria. Furthermore, the drawback of existing antimicrobial mouthwashes lies in their lack of selectivity, affecting pathogenic species as well as commensal beneficial species, which give rise to some undesired side effects. Therefore, emerging innovative approaches of dental caries prevention need to be selective and should strive to preserve the natural bacterial flora in the mouth.

*S. mutans* mutants defective in genes gtfB and gtfC, which express GtfB and GtfC respectively, exhibited markedly reduced levels of smooth surface caries lesion compared to the parental *S. mutans* (Yamashita, Y., Bowen, W. H., Burne, R. A., Kuramitsu, H. K., Infection and immunity, 1993, 61, 3811). Thus, *S. mutans* Gtfs are valid targets for the discovery of inhibitors of cariogenic biofilms, which will have potential applications in the treatment of dental caries.

Efforts have been placed in search for *S. mutans* biofilm inhibitors by several research groups (Nijampatnam, B., Nadkarni, D. H., Wu, H., Velu, S. E., Microorganisms, 2014, 2, 128; Peng, X., Zhang, Y., Bai, G., Zhou, X., Wu, H., Molecular microbiology, 2015, 99, 945; Liu, C., Worthington, R. J., Melander, C., Wu, H., Antimicrobial agents and chemotherapy, 2011, 55, 2679; Zhang, Q., Nguyen, T., McMichael, M., Velu, S. E., Zou, J., Zhou, X., Wu, H., International journal of antimicrobial agents, 2015, 46, 174). Since diet is one of the key factors that define oral health, research has mainly been focused on widely consumed food products. Numerous studies have been conducted comparing the efficacies of flavonols and low-molecular-weight polyphenols found in cranberries. Flavones and flavonols were inhibitors of Gtfs; of these, a compound called apigenin (4',5,7-trihydroxyflavone, FIG. 1) was the most effective inhibitor of Gtfs (Koo, H., Hayacibara, M. F., Schobel, B. D., Cury, J. A., Rosalen, P. L., Park, Y. K., Vacca-Smith, A. M., Bowen, W. H., The Journal of antimicrobial chemotherapy, 2003, 52, 782). Flavonols and their glycosides such as myricetin and myricetin 3-rhamnoside exhibited significant but moderate effects (FIG. 1) (Koo, H., Rosalen, P. L., Cury, J. A., Park, Y. K., Bowen, W. H., Antimicrobial agents and chemotherapy, 2002, 46, 1302; Gregoire, S., Singh, A., Vorsa, N., Koo, H., Journal of applied microbiology, 2007, 103, 1960). In addition, scaffolds found in tea (*Camellia sinensis*) that inhibit *S. mutans* biofilms attract attention due to their unique polyphenol compositions and their prevalence in the human diet. Early studies were carried out on extracts containing multiple constituents however recent reports focus on effects of single defined component in vitro and in vivo (Koo, H., Duarte, S., Murata, R., Scott-Anne, K., Gregoire, S., Watson, G., Singh, A., Vorsa, N., *Caries Res,* 2010, 44, 116). Furthermore, these natural product compounds inhibited *S. mutans* biofilms at high micromolar and even millimolar concentrations.

Undoubtedly, flavonols are a promising class of scaffolds for the development of anticaries therapeutics as they may selectively inhibit the formation of cariogenic biofilms. By targeting *S. mutans*' virulence instead of its viability, the agents developed will be non-bactericidal, preserving the natural bacterial flora of the mouth, and will also be less likely to develop resistance to therapy. Encouraged by reported findings on flavonols, we were interested to examine the effect of hydroxychalcones (FIG. 1), precursors of flavonols and isoflavonols, for their effect on *S. mutans*. biofilm and Gtfs. Chalcones were originally isolated from natural sources and are abundant in edible plants. Structurally, they can be defined as open-chain flavonoids in which two aromatic rings are joined by a three carbon α,β-unsaturated carbonyl system. Being a minor subgroup of the flavonoid family, like other members, chalcones have been reported responsible for a variety of biological activities, including antiviral, anticancer, antimicrobial, anti-inflammatory, antioxidative, antimalarial, anti-leishmania, antinociceptive, and antiproliferative activities (Matos, M. J., Vazquez-Rodriguez, S., Uriarte, E., Santana, L., Expert opinion on therapeutic patents, 2015, 25, 351; Das, M., Manna, K., Journal of toxicology, 2016, 7651047). Hence, chalcones are considered to be a class of compounds with important therapeutic potential. There are no studies that report the antibiofilm activity of chalcones against *S. mutans*. This study investigated this class of compounds to identify novel selective anti-biofilm agents that can have potential applications in dental caries prevention.

Although the inhibition of both GtfB and GtfC are required for the maximum reduction in biofilm formation, only the structural information of GtfC's active site is currently known. However, genes encoding these two Gtfs have a very similar amino acid composition (76% homology), and are subject to the same regulatory processes (Hamada, S., Horikoshi, T., Minami, T., Kawabata, S., Hiraoka, J., Fujiwara, T., Ooshima, T., Infection and immunity, 1991, 59, 4161). Thus, GtfC was used as a target for the drug discovery efforts. Initial docking analysis was performed using FlexX/LeadIT package against GtfC active site (resolution: 3.11 Å, PDB code: 3AIC) on a polyphenol database which included various scaffolds such as flavonols, chalcones, stilbenes, and other complex structures. Of these compounds, chalcones were a focus due to their properties discussed above. A total of 14 chalcones with various hydroxyl substitution patterns were obtained from National Cancer Institute (NCI) compound library and screened for their effect on *S. mutans* growth and its biofilm. Table 6 summarizes the results of the preliminary screen conducted at 200 μM.

TABLE 6

Biofilm and growth inhibition profiles of chalcone derivatives obtained from the NCI library.

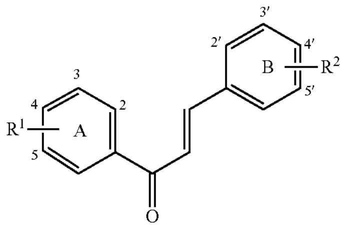

| Compound No | NSC code | $R^1$ | $R^2$ | Biofilm inhibition 200 μM (%)[a] | Growth inhibition 200 μM (%)[a] | *S. mutans* Biofilm $IC_{50}$ (μM)[a] | *S. mutans* Growth $IC_{50}$ (μM)[a] |
|---|---|---|---|---|---|---|---|
| 1 | 73255 | 2-OH | 4'-OH | 27 ± 5 | 48 ± 8 | NA | NA |
| 2 | 73257 | 2-OH | 3'OH | 84 ± 3 | 86 ± 0.5 | 64 ± 4 | 32 ± 0.3 |
| 3 | 46672 | 2,5-di-OH | 4'-OMe | 87 ± 8 | 76 ± 0.9 | NA | NA |
| 4 | 94615 | 2-OH | 4'-OH, 3'-OMe | 86 ± 2 | 85 ± 0.6 | 61 ± 2 | 44 ± 3 |
| 5 | 401492 | 2,4-di-OH | H | NI | NI | NA | NA |
| 6 | 636790 | 2,4-di-OH | 2'-OH | NI | NI | NA | NA |

TABLE 6-continued

Biofilm and growth inhibition profiles of chalcone derivatives obtained from the NCI library.

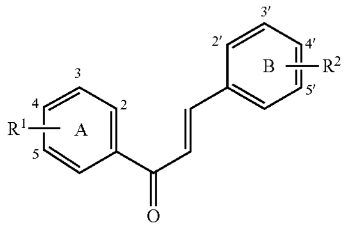

| Compound No | NSC code | $R^1$ | $R^2$ | Biofilm inhibition 200 µM (%)[a] | Growth inhibition 200 µM (%)[a] | *S. mutans* Biofilm $IC_{50}$ (µM)[a] | *S. mutans* Growth $IC_{50}$ (µM)[a] |
|---|---|---|---|---|---|---|---|
| 7 | 636810 | 3-OH | 2'-OH | NI | NI | NA | NA |
| 8 | 640543 | 3-OH | 2'-OH, 3',5' di-Cl | 81 ± 2 | 82 ± 2 | NA | NA |
| 9 | 17051 | 3-OH | 2,4'-di-OH | 93 ± 1 | NI | 32 ± 5 | NI |
| 10 | 90932 | 4-OH | 3',4',5'-tri-OMe | NI | NI | NA | NA |
| 11 | 640536 | 4-OH, 5-OMe | 2'-OH | 85 ± 3 | 71 ± 5 | 34 ± 2 | 40 ± 5 |
| 12 | 677786 | 4-OH, 3-$NMe_2$, 5-$NMe_2$ | 4'-OMe | NI | NI | NA | NA |
| 13 | 196539 | 4-OMe, 5-OMe, | 4'-OMe, 3'-OH | 27 ± 4 | 30 ± 0.7 | NA | NA |
| 14 | 196540 | 4,5-$OCH_2O$ | 4'-OMe, 3'-OH | NI | NI | NA | NA |

[a]Average of at least 5 measurements;
NI No inhibition;
NA Not available.

The initial screen highlighted chalcone activities ranging from almost complete inhibition of both *S. mutans* growth and biofilm (Compounds 2-4, 8, 11), selective inhibition of *S. mutans* biofilm (Compound 9), to no effect on either *S. mutans* growth or biofilm (Compounds 5-7, 10, 12, 14). Active compounds inhibited biofilm in the range of 27-95% at 200 µM concentration. However, several of these compounds also proportionally affected the growth of *S. mutans*, indicating that these small molecules may not be selective biofilm inhibitors. Nonetheless, four compounds that showed promise by exhibiting greater than 80% biofilm inhibition were pursued further into serial dilutions in order to determine their bactericidal and anti-biofilm $IC_{50}$ values, and to observe if any selectivity for biofilm inhibition over growth inhibition arises at lower doses. Both the growth and biofilm $IC_{50}$ values remained in the low micromolar ranging from 32-64 µM. While compounds 2, 4, and 11 failed to demonstrate biofilm-selective inhibition, compound 9 did elicit selectivity with biofilm $IC_{50}$ value 32 µM, without affecting the growth of *S. mutans* at 200 µM concentration. Through this study, we observed several trends in the elicited biofilm and bactericidal effects in relation to chalcone structures.

Chalcones that did not possess any bactericidal or anti-biofilm properties also did not have any OH groups on the ring B of the chalcone skeleton (Compound 5). Despite containing methyl protected hydroxyl groups on the ring B, compounds 10 and 12 also failed to produce any biofilm inhibition. The only analogs that do not contain free hydroxyl groups on the ring A are compounds 13 and 14, which contain methoxy and methylenedioxy groups in the $4^{th}$ and $5^{th}$ positions. While compound 13 was marginally active, reducing biofilm and growth by 30% at 200 µM, compound 14 exhibited no anti-biofilm effects. These results suggest that the presence of hydroxyl groups on either ring of the chalcone scaffold is crucial for the inhibition of *S. mutans* biofilm.

Compounds 5 and 6 differ only in the 2' position of OH group in ring A, where the latter contains an OH group in place of hydrogen. Interestingly, both compounds are inactive, suggesting the OH in 2' position may not contribute to the studied bioactivities. While compound 7 also follows this pattern of activity, this effect is not observed in the case of compound 11.

Furthermore, analysis of compounds 1-4 which contain an OH group at the $2^{nd}$ position of ring A seemed to exhibit potent anti-biofilm and bactericidal activities. Contrary to these compounds, chalcones that bare a hydroxyl group at the $3^{rd}$ position of ring A (Compounds 7-9) seemed to exhibit a range of potent and selective anti-biofilm activities. With the exception of the inactive compound 7, other compounds exhibited greater than 81% inhibition of biofilm at 200 µM and presented some selectivity over growth inhibition. Strikingly, when tested at lower concentrations, the best compound that emerged from this study (9) almost exclusively inhibited *S. mutans* biofilm, suggesting the importance of OH group in the $3^{rd}$ position in the ring A.

There was only one compound that contained a mono-hydroxyl group at the $4^{th}$ position of the ring A (compound 11). This compound was inactive against both *S. mutans* growth and biofilm. Compounds 5-6, 10-14 contain OH group at the 4, position and majority of these compounds also fared poorly in the preliminary screen asides from compound 11 which was toxic to *S. mutans* at low micromolar concentrations. The importance of OH group at this position remains unclear and warrants further investigation.

In search of compounds that selectively target *S. mutans* biofilm without affecting the its growth, the best candidate to pursue further was compound 9, which has a biofilm $IC_{50}$ value 32 µM. No previous biological activities have been reported with regard to this synthetic polyhydroxy analog. This compound did not affect the bacterial growth at least up to a concentration of 200 µM, showing that it is a selective biofilm inhibitor. While compound 11 exhibited comparable biofilm inhibition to compound 9 ($IC_{50}$ value of 34 μM, and 32 μM respectively) compound 11 also inhibited *S. mutans* growth at this concentration.

Figure 12A:
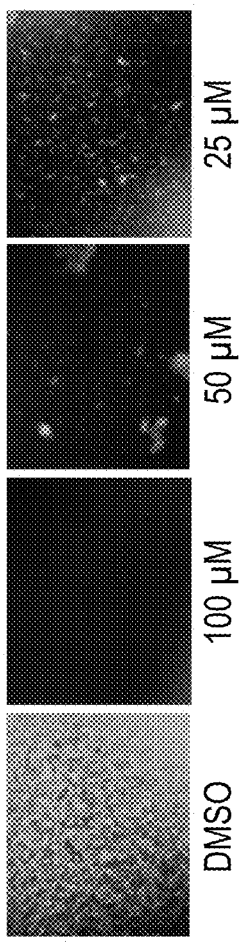
FIG. 12A shows microscopic evaluation of *S. mutans* biofilms inhibited by compound 9. *S. mutans* UA159 wild type was co-incubated with compound 9 at various concentrations and its subsequent biofilms were stained with Syto9.
Figure 12B:
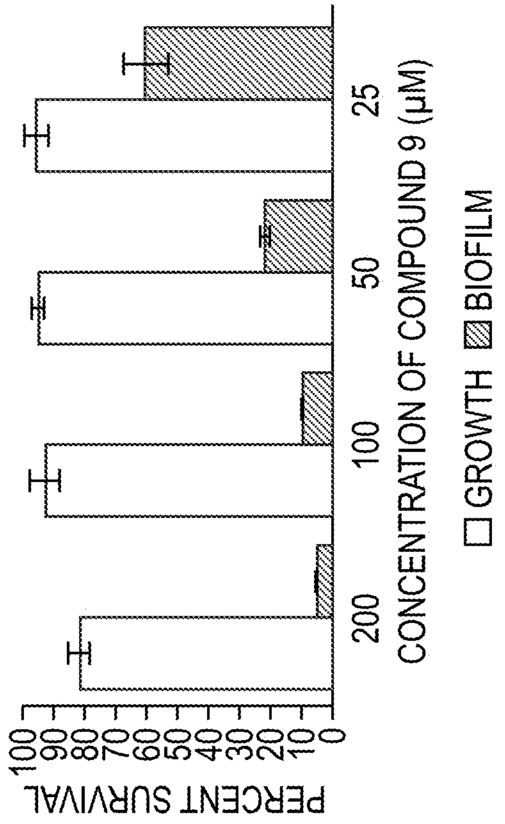
FIG. 12B shows *S. mutans* growth and biofilm affected by compound 9. *S. mutans* UA159 was co-incubated with compound 9 at various concentrations and their growth was measured at $OD_{470}$. Using the crystal violet protocol, their biofilm was measured at $OD_{562}$.
Figure 12C:
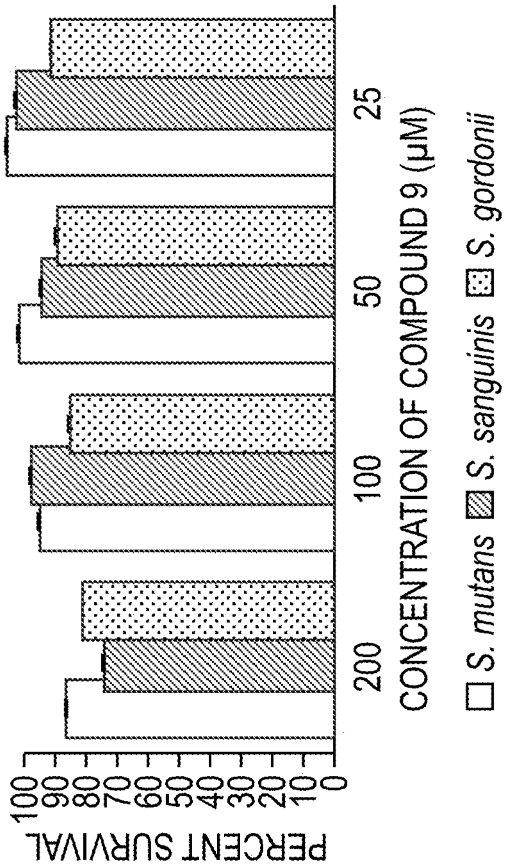
FIG. 12C shows the effect of compound 9 on commensal streptococci. *S. mutans* UA159, *S. sanguinis, S. gordonii* were co-incubated with compound 9 at various concentrations and their growth was measured at $OD_{470}$.

Thus, compound 9 was selected as the lead scaffold for the further development of the selective antibiofilm agents. In order to further establish its potency, the biofilms produced by *S. mutans* treated with this compound at various concentrations were imaged as shown in FIG. 12A. FIG. 12B depicts the dose-dependent inhibition of *S. mutans* growth and biofilm at various concentrations. Considerable selectivity can be seen, especially at higher concentrations. Finally, the effect of it on the survival rates of *S. mutans*, and two commensal species (*S. sanguinis, S. gordonii*) were used to assess the toxicity of this scaffold. At higher concentrations (200 μM), approximately 10-18% inhibition is seen with all strains when compared to DMSO (FIG. 12C). It is important to note that at the biofilm $IC_{50}$ value of 32 μM, no significant bactericidal activity is observed. Thus, compound 9 was concluded to be a non-toxic and a biofilm-selective inhibitor.

As compound 9 was obtained from the NCI library in a very a small quantity, it was not possible to ascertain its structure with NMR spectroscopic analysis. In addition, the stereochemistry of the double bond (E or Z) present in this molecule was not reported in the NCI database. Thus, both E and Z isomers of the compound 9 were synthesized and characterized. The preparation of the E isomer of 9 (9a) was achieved by the Claisen-Schmidt aldol condensation of the desired benzaldehyde (15a) and acetophenone (16a) in EtOH using aqueous NaOH as the base in 93% yield. Demethylation of the intermediate methoxy substituted compound 17a was accomplished by the treatment with $BBr_3$ in $CH_2Cl_2$ under $N_2$ atmosphere led to the formation of compound 9a (E isomer) in 87% yield (Scheme 1).

Scheme 1: Synthesis of the E chalcones

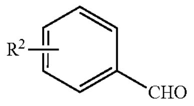

+

15a, $R^2$ = 2′,4′,5′ tri-$OCH_3$
15b, $R^2$ = 2′,4′,5′ tri-$OCH_3$
15c, $R^2$ = 2′,4′,5′ di-$OCH_3$

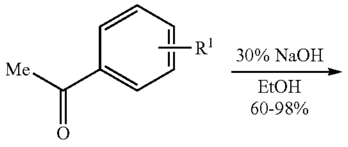

16a, $R^1$ = 3-$OCH_3$
16b, $R^1$ = 4-$OCH_3$
16c, $R^1$ = 2-$OCH_3$

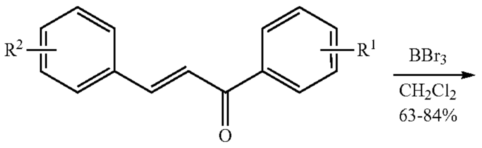

17a, $R^2$ = 2′,4′, di-$OCH_3$, $R^1$ = 3-$OCH_3$
17b, $R^2$ = 2′,4′, di-$OCH_3$, $R^1$ = 4-$OCH_3$
17c, $R^2$ = 2′,4′, 5′ tri-$OCH_3$, $R^1$ = 2-$OCH_3$
17d, $R^2$ = 2′,4′, 5′ tri-$OCH_3$, $R^1$ = 4-$OCH_3$ -continued

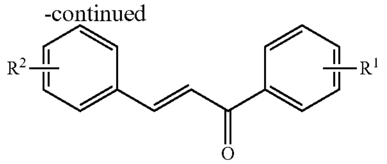

9a, $R^2$ = 2′,4′, di-OH, $R^1$ = 3-OH
18b, $R^2$ = 2′,4′, di-OH, $R^1$ = 4-OH
18c, $R^2$ = 2′,4′, 5′ tri-OH, $R^1$ = 2-OH
18d, $R^2$ = 2′,4′, 5′ tri-OH, $R^1$ = 4-OH The stereospecific synthesis of the Z isomer of compound 9b was performed using a reported procedure of acid mediated aldol condensation as shown in Scheme 2. $BF_3.Et_2O$ mediated condensation of 2,4-dihydroxybenzaldehyde (19) with m-hydroxyl acetophenone (20a) resulted in the Z-isomer 9b in contrast with the results obtained when using NaOH. This method was tolerant of pre-existing hydroxyl groups and thus required no protecting groups.

Scheme 2: Synthesis of the Z chalcones

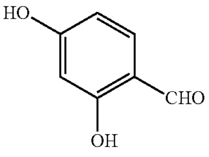

+

19

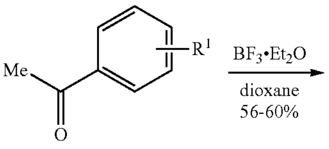

20a, $R^1$ = 3-OH
20b, $R^1$ = 4-OH

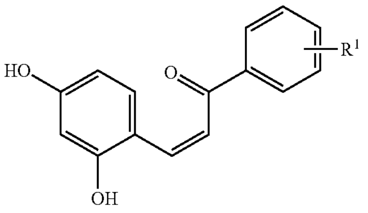

9b, $R^1$ = 3-OH
21b, $R^1$ = 4-OH

Taking compound 9 as the lead, a small collection of both E and Z isomers of a few hydroxychalcone derivatives (18b-d and 21b) with different substitutions in rings A, B were prepared using the synthetic procedures described above. Selected examples and their activities are shown in Table 7.

TABLE 7

Biofilm and growth inhibition profiles of synthesized analogs of compound 9

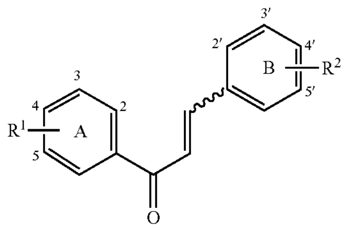

| No | E/Z | $R^1$ | $R^2$ | Biofilm $IC_{50}$ (μM)[a] | Growth $IC_{50}$ (μM)[a] | SI[b] |
|---|---|---|---|---|---|---|
| 9a | E | 3-OH | 2',4' di-OH | 68 ± 3 | 639 ± 25 | 9.39 |
| 9b | Z | 3-OH | 2',4' di-OH | 44 ± 5 | 468 ± 16 | 10.6 |
| 18b | E | 4-OH | 2',4' di-OH | 162 ± 21 | 1063 ± 118 | 6.6 |
| 21b | Z | 4-OH | 2',4' di-OH | 77 ± 8 | 782 ± 96 | 10.1 |
| 18c | E | 2-OH | 2',4',5' tri-OH | 224 ± 23 | 323 ± 36 | 1.5 |
| 18d | E/Z | 4-OH | 2',4',5' tri-OH | 76. ± 6 | 376 ± 6 | 4.9 |

[a]Average of at least 5 measurements.

[b]Selectivity index calculated by dividing growth $IC_{50}$ value by biofilm $IC_{50}$ value.

E and Z isomers of the lead compound, E and Z isomers of a synthetic derivative and two other compounds that further explore the hydroxyl regiochemistry of chalcones were included. Due to the possibility of photo-isomerization of chalcones, which has been previously demonstrated to be correlated with the substituents in the aromatic rings and pH dependent (Balsera, B., Mulet, J., Fernandez-Carvajal, A., de la Torre-Martinez, R., Ferrer-Montiel, A., Hernandez-Jimenez, J. G., Estevez-Herrera, J., Borges, R., Freitas, A. E., Lopez, M. G., Garcia-Lopez, M. T., Gonzalez-Muniz, R., Perez de Vega, M. J., Valor, L. M., Svobodova, L., Sala, S., Sala, F., Criado, M., European journal of medicinal chemistry, 2014, 86, 724), all samples were tested immediately upon making them. The biofilm and growth inhibition profiles were screened using the assay protocols as described earlier. All compounds asides from compound 18c demonstrated considerable selectivity in biofilm inhibition. Compound 18c was the most toxic to planktonic cells with a selectivity index of 1.5; a result that is consistent to the observation reported earlier. Comparing the activities of the E and Z pairs (9a and 9b and 18b and 21b), the Z isomers demonstrate slightly better inhibitions of both biofilm and growth. The most active compound (9) that emerged from the NCI screen had a biofilm $IC_{50}$ value of 32 μM, while the synthesized cis isomer of this compound (9b) exhibited a slight decrease in activity with an $IC_{50}$ value of 44 μM. Corresponding E isomer (9a) also had a slightly decreased activity with an $IC_{50}$ value of 68 μM. Both 9a and 9b demonstrated a selectivity index of about 10 towards biofilm inhibition. The Z isomer (21b) fared slightly better at being selective compared to its E isomer when comparing compounds with a hydroxyl in the $4^{th}$ position of ring A also. Compound 18d (mixture of E/Z) produced biofilm activity with moderate selectivity. Thus, the demonstrated selectivity of these compounds makes them amenable for the development of non-toxic biofilm inhibitors.

Figure 13A:
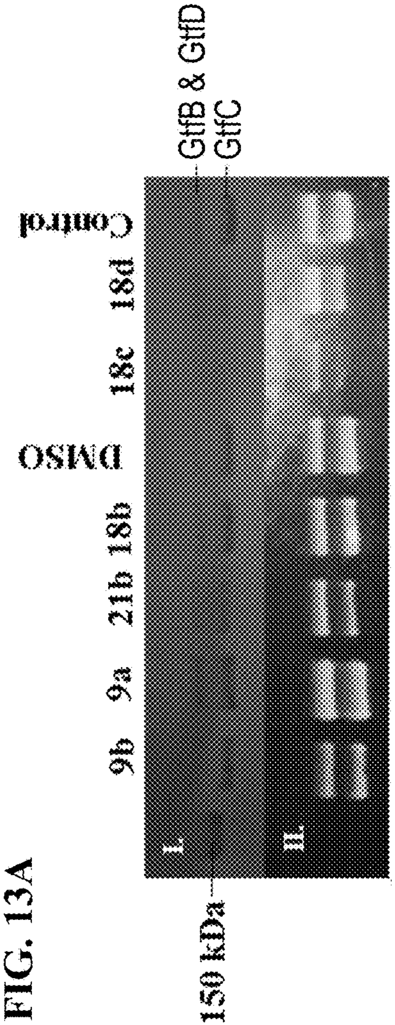
FIG. 13A shows Gtf level and activity determined by SDS-PAGE analysis and zymographic assay. *S. mutans* UA159 wild type were co-incubated with compounds of interest at 50 μM. Gtfs were concentrated from *S. mutans* UA159 wild type and then ran through duplicate SDS-PAGE. The upper panel (I.) is Coomassie blue staining of proteins analyzed by SDS-PAGE. The bottom panel (II.) shows glucan bands produced in the zymographic assay. The intensity of the bands reflects Gtf enzyme activity.

In order to establish the relationship between the biofilm inhibition and the effect on Gtfs, a zymogram assay was performed on six of the active compounds and the inhibition of Gtfs was qualitatively observed on an SDS-page gel through the intensity of the glucan bands produced. Data from selected compounds is presented in FIG. 13A. Each of these compounds was added to overnight cultures at 50 μM concentrations, and the Gtfs were collected from supernatants. One of the duplicate SDS-PAGE gel is Coomassie blue stained while the other is subjected to the zymogram assay, where the glucan bands produced represent Gtfs enzyme activities. GtfB and GtfD remain unresolved above the 150 kD reference ladder while a clear separation can be seen with the single band of GtfC.

Figure 13B:
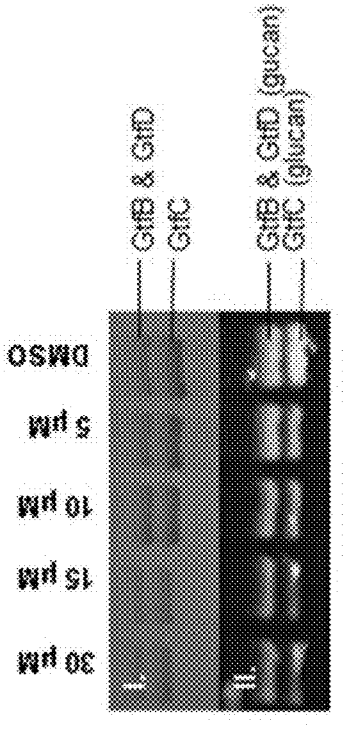
FIG. 13B shows effects of compound 9b at different concentrations. *S. mutans* UA159 wild type bacteria were co-incubated with compound 9b various concentrations. Protein profiling (I) and activity (II) of Gtfs were evaluated as described in FIG. 13A.

With regard to effects on protein level, compounds 9b, 18b, 18c and 21b showed an inhibitory effect on the production of Gtfs. Compound 18c shows the largest inhibition and this result is logical given the bactericidal effects of the compound. Mechanism by which these compounds affect the Gtf expression is unknown and warrants further investigation. With regard to Gtf enzyme inhibitory activity, several of the polyhydroxy chalcones exhibited a prominent effect. Comparing the activities of the E and Z pairs (9a, 9b and 18b, 21b), the Z isomers (9b and 21b) exhibit the best inhibitory effects, consistent with the biofilm inhibition. A decrease is observed in the bottom GtfC band, but a decrease in the upper band GtfBD is also observed, suggesting that the compound inhibited Gtfs. This is expected as GtfC and GtfB share 76% homology. Surprisingly, the E isomers 9a and 18b did not exhibit a drastic effect, suggesting that perhaps these isomers use a different pathway to illicit biofilm inhibition. Compound 18d demonstrates some weak inhibition of the GtfC band. A dose-dependent zymogram experiment of compound 9b was performed to determine if any selectivity would emerge (FIG. 13B). All Gtfs were inhibited by compound 9b dose-dependently. Thus, we conclude this compound affects the production and activity of all Gtfs.

Figure 13C:
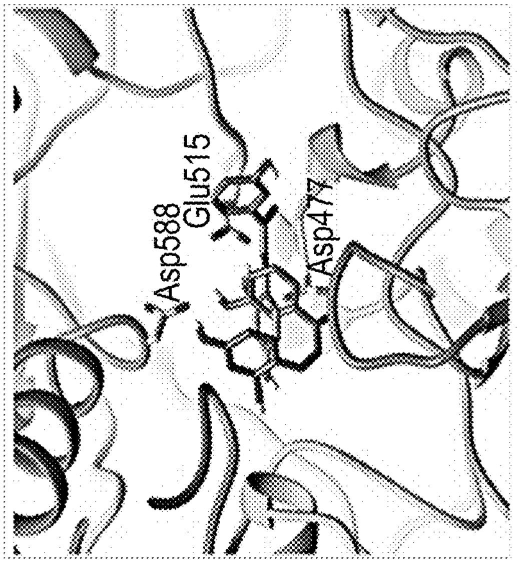
FIG. 13C shows Docking poses of compounds 9a in blue and 9b in green and the key residues interactions of GtfC active site.

Docking analysis of the two different isomers 9a and 9b within the GtfC active site revealed slightly different binding modes (FIG. 13C), which may explain the differences observed between the inhibitions seen in the zymograms and biofilm activity. A previous report indicated that binding of acarbose to Glu515 compromised the acid/base catalyst function, while interactions with Asp477 and Asp588 blocked the acceptor glycosyl moiety, explaining the inhibitory properties shown by acarbose when bound to GtfC (Ito, K., Ito, S., Shimamura, T., Weyand, S., Kawarasaki, Y., Misaka, T., Abe, K., Kobayashi, T., Cameron, A. D., Iwata, S., Journal of molecular biology, 2011, 408, 177). While the docking analysis showed that these three residues were within proximity to the both isomers, the Z isomer, 9b showed the hydroxy groups positioned appropriately and closer to the three key residues when compared to the E isomer, 9a.

Figure 13D:
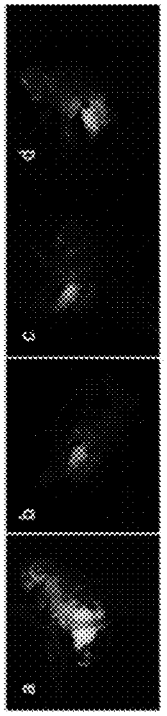

A sucrose-dependent *Drosophila* colonization model (Peng, X., Zhang, Y., Bai, G., Zhou, X., Wu, H., Molecular microbiology, 2015, 99, 945) was used to examine the effect of both compounds 9a and 9b on *S. mutans* colonization in vivo. Briefly, Gfp tagged *S. mutans* bacteria were infected into flies along with the treatment appropriate compound at 100 μM in a feeding-assay. DMSO was used as a negative control (FIG. 13D) and gtfB mutant, a known biofilm defective strain, was used as a positive control (FIG. 13D panel a). The fluorescence intensity was observed in guts of the flies fed with the Gfp tagged bacteria after 7 days of infection. A marked reduction in fluorescence was observed by both compounds 9a and 9b (FIG. 13D panels d and c), with 9b eliciting a more potent effect, producing an effect similar to that observed in the gtfB mutant (FIG. 13D panel b). This data is consistent with the zymogram and the biofilm inhibition observed previously.

Thus, this study demonstrated the *S. mutans* antibiofilm activities of polyhydroxychalcones, and observed some trends in activities with respect to the stereochemistry of the double bond and the regiochemistry and numbers of hydroxyl groups present in the molecules. Several low micromolar biofilm inhibitors emerged. Chalcones which contained a hydroxyl group in the third position of ring A exhibited higher selectivity for biofilm over growth. The lead compounds were further evaluated for their effect on *S. mutans* Gtfs and their effect on commensal bacteria and found that these scaffolds have an effect of Gtf expression and activity. The relationship between the biofilm activity and Gtf inhibition was established using a zymogram assay. These results were further validated by conducting a docking analysis of Z and E isomers of one of the lead compounds. This study also demonstrated the effect of two lead compounds on *S. mutans* colonization in vivo.

Docking protocols: The crystal structure of the complex of GtfC and acarbose (resolution: 3.11 Å, PDB code: 3AIC) was used for the in silico screening. The GtfC active site was prepared by selecting residues and cofactors (water and MES) within 6.5 Å of acarbose and then a pharmacophore that consists of Asp588 (H-acceptor) and Gln960 (H-donor) was generated. The reliability of the FlexX/LeadIT package was assessed by virtually generating a 3D structure of acarbose using VEGA-Z, and then by docking the structure into the prepared GtfC active site. This resulting docking generated a comparable binding mode to the experimental data. A library of about 1,000 small molecules obtained in 3D mol2 format from the free-access ZINC database specific to NCI compounds bearing at least one phenol group was used for the in silico screening. Docking runs were performed with a maximum allowed number of 2000 poses for each compound. The produced binding energies were ranked according to the highest scoring conformation. Compounds with binding energies better than −20 kJ/mol were selected for further investigation. The structures of top scoring compounds were examined for their bindings inside GtfC pocket, drug like properties based on Lipinski's rules, and for synthetic feasibility.

Bacterial strains, culture conditions, and chemicals. Bacterial strains, including *S. mutans* UA159 and various Gtf mutants, *S. sanguinis* SK36, and *S. gordonii* were grown statically at 37° C. with 5% $CO_2$ in Todd-Hewitt (TH) broth or THB agar plate, or in chemically defined biofilm medium supplemented with 1% sucrose. Chalcone small molecule candidates were obtained from NCI or synthesized in dimethyl sulfoxide at 20 mM and arrayed in a 96-well format for biological screening.

*S. mutans* biofilm formation and inhibition assays. Biofilm assays using 96-well flat-bottom polystyrene microtiter plates were performed to evaluate *S. mutans* biofilm formation at various conditions as described. Each assay was replicated five times. Compounds that inhibited 50% biofilm formation were determined by serial dilutions. The most active compounds isolated from the library were selected for further examination.

Inhibition of the activity of Gtfs determined by zymographic assays. A well-established zymographic assay was used to determine enzymatic activity of Gtfs (Mattos-Graner, R. O., Napimoga, M. H., Fukushima, K., Duncan, M. J., Smith, D. J., J Clin Microbiol, 2004, 42, 4586). In brief, overnight *S. mutans* UA159 cultures were diluted 1:100 in fresh 5 mL THB with 50 μL of selective compounds at a series of concentrations. Treated bacteria were grown to OD470 of 1.0, and spun down by centrifugation at 4° C., and culture supernatants were collected and filtered through a 0.22-μm-pore-size filter membrane to remove residual bacterial cells and dialyzed at 4° C. against 0.02 M sodium phosphate buffer (pH 6.8), with 10 μM phenylmethylsulfonyl fluoride (PMSF), followed by a second dialysis against 0.2 mM sodium phosphate containing 10 μM PMSF. After dialysis, 4 mL of samples were concentrated to 40 μL by 100K Amicon Ultra-4 centrifugal filter (Merk Millipore Ltd.). For electrophoresis and zymographic analysis, 10 μL of each concentrated culture supernatant was applied to 8% SDS-PAGE in duplicate. One gel was used for protein staining with Coomassie blue dye, while the other one was subjected to zymographic assay. The resultant white opaque glucan bands were visualized against a black background.

Cell viability of *S. mutans* and commensal *S. gordonii* and *S. sanguinis*. Effects of lead small molecules on cell viability were examined. The number of colony-forming units (CFU) per milliliter for each compound at different concentrations was determined after incubation for 24 h at 37° C. and compared to the values obtained from the DMSO control group.

Colonization of *Drosophila*. Infections of flies were performed as described (Chugani, S. A., Whiteley, M., Lee, K. M., D'Argenio, D., Manoil, C., Greenberg, E. P., Proceedings of the National Academy of Sciences of the United States of America, 2001, 98, 2752; Peng, X., Zhang, Y., Bai, G., Zhou, X., Wu, H., Molecular microbiology, 2015, 99, 945; Mulcahy, H., Sibley, C. D., Surette, M. G., Lewenza, S., PLoS pathogens, 2011, 7). Mid-log phase THB cultures of Gfp-tagged (green fluorescent protein) *S. mutans* UA159 were spun down and resuspended in a solution containing 5% sucrose and 50 μM of the compound. 100 μL of resuspended cells were spotted onto a sterile filter that was placed on the surface of 5 mL of solidified 5% sucrose agar in a plastic vial. The vials were allowed to dry at room temperature for 30 minutes prior to addition of flies. Male Canton S flies (1-3 days old) were treated with antibiotics for 2 days and starved for 3 hours prior to the addition to vials supplied with *S. mutans* (10 flies per vial). The colonization of flies by Gfp-tagged strains were analyzed by Nikon elipse 90i microscope, equipped with an Epi-fluorescence and NIS elements AR imaging system.

Synthesis of chalcones using NaOH: General Procedure. A mixture of the acetophenone (1 mmol) and the aldehyde (1 mmol) was dissolved in EtOH (10 mL). An aqueous solution of NaOH (40%, 1 mL) was added to this solution at 0-5° C. The reaction mixture was allowed to attain room temperature and then stirring was continued for 12 h. TLC examination (30% ethyl acetate in hexane) indicated the completion of the reaction. The reaction mixture was then poured over crushed ice and acidified to pH ~2 with 1N. HCl. The light yellow solid precipitated was filtered, washed with water, and dried. The product obtained was either purified on column chromatography (Si gel with 10% ethyl acetate in hexane) or recrystallized from EtOH.

Synthesis of chalcones using $BF_3.OEt_2$: General Procedure. To a solution of the dihydroxybenzaldehyde (1 mmol) and the corresponding hydroxyacetophenone (0.5 mmol) in 1,4-dioxane (10 mL), $BF_3.Et_2O$ (3 nmol) was added. The reaction mixture was stirred at room temperature for 24 h. Upon completion of the reaction as indicated by TLC (30% ethyl acetate in hexane), the precipitated solid was filtered and washed with $CH_2Cl_2$ to afford the Z-isomer of polyhydroxylchalcones.

Demethylation using $BBr_3$: General Procedure. The corresponding methoxy substituted chalcones (0.25 mmol) obtained from the previous step (1) were dissolved in dried $CH_2Cl_2$ (15 mL) and cooled down to 0° C. $BBr_3$ (2 equiv per any potentially basic N or O) was slowly added to the reaction mixture kept under $N_2$ atmosphere. After stirring for 24 h at room temperature, the reaction was cooled to 0° C. and quenched with a very slow addition of $H_2O$. The resulting red solids were separated by filtration and washed with $H_2O$ and $CH_2Cl_2$. The crude product was further purified by column chromatography over Si gel using 20% MeOH in $CH_2Cl_2$ to afford the hydroxyl chalcones.

Spectral data of the compounds of this study are noted below.

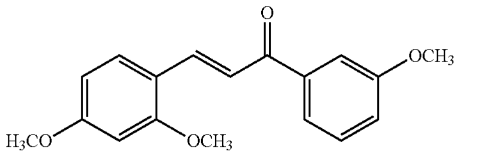 [SMILES: COc1cccc(C(=O)/C=C/c2ccc(OC)cc2OC)c1]

(E)-3-(2,4-Dimethoxyphenyl)-1-(3-methoxyphenyl)-2-propen-1-one (17a) yellow oil, (259 mg, 87%), purified by column. M.P=75-78° C. $^1$H-NMR (300 MHz, $CDCl_3$) δ: 3.83-3.91 (m, 9H), 5.57 (d, J=2.4 Hz, 1H), 5.63 (dd, J=8.4 Hz, $J_2$=2.4 Hz, 1H), 6.15-6.25 (m, 1H), 6.42-6.53 (m, 1H), 6.60-6.72 (m, 4H), 7.18 (d, J=15.6 Hz, 1H). $^{13}$C NMR (75 MHz, $CDCl_3$) δ: 55.4 (2C), 55.5, 98.3, 105.3, 112.7, 117.0, 118.7, 120.3, 120.9, 129.3, 130.9, 140.2, 140.5, 159.7, 160.3, 163.0, 190.8. EI-MS m/z: 298.8 [M]$^+$; HRMS calculated for $C_{18}H_{18}O_4$ [M+H]$^+$ 298.1211, found 298.1205.

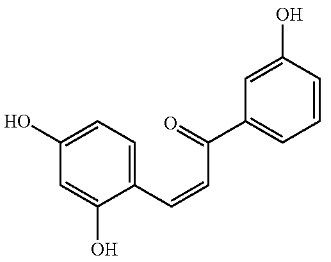 [SMILES: O=C(/C=C\c1ccc(O)cc1O)c1cccc(O)c1]

(Z)-3-(2,4-Dihydroxyphenyl)-1-(3-hydroxyphenyl)-2-propen-1-one (9b) Amorphous red solid, (71.2 mg, 56%), purified by column. M.P=164-167° C., $^1$H NMR (DMSO, 700 MHz) δ: 7.27 (d, J=6.0 Hz, 1H), 7.49-7.59 (m, 3H), 7.84 (d, J=3.0 Hz, 1H), 7.98 (d, J=9.0 Hz, 1H), 8.30 (d, J=6.0 Hz, 1H), 8.60 (d, 1H, J=6.0 Hz, 1H), 9.41 (d, J=9.0 Hz, 1H), 10.28 (brs, 1H), $^{13}$C NMR (MeOD, 175 MHz) δ: 103.8, 11511.3, 121.9, 121.9, 123.9, 124.6, 131.9, 132.6, 134.7, 156.5, 160.4, 161.7, 172.1, 173.6. EI-MS m/z: 239.0 [M−$H_2O$]$^+$; HRMS calculated for $C_{15}H_{10}O_3$ [M−$H_2O$]$^+$ 238.0634, found 238.0630.

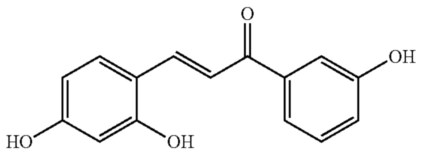 [SMILES: O=C(/C=C/c1ccc(O)cc1O)c1cccc(O)c1]

(E)-3-(2,4-Dihydroxyphenyl)-1-(3-hydroxyphenyl)-2-propen-1-one (9a). Red solid (53 mg, 84%), purified by column. M.P=73-75° C. $^1$H NMR (MeOD, 700 MHz) δ: 6.82 (dd, $J_1$=11.9 Hz, $J_2$=8.2 Hz, 1H), 6.90 (dd, $J'_2$ 11.7 Hz, $J_2$=8.8 Hz, 2H), 7.10 (d, $J_1$=9.4 Hz, 1H), 7.18 (d, $J_1$=11.2 Hz, 1H), 7.43-7.67 (m, 1H), 7.61-7.67 (m, 1H), 7.96-8.02 (m, 2H); $^{13}$C NMR (MeOD, 175 MHz) δ:101.0, 106.6, 115.7, 116.6, 119.6, 123.4, 128.5, 131.2, 132.2, 134.1, 146.2, 146.8, 149.8, 163.7, 191.1. EI-MS m/z: 257.1 [M]$^+$; HRMS calculated for $C_{15}H_{12}O_4$ [M+H]$^+$ 256.0730, found 256.0736.

21 b

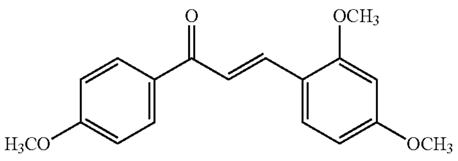

(E)-3-(2,4-dimethoxyphenyl)-1-(4-methoxyphenyl)prop-2-en-1-one (17b). Crystallized from MeOH as yellow crystals. (292 mg, 98%) M.P=80-82° C., $^1$H NMR (300 MHz, $CDCl_3$) δ: 3.78-3.90 (m, 9H), 6.47 (d, J=6.0 Hz, 1H), 6.53 (dd, $J_1$=8.4, $J_2$=2.1 Hz, 1H), 6.88-7.00 (m, 2H), 7.54 (d, J=6.9 Hz, 1H), 7.58 (s, 1H), 8.05-8.11 (m, 3H). $^{13}$C NMR ($CDCl_3$, 75 M Hz) δ: 55.6 (×2), 55.7, 98.6, 105.5, 113.8, 117.4, 120.4, 130.8, 130.9, 131.8, 139.8, 160.4, 163.0, 163.2, 189.5. EI-MS m/z: 299.0 [M]$^+$; HRMS calculated for $C_8H_{18}O_4$ [M+H]$^+$ 298.1202, found 298.1205.

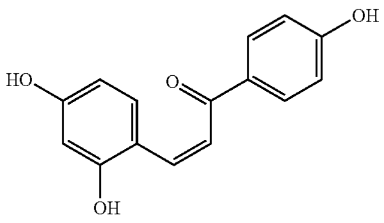 [SMILES: O=C(/C=C\c1ccc(O)cc1O)c1ccc(O)cc1]

(Z)-3-(2,4-Dihydroxyphenyl)-1-(4-hydroxyphenyl)-2-propen-1-one (21b). Brown solid (76.8 mg, 60%), M.P=185-187° C. $^1$H NMR (MeOD, 700 MHz) δ: 7.05 (dd, $J_1$=14.0 Hz, $J_2$=8.8 Hz, 2H), 7.35 (dd, $J_1$=12.1 Hz, $J_2$=9.6 Hz, 1H), 7.43 (d, J=12.6 Hz, 1H), 8.09 (dd, $J_1$=14.0 Hz, $J_2$=8.8 Hz, 1H), 8.23 (dd, $J_1$=13.9 Hz, $J_2$=8.8 Hz, 1H), 8.35 (dd, $J_1$=13.8 Hz, $J_2$=8.8 Hz, 2H), 8.99 (dd, $J_1$=13.8 Hz, $J_2$=8.8 Hz, 1H); $^{13}$C NMR (MeOD, 175 MHz) δ:101.8, 111.4, 116.8, 118.1, 119.3, 120.4, 132.0, 132.1, 152.5, 158.3, 166.2, 168.3, 171.9; EI-MS m/z: 238.9 [M−$H_2O$]$^+$; HRMS calculated for $C_{15}H_{10}O_3$ [M−$H_2O$]$^+$238.0638, found 238.0630.

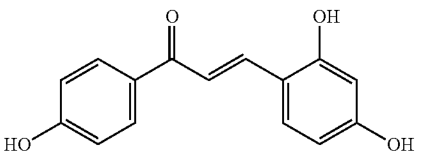 [SMILES: O=C(/C=C/c1ccc(O)cc1O)c1ccc(O)cc1]

(E)-3-(2,4-Dihydroxyphenyl)-1-(4-hydroxyphenyl)-2-propen-1-one (18b) Amorphous red solid (50 mg, 78%), purified by column. M.P=185-188° C. $^1$H NMR (MeOD, 700 MHz) δ: 7.11 (d, J=8.8 Hz, 2H), 7.41 (d, J=8.8 Hz, 1H), 7.52 (s, 1H), 8.15 (d, J=8.8 Hz, 1H), 8.32 (d, J=8.6 Hz, 1H), 8.42 (d, J=8.8 Hz, 2H), 9.07 (d, J=8.6 Hz, 2H). $^{13}$C NMR (MeOD, 175 MHz) δ: 101.9, 110.0, 111.7, 116.8, 116.9, 118.2, 119.4, 120.4, 120.5, 132.1, 132.3, 152.6, 152.7, 158.4, 166.2, 168.2, 171.2. EI-MS m/z: 238.9 $[M-H_2O]^+$; HRMS calculated for $C_{15}H_{10}O_3$ $[M-H_2O]^+$ 238.0637, found 238.0630.

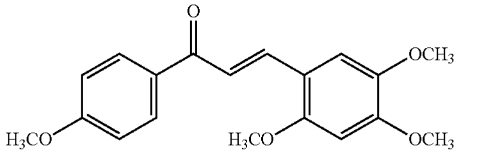 [SMILES: COc1ccc(C(=O)/C=C/c2cc(OC)c(OC)cc2OC)cc1]

(E)-1-(4-methoxyphenyl)-3-(2,4,5-methoxyphenyl)prop-2-en-1-one (17d) Crystallized from MeOH as yellow crystals (246.0 mg, 75%), $^1H$ NMR ($CDCl_3$, 300 MHz) δ: 3.83-3.97 (m, 12H), 6.52 (s, 1H), 6.96 (d, J=8.4 Hz, 2H), 7.13 (s, 1H), 7.48 (d, J=15.6 Hz, 1H), 8.00-8.8.12 (m, 3H). $^{13}C$ NMR ($CDCl_3$, 175 MHz) δ:56.6, 56.2, 56.6, 56.8, 97.1, 111.7, 113.9, 115.9, 120.4, 130.8, 131.8, 139.7, 143.5, 152.5, 154.7, 163.2, 189.5. EI-MS m/z: 328.8 $[M]^+$; HRMS calculated for $C_{19}H_{20}O_5$ $[M+H]^+$ 328.1312, found 328.1311.

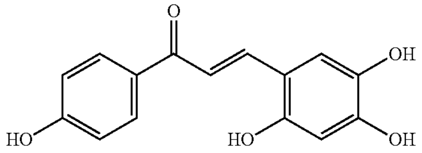 [SMILES: O=C(/C=C/c1cc(O)c(O)cc1O)c1ccc(O)cc1]

(E)-1-(4-hydroxyphenyl)-3-(2,4,5-trihydroxyphenyl) prop-2-en-1-one (18d) Amorphous red solid (42.8 mg, 63%), purified by column. H NMR (MeOD, 700 MHz) δ: 7.10 (d, J=8.1, 2H), 7.44 (s, 1H), 7.55 (s, 1H), 8.26 (d, J=7.5 Hz, 1H), 8.35 (d, J=8.3 Hz), 8.92 (d, J=6.8, 1H). $^{13}C$ NMR (MeOD, 175 MHz) δ: 102.3, 109.9, 111.6, 120.1, 120.3, 149.5, 150.2, 154.5, 160.8, 165.3, 169.3. EI-MS m/z: 289.9 $[M]^+$; HRMS calculated for $C_{15}H_{10}O_4$ $[M-H_2O]^+$ 254.0578, found 254.0579.

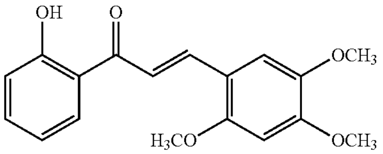 [SMILES: COc1cc(OC)c(OC)cc1/C=C/C(=O)c1ccccc1O]

(E)-1-(2-hydroxyphenyl)-3-(2,4,5-trimethoxyphenyl) prop-2-en-1-one (17c) Crystallized from MeOH as yellow crystals (188.9 mg, 59.1%). H NMR ($CDCl_3$, 400 MHz) δ: 3.95 (s, 9H), 6.50 (s, 1H), 6.96 (d, 2H, J=32.9 Hz), 7.10 (s, 1H) 7.39-7.54 (m, 1H), 7.59 (d, 1H, J=11.6 Hz) 7.84-8.00 (m, 1H) 8.20 (d, 1H, J=11.6 Hz) 13.10 (s, 1H); $^{13}C$ NMR ($CDCl_3$, 100 MHz) δ: 56.2, 56.4, 56.7, 96.8, 111.9, 115.3, 117.9, 118.6, 118.8, 120.4, 129.7, 136.0, 141.1, 143.4, 153.2, 155.3, 163.7, 194.2. HRMS calculated for $C_8H_{18}O_5$ $[M+H]^+$ 314.1162, found 314.1154.

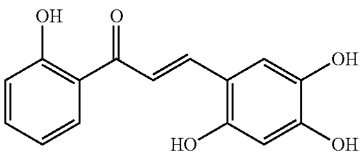 [SMILES: O=C(/C=C/c1cc(O)c(O)cc1O)c1ccccc1O]

(E/Z)-1-(2-hydroxyphenyl)-3-(2,4,5-trihydroxyphenyl) prop-2-en-1-one (18c) Amorphous brown solid, (33.3 mg, 49%) This compound quickly isomerizes to a mixture of cis and trans isomers when in solution, and thus could not be properly characterized through NMR. EI-MS m/z: 254.8 $[M-H_2O]^+$; HRMS calculated for $C_{15}H_{12}O_5$ $[M+H]^+$ 272.0677, found 272.0685.

Example 4: Inhibition of *Streptococcus* Mutants Biofilms by the Natural Stilbene Piceatannol Through the Inhibition of Glucosyltransferases Current approaches to eradicate dental biofilms include its mechanical removal and the use of nonspecific broad-spectrum antibiotics (Walsh, T.; Oliveira-Neto, J. M.; Moore, D., Chlorhexidine treatment for the prevention of dental caries in children and adolescents. *The Cochrane database of systematic reviews* 2015, (4), 8457). The removal of bacterial biofilms through brushing demands frequent repetition because the tooth surfaces are rapidly re-colonized. Similarly, antimicrobial agents in mouthwashes such as chlorhexidine and delmopinol lack selectivity, affecting both pathogenic species and commensal beneficial species, and give rise to undesired side effects such as vomiting, diarrhea, addiction, or teeth discoloration.

Figure 14:
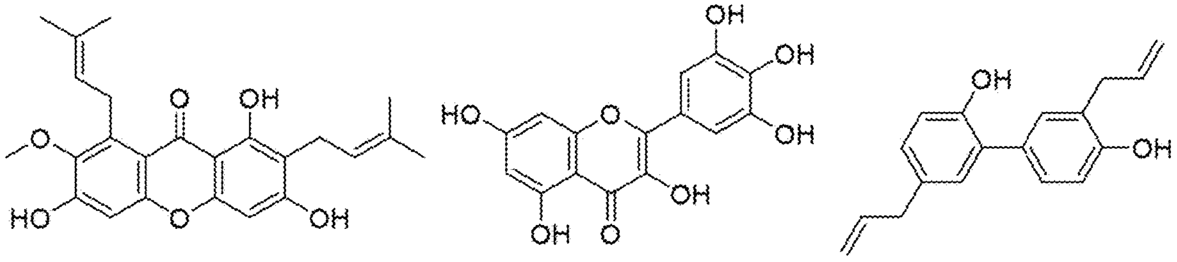
FIG. 14 shows chemical structures of some known natural product *S. mutans* biofilm and Gft inhibitors. Left) Alpha-Mangostin; Middle) Myricetin; Right) Honokiol.

Numerous natural products and their derivatives have been investigated for their potential to inhibit cariogenic plaque formation. These include constituents found in cranberry, plant lectins, crude extracts of *Morus alba* leaves, and components found in barley coffee (Koo, H.; Nino de Guzman, P.; Schobel, B. D.; Vacca Smith, A. V.; Bowen, W. H., Influence of cranberry juice on glucan-mediated processes involved in *Streptococcus mutans* biofilm development. *Caries research* 2006, 40 (1), 20-7; Thimothe, J.; Bonsi, I. A.; Padilla-Zakour, O. I.; Koo, H., Chemical characterization of red wine grape (*Vitis vinifera* and *Vitis* interspecific hybrids) and pomace phenolic extracts and their biological activity against *Streptococcus mutans*. *Journal of agricultural and food chemistry* 2007, 55 (25), 10200-7). Most of the reported studies suggests these agents to be effective against biofilm formation of *S. mutans* through varying degrees of the regulation of glucosyltransferases Too, H.; Nino de Guzman, P.; Schobel, B. D.; Vacca Smith, A. V.; Bowen, W. H., Influence of cranberry juice on glucan-mediated processes involved in *Streptococcus mutans* biofilm development. *Caries research* 2006, 40 (1), 20-7; Duarte, S.; Gregoire, S.; Singh, A. P.; Vorsa, N.; Schaich, K.; Bowen, W. H.; Koo, H., Inhibitory effects of cranberry polyphenols on formation and acidogenicity of *Streptococcus mutans* biofilms. *FEMS Microbiology Letters* 2006, 257 (1), 50-56). In addition, several small molecules, including anthraquinones (Pandit, S.; Song, K. Y.; Jeon, J. G., Withania somnifera attenuates acid production, acid tolerance and extracellular polysaccharide formation of *Streptococcus mutans* biofilms. *The American journal of Chinese medicine* 2014, 42 (1), 157-71), apigenin (Koo, H.; Rosalen, P. L.; Cury, J. A.; Park, Y. K.; Bowen, W. H., Effects of compounds found in propolis on *Streptococcus mutans* growth and on glucosyltransferase activity. *Antimicrobial agents and chemotherapy* 2002, 46 (5), 1302-9; Koo, H.; Hayacibara, M. F.; Schobel, B. D.; Cury, J. A.; Rosalen, P. L.; Park, Y. K.; Vacca-Smith, A. M.; Bowen, W. H., Inhibition of *Streptococcus mutans* biofilm accumulation and polysaccharide production by apigenin and tt-farnesol. *The Journal of antimicrobial chemotherapy* 2003, 52 (5), 782-9), tt-farnesol (Koo, H.; Pearson, S. K.; Scott-Anne, K.; Abranches, J.; Cury, J. A.; Rosalen, P. L.; Park, Y. K.;

Marquis, R. E.; Bowen, W. H., Effects of apigenin and tt-farnesol on glucosyltransferase activity, biofilm viability and caries development in rats. *Oral microbiology and immunology* 2002, 17 (6), 337-43; Koo, H.; Schobel, B.; Scott-Anne, K.; Watson, G.; Bowen, W. H.; Cury, J. A.; Rosalen, P. L.; Park, Y. K., Apigenin and tt-farnesol with fluoride effects on *S. mutans* biofilms and dental caries. *Journal of dental research* 2005, 84 (11), 1016-20), chitosan (Rajabnia, R.; Ghasempour, M.; Gharekhani, S.; Gholamhoseinnia, S.; Soroorhomayoon, S., Anti-*Streptococcus mutans* property of a chitosan: Containing resin sealant. *Journal of International Society of Preventive & Community Dentistry* 2016, 6 (1), 49-53), and 7-epiclusianone (Murata, R. M.; Branco-de-Almeida, L. S.; Franco, E. M.; Yatsuda, R.; dos Santos, M. H.; de Alencar, S. M.; Koo, H.; Rosalen, P. L., Inhibition of *Streptococcus mutans* biofilm accumulation and development of dental caries in vivo by 7-epiclusianone and fluoride. *Biofouling* 2010, 26 (7), 865-72; Branco-de-Almeida, L. S.; Murata, R. M.; Franco, E. M.; dos Santos, M. H.; de Alencar, S. M.; Koo, H.; Rosalen, P. L., Effects of 7-epiclusianone on *Streptococcus mutans* and caries development in rats. *Planta medica* 2011, 77 (1), 40-5), α-Mangostin (Nguyen, P. T.; Falsetta, M. L.; Hwang, G.; Gonzalez-Begne, M.; Koo, H., alpha-Mangostin disrupts the development of *Streptococcus mutans* biofilms and facilitates its mechanical removal. *PLoS One* 2014, 9 (10), 111312), myricetin (Falsetta, M. L.; Klein, M. I.; Lemos, J. A.; Silva, B. B.; Agidi, S.; Scott-Anne, K. K.; Koo, H., Novel antibiofilm chemotherapy targets exopolysaccharide synthesis and stress tolerance in *Streptococcus mutans* to modulate virulence expression in vivo. *Antimicrobial agents and chemotherapy* 2012, 56 (12), 6201-1; Kim, D.; Hwang, G.; Liu, Y.; Wang, Y.; Singh, A. P.; Vorsa, N.; Koo, H., Cranberry Flavonoids Modulate Cariogenic Properties of Mixed-Species Biofilm through Exopolysaccharides-Matrix Disruption. *PLoS One* 2015, 10 (12), e0145844), and honokiol (Greenberg, M.; Urnezis, P.; Tian, M., Compressed mints and chewing gum containing magnolia bark extract are effective against bacteria responsible for oral malodor. *Journal of agricultural and food chemistry* 2007, 55 (23), 9465-9) have been characterized and shown to have antibiofilm activity toward *S. mutans*. However, the majority of these compounds do not exhibit high selectivity against *S. mutans* biofilms. Chemical structures of a few of these natural products are given in FIG. 14.

Prior studies have indicated that resveratrol inhibits glycolytic acid production and Gtf activity of *S. mutans*, when tested using an ethyl acetate fraction from *Pediomelum cuspidatum* root, which is composed of polydatin, resveratrol, anthraglycoside B, and emodin (Kwon, Y. R.; Son, K. J.; Pandit, S.; Kim, J. E.; Chang, K. W.; Jeon, J. G., Bioactivity-guided separation of anti-acidogenic substances against *Streptococcus mutans* UA 159 from *Polygonum cuspidatum. Oral diseases* 2010, 16 (2), 204-9; Pandit, S.; Kim, H. J.; Park, S. H.; Jeon, J. G., Enhancement of fluoride activity against *Streptococcus mutans* biofilms by a substance separated from *Polygonum cuspidatum. Biofouling* 2012, 28 (3), 279-87; Yim, N.; Ha do, T.; Trung, T. N.; Kim, J. P.; Lee, S.; Na, M.; Jung, H.; Kim, H. S.; Kim, Y. H.; Bae, K., The antimicrobial activity of compounds from the leaf and stem of *Vitis amurensis* against two oral pathogens. *Bioorganic & medicinal chemistry letters* 2010, 20 (3), 1165-8). There are no reports related to stilbene's possible effect on the virulence of dental biofilms.

Ideal therapeutics for dental caries should be able to selectively inhibit pathogenic biofilms caused by *Streptococcus mutans*. The lead stilbene identified through our docking study against the catalytic domain of GtfC is a natural product known as piceatannol, which inhibited *S. mutans* biofilm formation in a dose-dependent manner with considerable selectivity over growth inhibition of *S. mutans* and commensal Streptococci. Binding kinetic analysis of piceatannol was performed using OctetRed against both GtfB and GtfC, which produced low micromolar $K_D$ values. Piceatannol inhibited *S. mutans* colonization in an in-vivo *drosophila* model and a rat model of dental caries.

Structure-based virtual screening of natural polyphenols. The 3D crystal structure of GtfC in complex with acarbose has been successfully employed to develop Gtf selective inhibitors (Ito, K.; Ito, S.; Shimamura, T.; Weyand, S.; Kawarasaki, Y.; Misaka, T.; Abe, K.; Kobayashi, T.; Cameron, A. D.; Iwata, S., Crystal Structure of Glucansucrase from the Dental Caries Pathogen *Streptococcus mutans. Journal of Molecular Biology* 2011, 408 (2), 177-186). We thus performed in-silico docking using FlexX/LeadIT software package, on a database of compounds containing at least one phenolic group against the high resolution X-ray crystal structure of GtfC (PDB code: 3AIC). Top scoring compounds were examined for their binding interactions with key residues such as Glu515, Ala478, Tyr430, Asp959, Leu333, Gln960, Asp477, and Asp588, drug like properties based on Lipinski's rules, and synthetic feasibility.

Inhibition of *S. mutans* biofilms by natural and synthetic stilbenes. The stilbenes obtained from the National Cancer Institute were first evaluated for their biofilm inhibitory and growth inhibitory activities using previously reported assays (Wen, Z. T.; Burne, R. A., Functional genomics approach to identifying genes required for biofilm development by *Streptococcus mutans. Applied and Environmental Microbiology* 2002, 68 (3), 1196-203). A range of activities were observed, with several compounds being inactive (compounds 1-3 and 13) and a few demonstrating inhibition of both *S. mutans* growth and biofilm at the micromolar range. Our studies have demonstrated that the stilbene scaffold alone does not possess a biological effect against *S. mutans*, as both the E and Z isomers were inactive (compounds 1 and 2). A significant effect is seen with the variation of substituents. Compounds 3 and 4 maintain the regiochemistry of the substituents but differ in their functional groups. While the dihydroxyl stilbene 4 has demonstrated biofilm and growth with $IC_{50}$ values of 344 μM and 854 μM, the diamino analog 3 did not produce any activity in either growth or biofilm. Similarly, compound 5 is a diamidine compound that also has an extra hydroxyl group has demonstrated biofilm and growth with $IC_{50}$ values of 104 μM and 179 μM.

Compounds 6-9 explore the regiochemistry and substituent effect of hydroxylstilbenes. Compound 6 is the least active compound of this class, showing a high micromolar range activity. This compound also does not have any substituents on one of the rings. Compounds 7 and 8 are natural products, resveratrol and piceatannol, respectively. These compounds differ by the inclusion of one extra hydroxyl group. Previous studies have shown resveratrol to inhibit *S. mutans* biofilm (Kwon, Y. R.; Son, K. J.; Pandit, S.; Kim, J. E.; Chang, K. W.; Jeon, J. G., Bioactivity-guided separation of anti-acidogenic substances against *Streptococcus mutans* UA 159 from *Polygonum cuspidatum. Oral diseases* 2010, 16 (2), 204-9; Pandit, S.; Kim, H. J.; Park, S. H.; Jeon, J. G., Enhancement of fluoride activity against *Streptococcus mutans* biofilms by a substance separated from *Polygonum cuspidatum. Biofouling* 2012, 28 (3), 279-87; Ban, S. H.; Kwon, Y. R.; Pandit, S.; Lee, Y. S.; Yi, H. K.; Jeon, J. G., Effects of a bio-assay guided fraction from *Polygonum cuspidatum* root on the viability, acid production and glucosyltranferase of *mutans* streptococci. *Fitoterapia* 2010, 81 (1), 30-4). In comparison to that, compound 8 shows a marginally better activity towards *S. mutans* biofilm with a 52 μM $IC_{50}$ value and also demonstrates increased (11 fold) selectivity. Compound 9 is a trimethoxy, monohydroxy analog of piceatannol that maintains its regiochemistry. This scaffold demonstrated less biofilm inhibition, increased growth inhibition compared to piceatannol (8), decreasing selectivity, which suggests that the OH groups are important for the selectivity.

Since the glucan synthesis pathway involves the degradation of glycosidic bond in sucrose and the formation of new glucosidic bonds between glucosyl units, we were interested in exploring the effect of attaching a glucose unit to one of the active compounds. Compound 12 is a glucoside analog of piceatannol 8, with the methylation of one of its hydroxyl groups. This compound also shows similar activity when compared to that of compound 9. However, compound 13 is a piceatannol analog that has a glucose substituent that is not attached through a glucosidic bond, and this compound is not active against biofilm and growth. Finally, compounds 10-11 are miscellaneous scaffolds that resemble a stilbene. Of these compounds, compound 11 demonstrated considerable activity against *S. mutans* biofilm. Overall, piceatannol (8) is the compound identified from this study that demonstrated good activity and selectivity towards *S. mutans* biofilm inhibition.

Figure 15A:
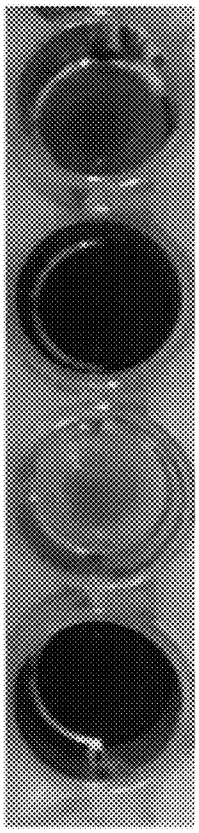
FIG. 15A shows a comparison of piceatannol and structural analogs at 200 μM in the crystal violet biofilm assay.
Figure 15B:
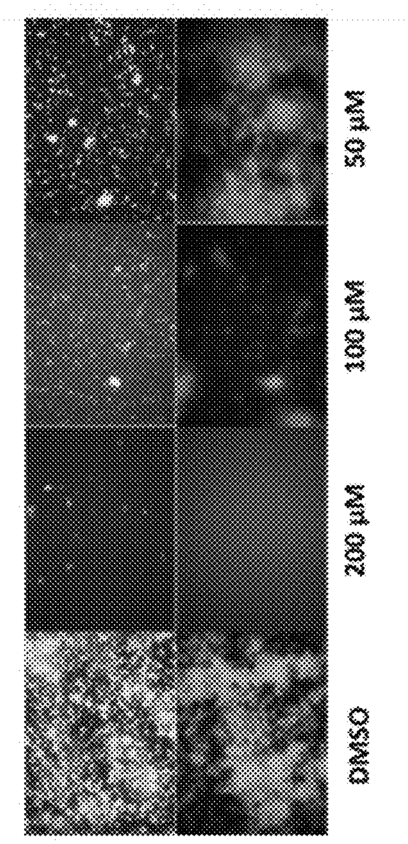
FIG. 15B shows fluorescence microscopy images of the *S. mutan's* biofilms treated with 8 200-50 μM. Top images correspond to bacteria stained with Syto9 while bottom images correspond to the fluorescent glucans within the biofilm tracked by the Cascade Blue labeled Dextran.
Figure 15C:
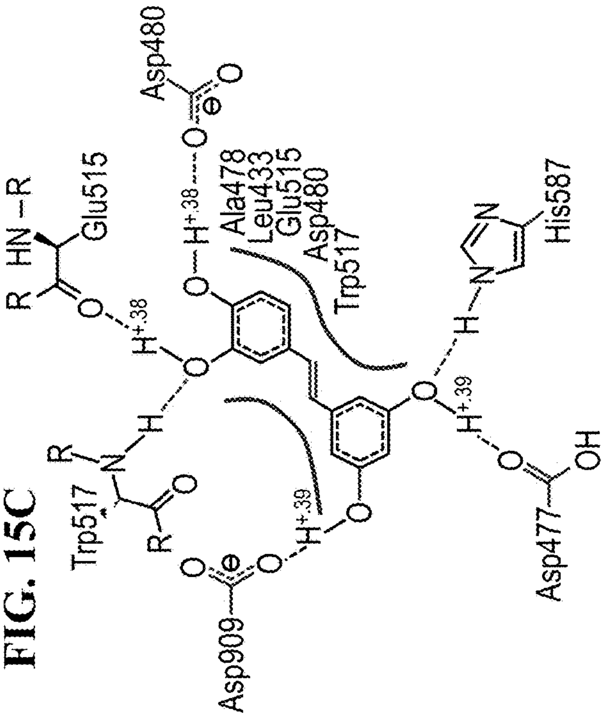
FIG. 15C shows 2D diagram of the proposed residues interacting with piceatannol.

Lead compound, piceatannol, inhibited biofilms selectively over growth. A comparison of piceatannol's ability to inhibit *S. mutans* biofilm with resveratrol, and E-stilbene shows our lead to be the most potent at 200 μM (Table 8 and FIG. 15A). Upon further analysis of the compounds' effect on *S. mutans* growth, we have identified a previously studied resveratrol and a novel agent called piceatannol to demonstrate biofilm inhibitory activity with $IC_{50}$ values of 102 μM and 52 μM respectively, with minimal bactericidal activity. Piceatannol was chosen for further analysis due to its source of existence, simplicity of structure, and ease of synthesis. Piceatannol is found in several natural sources ranging from roots of Norway spruces, seeds of the palm *Aiphanes horrida* and in *Gnetum cleistostachyum*. It is also a metabolite of resveratrol, which is found in red wine, grapes, and passion fruit.

TABLE 8

Biofilm and growth inhibitory activities of stilbenes

| Entry | NSC Code | Structure | Biofilm $IC_{50}$ (μM) | Growth $MIC_{50}$ (μM)[a] | Selectivity |
|---|---|---|---|---|---|
| 1 | NA | 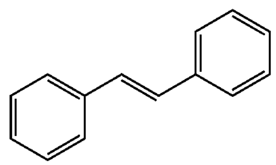 [SMILES: C(=C\c1ccccc1)/c1ccccc1] | NI | NI | NA |
| 2 | NA | 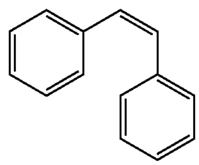 | NI | NI | NA |
| 3 | 403525 | 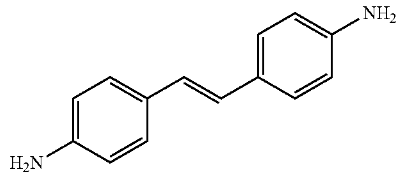 [SMILES: Nc1ccc(/C=C/c2ccc(N)cc2)cc1] | NI | NI | NA |
| 4 | 4184 | 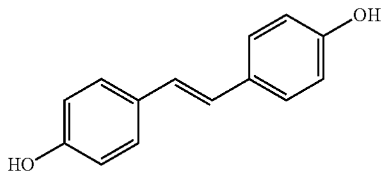 | 344 ± 17 | 854 ± 58 | 2.4 |
| 5 | 78326 | 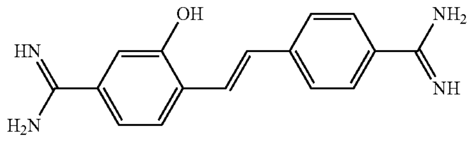 | 104 ± 7 | 179 ± 23 | 1.7 |

TABLE 8-continued
Biofilm and growth inhibitory activities of stilbenes
| Entry | NSC Code | Structure | Biofilm $IC_{50}$ (μM) | Growth $MIC_{50}$ (μM)[a] | Selectivity |
|---|---|---|---|---|---|
| 6 | 43312 | 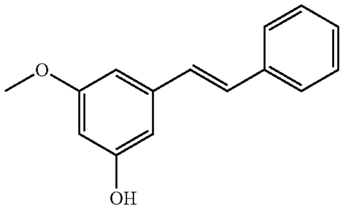 [SMILES: COc1cc(O)cc(/C=C/c2ccccc2)c1] | 477 ± 51 | 546 ± 25 | 1.1 |
| 7 | NA | 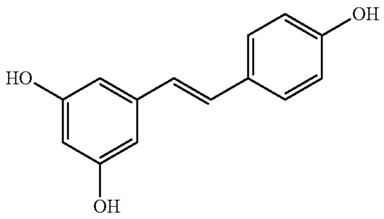 [SMILES: Oc1ccc(/C=C/c2cc(O)cc(O)c2)cc1] | 102.2 ± 4 | 546.4 ± 15.9 | 5.3 |
| 8 | 365798 | 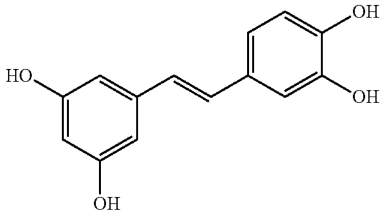 [SMILES: Oc1cc(O)cc(/C=C/c2ccc(O)c(O)c2)c1] | 52 ± 6 | 564 ± 37.8 | 10.8 |
| 9 | 381864 | 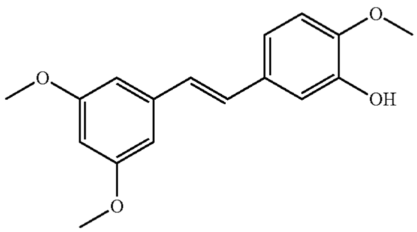 | 122 ± 11 | 137 ± 6 | 1.1 |
| 10 | 70861 | 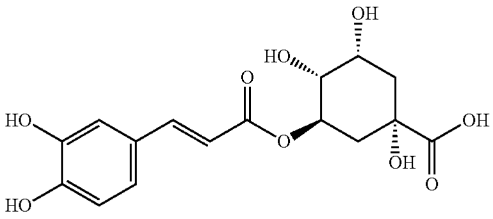 [SMILES: O=C(/C=C/c1ccc(O)c(O)c1)O[C@@H]1C[C@](O)(C(=O)O)C[C@@H](O)[C@H]1O] | 518 ± 85 | 1724 ± 53 | 3.3 |
| 11 | 123262 | 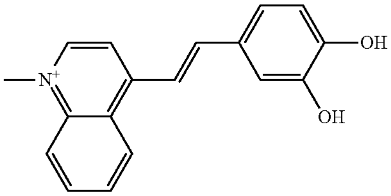 [SMILES: C[n+]1ccc(/C=C/c2ccc(O)c(O)c2)c2ccccc21] | 104 ± 6 | >400 | 4.0 |
| 12 | 43321 | 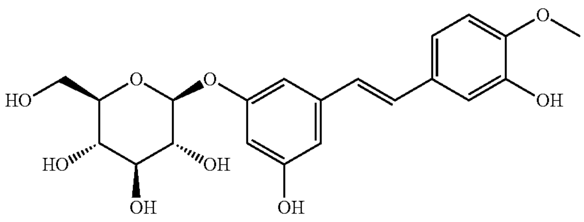 [SMILES: COc1ccc(/C=C/c2cc(O)cc(O[C@@H]3O[C@H](CO)[C@@H](O)[C@H](O)[C@H]3O)c2)cc1O] | 106 ± 11 | 134 ± 11 | 1.2 |

TABLE 8-continued

| Biofilm and growth inhibitory activities of stilbenes | | | | | |
|---|---|---|---|---|---|
| Entry | NSC Code | Structure | Biofilm $IC_{50}$ (μM) | Growth $MIC_{50}$ (μM)[a] | Selectivity |
| 13 | 16952974 | 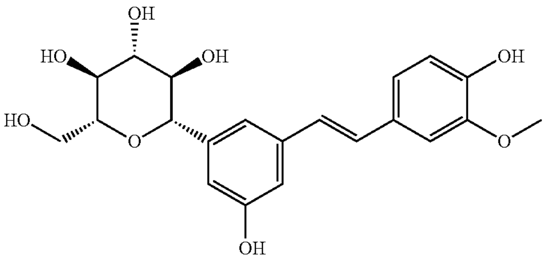 [SMILES: COc1cc(/C=C/c2cc(O)cc([C@@H]3O[C@H](CO)[C@@H](O)[C@H](O)[C@H]3O)c2)ccc1O] | NI | NI | NA |

[a]Average of at least 5 measurements;
NI No inhibition;
NA Not available.

Figure 15D:
FIG. 15D shows the docking pose of piceatannol and acarbose in the GtfC active site.

Docking analysis of piceatannol in the GtfC active site. Our docking model (FIG. 15D) of piceatannol shows several key interactions. This pocket docked by the compound is at the same space occupied by acarbose, a weak inhibitor of GtfC that was co-crystalized with GtfC (Ito, K.; Ito, S.; Shimamura, T.; Weyand, S.; Kawarasaki, Y.; Misaka, T.; Abe, K.; Kobayashi, T.; Cameron, A. D.; Iwata, S., Crystal Structure of Glucansucrase from the Dental Caries Pathogen *Streptococcus mutans. Journal of Molecular Biology* 2011, 408 (2), 177-186). The best docked structure, visualized by UCSF Chimera molecular modeling system, showed interactions of six amino acids: Asp909, Asp477, Glu515, His587, Asp480, and Trp517. It is already reported in the literature that binding of acarbose to Glu515 compromised the acid/base catalyst function, while interaction with Trp517 blocked the acceptor glycosyl moiety, explaining the inhibitory effects shown by acarbose when bound to GtfC (Ito, K.; Ito, S.; Shimamura, T.; Weyand, S.; Kawarasaki, Y.; Misaka, T.; Abe, K.; Kobayashi, T.; Cameron, A. D.; Iwata, S., Crystal Structure of Glucansucrase from the Dental Caries Pathogen *Streptococcus mutans. Journal of Molecular Biology* 2011, 408 (2), 177-186). The hydroxyl functional groups interact with Asp477, Asp480, and Glu515, and have interactions with Asp909 and Trp517. The binding free energy of piceatannol predicted by FlexX software was −25 kJ/mol, indicating a stable and strong binding with the protein.

Figure 16A:
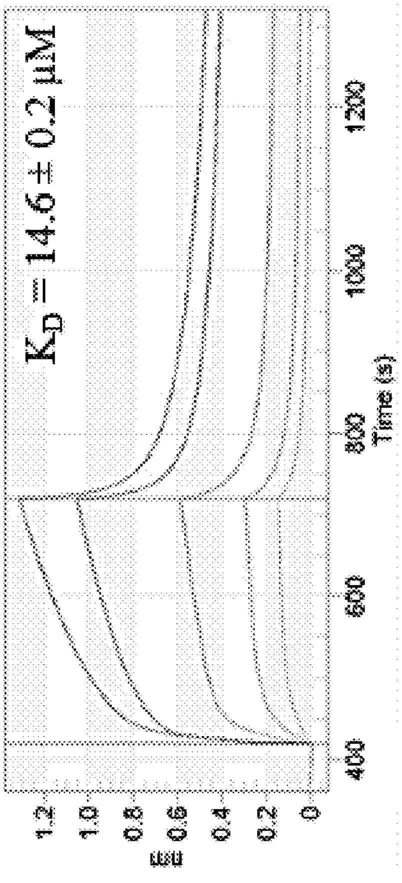
FIG. 16A-16F show OctetRed96 Analysis of (FIG. 16A) Piceatannol and GtfB, (FIG. 16B) Piceatannol and GtfC, (FIG. 16C) Resveratrol and GtfB, and (FIG. 16D) Resveratrol and GtfC.
Figure 16B:
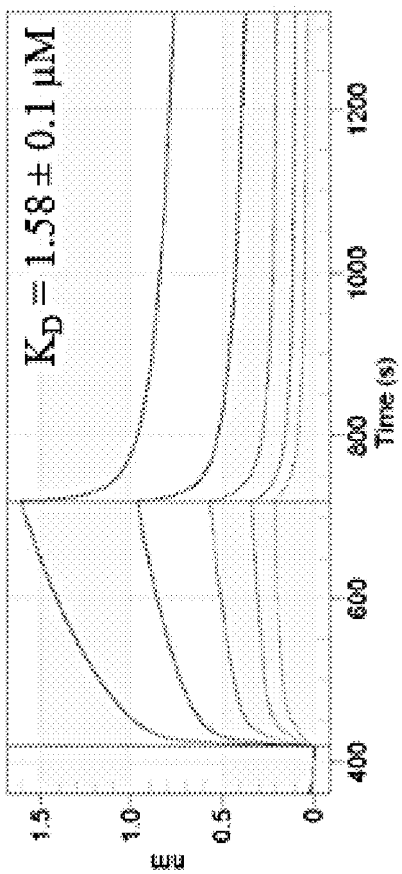
Figure 16C:
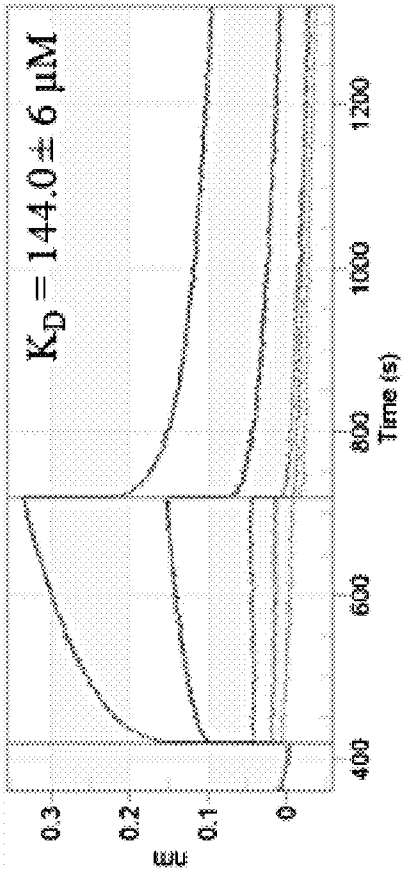
Figure 16D:
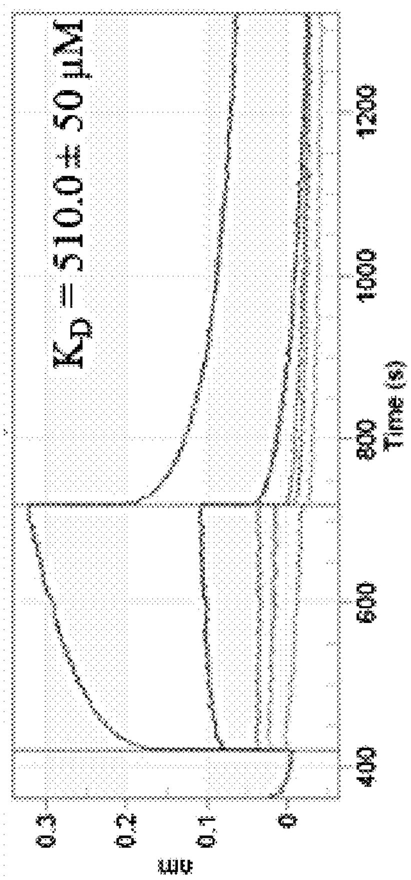

Binding and Inhibition of Gtfs by Piceatannol and Resveratrol. To verify the docking results the Octet® system was used to evaluate binding of potent small molecule compounds to GtfB and GtfC. Recombinant His tagged GtfB and GtfC were produced, and the HIS1K Biosensor was employed to capture and quantify His tagged Gtfs for binding kinetic characterization. The kinetics of the binding of piceatannol and resveratrol with GtfB and GtfC were examined and shown in FIGS. 16A-16D. The best binding fits were observed with piceatannol, producing $K_D$ values of 14.6 μM (FIG. 16A), and 1.58 μM (FIG. 16B) for GtfB and GtfC, respectively. This data is consistent with the zymogram results, as the compound is more active against GtfC when compared to GtfB. Resveratrol was also subjected to the same analysis. Its $K_D$ values are 144 μM and 510 μM for GtfB and GtfC, respectively (FIGS. 16C and 16D). The piceatannol scaffold is more potent towards GtfB. All four experiments produced reliable $R^2$ values and fit well in the 1:1 binding mode.

Figure 16E:
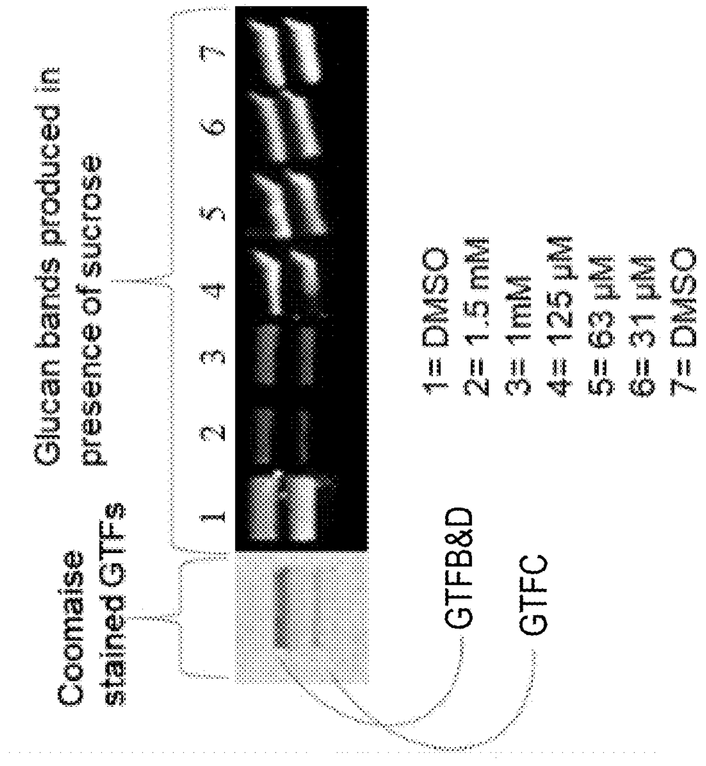
Figure 16F:
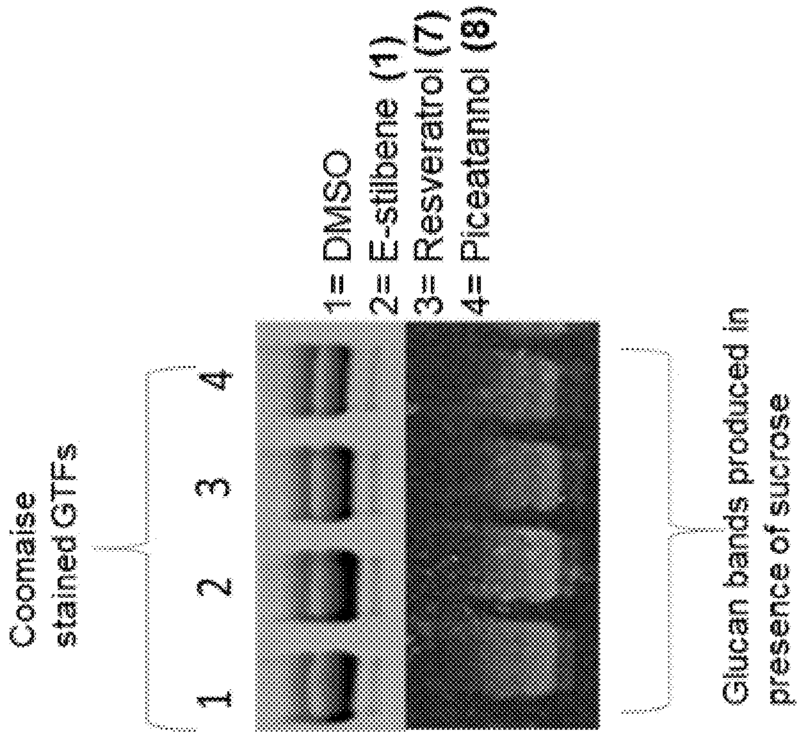

In addition to quantitative analysis, a zymogram assay was performed to evaluate the inhibition of Gtf enzymatic activity qualitatively. Natural products resveratrol and piceatannol were added to the growth media initially to see if they had an effect of glucan production. The results parallel the observations seen in biofilms, as piceatannol greatly reduced glucan production when compared to the DMSO control. Resveratrol showed marginal inhibition. In order to assess a dose dependent effect, a zymogram assay was performed using same amounts of Gtf proteins in each of the lanes resolved on the SDS-PAGE gels and submerged in different concentrations of the lead compound. Our results show that apparent decrease in the bottom band where GtfC produces its glucans, a decrease in the upper band is also observed in which GtfB and GtfD are comigrated, suggesting that the compound inhibits at least two, if not all three Gtfs (FIGS. 16E and 16F). The zymogram assay on resveratrol and E-stilbene paralleled the biofilm inhibition. A higher inhibition was seen with piceatannol in comparison to resveratrol, while the inactive E-stilbene analog in the biofilm assay showed no glucan inhibition. These results suggest that the biofilm inhibition by the potent compound is directly related to the inhibition of glucan production by Gtfs.

Figure 17A:
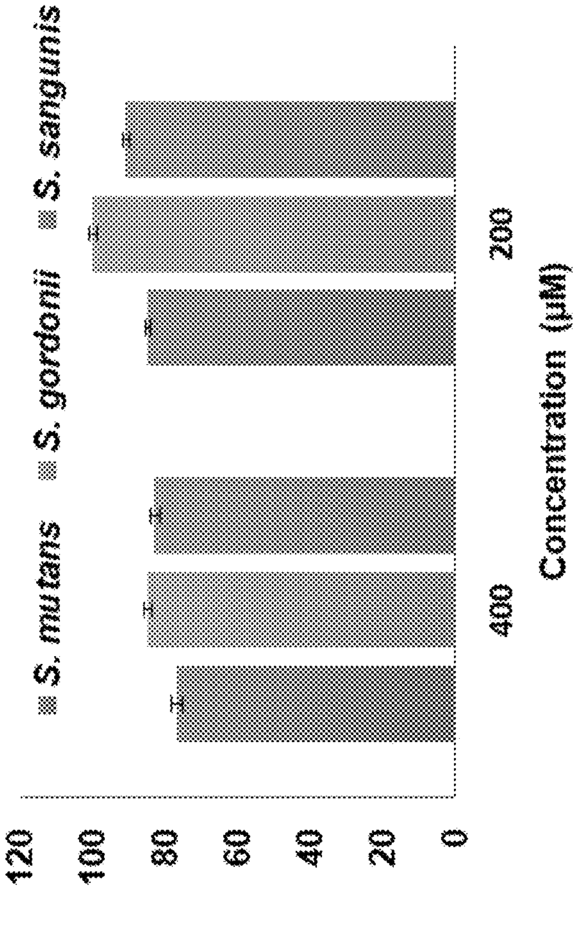
FIG. 17A shows effect of piceatannol on growth of *S. mutans, S. gordonii*, and *S. sanguinis* assessed by an alamar blue protocol.

Piceatannol did not inhibit the growth of commensal streptococcal species. To evaluate the selectivity of piceatannol, its ability to affect bacterial viability in both biofilm and planktonic cells of *S. mutans* was examined. The viability of the biofilms and planktonic cells of *S. mutans* was not significantly impacted by the treatment of piceatannol. Furthermore, piceatannol was used to assess its effect on the growth of other oral commensal species (*S. sanguinis* and *S. gordonii*) at concentrations ranging from 50-400 μM. At the biofilm $IC_{50}$ value of 52 μM, less than 10% of growth of *S. mutans, S. sanguinis* and *S. gordonii* is inhibited by piceatannol. Piceatannol inhibits *S. mutans* cell viability by 37% at 400 μM, and has reduced toxicity to *S. sanguinis* and *S. gordonii*, decreasing cell density by ~15-18% (FIG. 17A). Thus, piceatannol exhibits significant selectivity for biofilms.

Figure 17B:
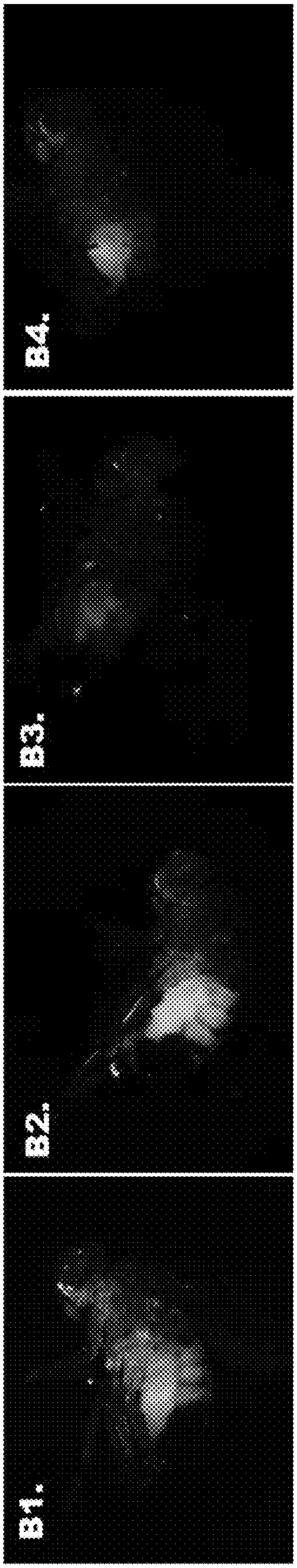
FIG. 17B shows fluorescent microscopy images of *S. mutans* colonization in *Drosophila* with the following conditions: (panel B1) treatment with sucrose, (panel B2) treatment with DMSO, (panel B3) ΔgtfB mutant strain and (panel B4) treatment with 50 μM Piceatannol.

Piceatannol inhibited *S. mutans* colonization in vivo. The effect of piceatannol on *S. mutans* colonization in vivo was first evaluated using a sucrose-dependent *drosophila* colonization model (Peng, X.; Zhang, Y.; Bai, G.; Zhou, X.; Wu, H., Cyclic di-AMP mediates biofilm formation. *Molecular microbiology* 2015, 99 (5), 945-959). Briefly, Gfp tagged *S. mutans* bacteria were used to infect flies along with the treatment of piceatannol at 50 μM in a feeding-assay (FIG. 17B). DMSO was used as a negative control (FIG. 17B panel B2) and gtfB mutant, a known biofilm defective strain, was used as a positive control (FIG. 17B panel B3). The intensity of the fluorescence was measured in the guts of the flies fed with the Gfp tagged bacteria after 7 days of infection. A significant decrease in fluorescence was observed when treated by piceatannol (FIG. 17B panel B4), producing an effect similar to that observed in the gtf mutant (FIG. 17B panel B3). This data suggest piceatannol inhibits *S. mutans* colonization in vivo.

Figure 18A:
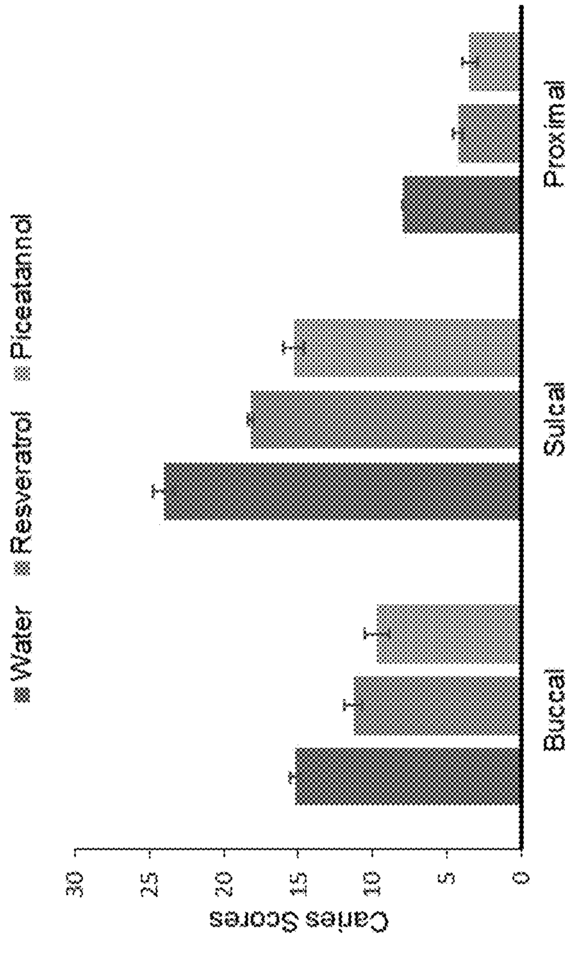
FIG. 18A-18B show effect of resveratrol and piceatannol treatment on the susceptibility of gnotobiotic rats to *S. mutans* UA159 induced dental caries.
Figure 18B:
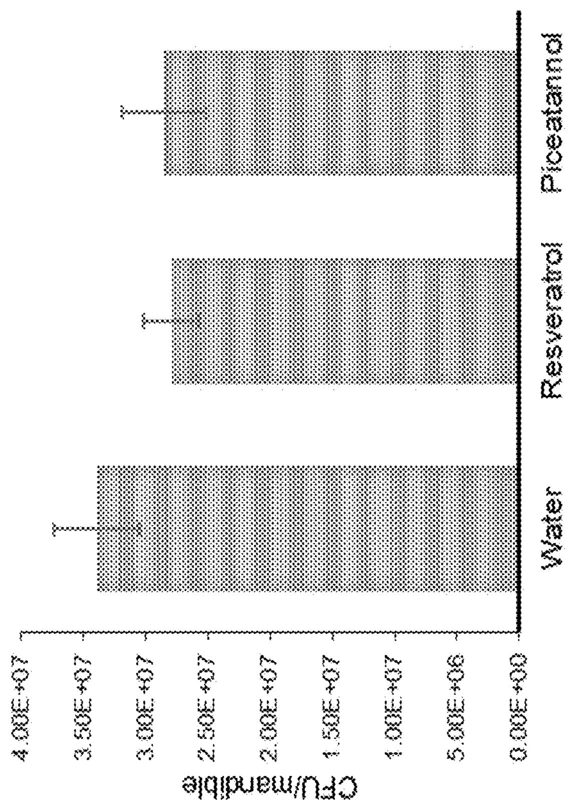

The in vivo efficacy of resveratrol and piceatannol was further evaluated using a rat model of dental caries (Michalek, S. M.; McGhee, J. R.; Navia, J. M., Virulence of *Streptococcus mutans*: a sensitive method for evaluating cariogenicity in young gnotobiotic rats. *Infection and immunity* 1975, 12 (1), 69-75; Michalek, S. M.; McGhee, J. R.; Shiota, T.; Devenyns, D., Low sucrose levels promote extensive *Streptococcus mutans*-induced dental caries. *Infection and immunity* 1977, 16 (2), 712-4). The treatment of both stilbenes produced a significant reduction in the buccal, sulcal, and proximal surface caries scores of the treated animals, with piceatannol demonstrating a greater reduction (FIG. 18A). While the bacterial colonization appeared to be reduced by the treatment with the tested stilbenes, it was not statistically significant, when compared with the control group treated with water (FIG. 18B). These data suggest that both piceatannol and resveratrol selectively inhibit virulence factors, Gtfs and Gtf-mediated biofilm formation and do not affect the bacterial growth. At the time of sacrifice and the removal of the mandible, there were no obvious differences in the oral tissue (mucosal and gingival tissues) between the treated and non-treated rats. Furthermore, because the treated rats did not lose weight over the course of the study in comparison with the control group, we believe that the natural stilbenes are safe and non-toxic.

Modulation of cariogenic biofilms formed by *S. mutans* is a viable preventive strategy for the prevention and treatment of dental caries. Considering the selectivity of polyphenols towards inhibiting *S. mutans* biofilms rather than altering its cell viability, polyphenol scaffolds were explored in an effort to develop selective anti-biofilm agents. Here, the antimicrobial and antibiofilm activities of a small series of stilbenes were investigated against the cariogenic bacterium *S. mutans*. The identified lead compound, piceatannol exhibited anti-biofilm activity against *S. mutans* in the low micromolar range with a selectivity index of about 11 through the inhibition of the Gtfs, a key virulence factor of *S. mutans*. This compound showed marginal inhibition on the growth of *S. mutans, S. sanguinus*, and *S. gordonii* at high micromolar concentrations, suggesting its selectivity and non-toxicity. Piceatannol inhibited *S. mutans* induced cariogenicity in vivo. Thus, this study demonstrated a virulence-selective therapeutic approach.

A co-complex crystal structure of GtfC and acarbose (PDB code: 3AIC) was utilized for the purposes of in silico docking. The active site residues were selected using the a 6.5 Å parameter of the crystallized ligand, acarbose and residues Asp588 (H-acceptor) and Gln960 (H-donor) were used to generate a pharmacophore. We accessed the ZINC database to obtain a small library of polyphenolic small molecules and docked them using FlexX. Binding energies less than −20 kJ/mol were selected for further investigation such as their drug like properties based on Lipinski's rules, binding interactions with key residues and for synthetic feasibility.

Bacterial strains and culture conditions. THB agar plate, 5% $CO_2$ in Todd-Hewitt (TH) broth, or in chemically defined biofilm medium supplemented with 1% sucrose were used to grow *S. mutans* UA159 and various Gtf mutants, *S. sanguinis* SK36, and *S. gordonii* DL1 statically at 37° C. Small molecule compounds were obtained from National Cancer Institute (NCI). 10 mM stock solutions were prepared in DMSO and arrayed in a 96-well format for biological screening.

*S. mutans* biofilm formation and inhibition assays. A well-established protocol to study *S. mutans* biofilm formation in 96-well flat-bottom polystyrene microtiter plates was used, in triplicate (Mattos-Graner, R. O.; Napimoga, M. H.; Fukushima, K.; Duncan, M. J.; Smith, D. J., Comparative analysis of Gtf isozyme production and diversity in isolates of *Streptococcus mutans* with different biofilm growth phenotypes. *Journal of clinical microbiology* 2004, 42 (10), 4586-4592). The stock solutions were made up in 100% DMSO, and final concentration of DMSO used in the assays was 1%. Minimum biofilm inhibitory concentration (MBIC) of compounds was determined by serial dilutions. The most potent of these scaffolds were progressed into further evaluations.

Inhibition of the activity of Gtfs determined by zymographic assays. A previously reported zymographic assay was utilized for the investigation of Gtf enzymatic activity, as described in Example 1. A 1:100 in fresh 5 mL THB with 50 μL of selective compounds at a series of concentrations was used to dilute overnight *S. mutans* UA159 cultures and grown to $OD_{470}$ of 1.0. The final concentration of DMSO used in the assays was 1%. After the centrifugation at 4° C., the supernatants were isolated and filtered through a 0.22-μm-pore-size filter membrane and dialyzed at 4° C. against 0.02 M sodium phosphate buffer (pH 6.8), with 10 μM phenylmethylsulfonyl fluoride (PMSF), followed by a second dialysis against 0.2 mM sodium phosphate containing 10 μM PMSF. 4 mL of samples were concentrated to 40 μL by 100K Amicon Ultra-4 centrifugal filter (Merck Millipore Ltd.). Next, 10 μL of each concentrated culture supernatant was applied to 8% SDS-PAGE in duplicate. One gel was subjected to Coomassie blue dye for protein detection, while the other one was subjected to zymographic assay. The resultant white opaque glucan bands were visualized against a black background.

Cell viability of *S. mutans* and commensal *S. gordonii* and *S. sanguinis*. Cell viability and the small molecules' effect on it were investigated accordingly to previous reports (Liu, C.; Worthington, R. J.; Melander, C.; Wu, H., A new small molecule specifically inhibits the cariogenic bacterium *Streptococcus mutans* in multispecies biofilms. *Antimicrobial agents and chemotherapy* 2011, 55 (6), 2679-87). DMSO served as a control group and provided a relative comparison for the number of colony-forming units (CFU) per milliliter for each compound at different concentrations was determined after incubation for 24 h at 37° C. The final concentration of DMSO used in the assays was 1%.

Colonization of *Drosophila*. Colonization of flies was performed as described. Cultures of Gfp-tagged (green fluorescent protein) *S. mutans* UA159 grown to middle log phase were spun down and re-suspended in a solution containing 5% sucrose and 50 μM of each compound. 100 μL of re-suspended cells were aliquoted onto a sterile filter that was placed on the surface of 5 mL of solidified 5% sucrose agar in a plastic vial. Upon the drying of the vials at room temperature for 30 min, the flies were introduced to the vessels. Male Canton S flies (1-3 days old) were treated with antibiotics for 2 days and starved for 3 h before the addition to vials supplied with *S. mutans* (10-14 flies per vial). Nikon elipse 90i microscope, equipped with an Epi-fluorescence and NIS elements AR imaging system was used to analyze the colonization of flies by Gfp-tagged strains.

Dental caries rat model. Fischer 344 rats used in this study were bred and maintained in trexler isolators. At the age of 20 days, rat pups were removed from isolators and randomly assigned into five groups. Group A consisting of 3 female+3 male rats were treated with resveratrol; Group B consisting of 3 female+3 male rats were treated with piceatannol; Group C consisting of 3 female+3 male rats were treated with water; Group D consisting of 3 female+2 male rats were not treated; Group E consisting of 2 female+3 male rats were not treated nor infected by UA159. Rats were then infected with *S. mutans* UA159 for three consecutive days and provided a caries-promoting Diet 305, which contains 5% sucrose (TD.80406, diet with 62% corn starch, Harlan Laboratories, Madison, Wis.) and sterile drinking water ad libitum. The rats were then treated with the stilbene, water, or not treated respective of their study group as described above at 100 μM twice daily for 4 weeks beginning 10 days post infection. Drinking water was withheld for one hour after each treatment. Rats were weighed at weaning and after 45 days at the termination of the experiment. The animals were euthanized, their mandibles excised for microbiological analysis of plaque samples on MS agar plates and BAP and for scoring of caries by the method of Keyes. All experimental protocols were approved by the University of Alabama at Birmingham Institutional Animal Care and Use Committee and in accordance with the relevant guidelines and regulations.

OctetRed analysis. OctetRed full kinetic binding analysis was performed for Piceatannol and Resveratrol against GtfB and GtfC. GtfC and GtfB were purified. The Octet® Red96 system (ForteBio, Menlo Park, Calif.) was used to determine the rate constant, $K_D$. Phosphate buffer with 2.5% (w/v) DMSO was used as a negative control. The dip-and-read Anti-Penta-HIS (HIS1K) Biosensor containing Penta-His antibody from Qiagen pre-immobilized on a fiber optic biosensor was used to capture the Gtf proteins with high affinity and specificity. 3-fold serial dilution treatment from 200, 66.6, 22.2, 7.4, 2.46 to 0 μM was used to study the stilbenes in phosphate buffer. Sensorgrams and the accuracy of the analysis was calculated using the ForteBio OctetRed analysis software (ForteBio, Menlo Park, Calif.).

The foregoing is illustrative of the present invention, and is not to be construed as limiting thereof. The invention is defined by the following claims, with equivalents of the claims to be included therein.

That which is claimed:

1. A compound selected from the group consisting of:

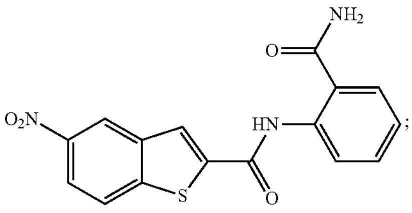

;

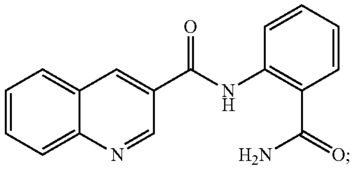

;

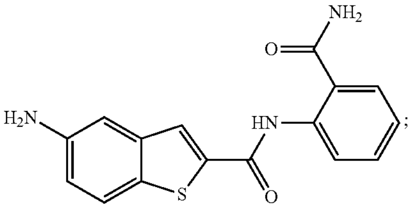

; and

-continued

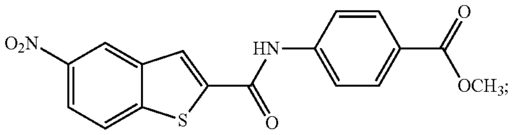

; and

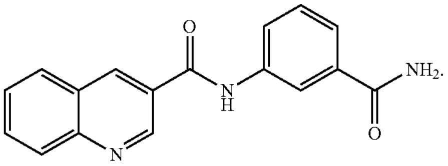

.

2. A compound selected from the group consisting of:

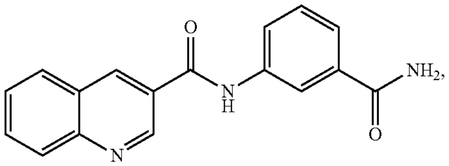

, and

-continued

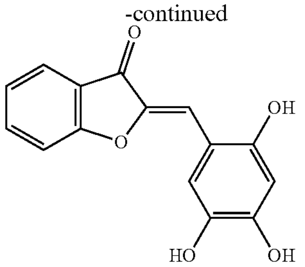

and

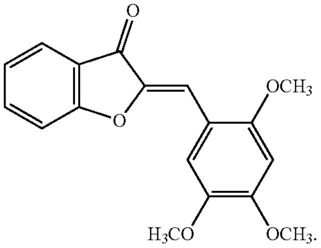

3. A pharmaceutical formulation comprising a compound of claim 1, and a pharmaceutically acceptable carrier.

4. A method of inhibiting biofilm formation in a subject in need thereof, comprising administering to the subject an effective amount of the pharmaceutical formulation of claim 3, thereby inhibiting biofilm formation.

5. The method of claim 4, wherein the biofilm is a *Streptococcus mutans* biofilm.

6. The method of claim 4, wherein the subject is a human subject.

7. The method of claim 4, wherein the pharmaceutical formulation is in a form selected from the group consisting of a tooth paste, oral rinse, gel, an additive to a digestible product and a strip comprising the pharmaceutical formulation to be applied to the teeth of a subject.

8. A method of preventing, inhibiting and/or treating the formation of dental caries in a subject in need thereof, comprising administering to the subject an effective amount of the pharmaceutical formulation of claim 3, thereby inhibiting and/or treating the formation of dental caries.

9. A method of preventing, inhibiting and/or treating the formation of denture plaques in a denture of a subject in need thereof, comprising contacting the denture with an effective amount of the pharmaceutical formulation of claim 3, thereby preventing, inhibiting and/or treating the formation of denture plaques.

10. The method of claim 9, wherein the pharmaceutical formulation is in a form of a soaking solution or rinse.

11. The method of claim 9, wherein the denture is contacted while in the subject.

12. A pharmaceutical formulation comprising a compound of claim 2, and a pharmaceutically acceptable carrier.

13. A method of inhibiting biofilm formation in a subject in need thereof, comprising administering to the subject an effective amount of the pharmaceutical formulation of claim 12, thereby inhibiting biofilm formation.

14. The method of claim 13, wherein the biofilm is a *Streptococcus mutans* biofilm.

15. The method of claim 13, wherein the subject is a human subject.

16. The method of claim 13, wherein the pharmaceutical formulation is in a form selected from the group consisting of a tooth paste, oral rinse, gel, an additive to a digestible product and a strip comprising the pharmaceutical formulation to be applied to the teeth of a subject.

17. A method of preventing, inhibiting and/or treating the formation of dental caries in a subject in need thereof, comprising administering to the subject an effective amount of the pharmaceutical formulation of claim 12, thereby inhibiting and/or treating the formation of dental caries.

18. A method of preventing, inhibiting and/or treating the formation of denture plaques in a denture of a subject in need thereof, comprising contacting the denture with an effective amount of the pharmaceutical formulation of claim 12, thereby preventing, inhibiting and/or treating the formation of denture plaques.

19. The method of claim 18, wherein the pharmaceutical formulation is in a form of a soaking solution or rinse.

20. The method of claim 18, wherein the denture is contacted while in the subject.

* * * * *

UNITED STATES PATENT AND TRADEMARK OFFICE

CERTIFICATE OF CORRECTION

PATENT NO. : 11,866,416 B2
APPLICATION NO. : 17/044483
DATED : January 9, 2024
INVENTOR(S) : Velu et al.

It is certified that error appears in the above-identified patent and that said Letters Patent is hereby corrected as shown below:

In the Specification

Column 6, Line 55: correct "at 19" to read --at ~19--

Column 10, Line 67: correct "—$C_{10}$ alkyl" to read -- —$C_{1-10}$ alkyl--

Column 11, Line 8: correct "$X_1$" to read --$X_{11}$--

Column 14, Line 34: correct "—$CH_2$—$NHZ_1$," to read -- —$CH_2$—$NHZ_{11}$,--

Column 14, Line 39: correct "$C_1$ alkyl" to read --$C_{1-4}$ alkyl--

Column 15, Line 61: correct "—$C_1$" to read -- —Cl--

Column 87, Line 13: correct "GtC" to read --GtfC--

Column 90, Line 6: correct "gfs" to read --gtfs--

Column 91, Line 11: correct "ZTNC" to read --ZINC--

Column 91, Line 24: correct "$C_{102}$" to read --CO2--

Column 94, Line 28: correct "stud" to read --study--

Column 101, Line 47: correct "15c, $R^2$ = 2′,4′,5′ di-$OCH_3$" to read --15c, $R^2$ = 2′,4′ di-$OCH_3$--

Column 107, Line 23: correct "J=8.4" to read --$J_1$=8.4--

Column 107, Line 50: correct "11511.3, 121.9," to read --114.5, 116.3, 121.9--

Signed and Sealed this
Twenty-third Day of April, 2024

Katherine Kelly Vidal

Katherine Kelly Vidal
*Director of the United States Patent and Trademark Office*

Column 107, Line 66: correct "J'$_2$ 11.7 Hz," to read --$J_1$=11.7 Hz,--

Column 109, Line 32: correct "H NMR" to read --$^1$H NMR--

Column 109, Line 50: correct "H NMR" to read --$^1$H NMR--

Column 109, Line 56: correct "$C_8H_{18}O_5$" to read --$C_{18}H_{18}O_5$--

Column 110, Line 43: correct "Too" to read --(Koo--

Column 119, Line 9: correct "gtf mutant" to read --gtfB mutant--

SEQUENCE LISTING

```
<160> NUMBER OF SEQ ID NOS: 14

<210> SEQ ID NO 1
<211> LENGTH: 19
<212> TYPE: DNA
<213> ORGANISM: Artificial
<220> FEATURE:
<223> OTHER INFORMATION: primer

<400> SEQUENCE: 1

ttagcatgat tggggctgc                                                   19


<210> SEQ ID NO 2
<211> LENGTH: 43
<212> TYPE: DNA
<213> ORGANISM: Artificial
<220> FEATURE:
<223> OTHER INFORMATION: primer

<400> SEQUENCE: 2

ttgttcatgt aatcactcct tcgataacat atacgttaca aac                        43


<210> SEQ ID NO 3
<211> LENGTH: 40
<212> TYPE: DNA
<213> ORGANISM: Artificial
<220> FEATURE:
<223> OTHER INFORMATION: primer

<400> SEQUENCE: 3

ggtatactac tgacagcttc cactgacata gcttaacgtg                            40


<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
```

gacaaacata ccttagacgc 20

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
aaggagtgat tacatgaaca a 21

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
gaagctgtca gtagtatacc 20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
cctacgggag gcagcagtag 20

<210> SEQ ID NO 8
<211> LENGTH: 23
<212> TYPE: DNA
<213> ORGANISM: Artificial
<220> FEATURE:
<223> OTHER INFORMATION: primer

<400> SEQUENCE: 8
caacagagct ttacgatccg aaa 23

<210> SEQ ID NO 9
<211> LENGTH: 28
<212> TYPE: DNA
<213> ORGANISM: Artificial
<220> FEATURE:
<223> OTHER INFORMATION: primer

<400> SEQUENCE: 9
catacagtaa cgacaatcag tagctcta 28

<210> SEQ ID NO 10
<211> LENGTH: 26
<212> TYPE: DNA
<213> ORGANISM: Artificial
<220> FEATURE:
<223> OTHER INFORMATION: primer

<400> SEQUENCE: 10
gtacgaactt tgccgttatt gtcata 26

<210> SEQ ID NO 11
<211> LENGTH: 24
<212> TYPE: DNA

-continued

```
<213> ORGANISM: Artificial
<220> FEATURE:
<223> OTHER INFORMATION: primer

<400> SEQUENCE: 11

gccacggaac aagcagttct gtaa                                         24


<210> SEQ ID NO 12
<211> LENGTH: 25
<212> TYPE: DNA
<213> ORGANISM: Artificial
<220> FEATURE:
<223> OTHER INFORMATION: primer

<400> SEQUENCE: 12

taataccaat tatttcctaa gctaa                                        25


<210> SEQ ID NO 13
<211> LENGTH: 23
<212> TYPE: DNA
<213> ORGANISM: Artificial
<220> FEATURE:
<223> OTHER INFORMATION: primer

<400> SEQUENCE: 13

cacaggcaaa agctgaatta aca                                          23


<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14

gaatggccgc taagtcaaca g                                            21
```